US012649710B2

(12) United States Patent　　　(10) Patent No.:　US 12,649,710 B2

Amakawa et al.　　　　　　　　(45) Date of Patent:　　Jun. 9, 2026

(54) PROCESS FOR THE CONTINUOUS PRODUCTION OF EITHER ACROLEIN OR ACRYLIC ACID AS THE TARGET PRODUCT FROM PROPENE

(71) Applicant: BASF SE, Ludwigshafen am Rhein (DE)

(72) Inventors: Kazuhiko Amakawa, Ludwigshafen am Rhein (DE); Lukas Schulz, Ludwigshafen am Rhein (DE); Michael Bender, Ludwigshafen am Rhein (DE); Klaus Joachim Mueller-Engel, Ludwigshafen am Rhein (DE); Christian Walsdorff, Ludwigshafen am Rhein (DE); Signe Unverricht, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 892 days.

(21) Appl. No.: 17/628,897

(22) PCT Filed: Jul. 14, 2020

(86) PCT No.: PCT/EP2020/069894

§ 371 (c)(1),
(2) Date: Jan. 20, 2022

(87) PCT Pub. No.: WO2021/013640

PCT Pub. Date: Jan. 28, 2021

(65) Prior Publication Data

US 2022/0259131 A1　　Aug. 18, 2022

(30) Foreign Application Priority Data

Jul. 24, 2019　(EP) .................................... 19188112

(51) Int. Cl.
*C07C 51/145* (2006.01)
*B01J 23/887* (2006.01)
(Continued)

(52) U.S. Cl.
CPC ......... *C07C 51/145* (2013.01); *B01J 23/8876* (2013.01); *B01J 35/55* (2024.01); *C07C 45/505* (2013.01)

(58) Field of Classification Search
CPC ...... C07C 51/145; C07C 45/505; B01J 35/50; B01J 23/8876
See application file for complete search history.

(56) References Cited

U.S. PATENT DOCUMENTS 3,433,840 A　3/1969　Takesaburo et al.
4,297,247 A　10/1981　Krabetz et al.
(Continued)

FOREIGN PATENT DOCUMENTS

DE　2909671 A1　10/1980
DE　3429391 A1　2/1985
(Continued)

OTHER PUBLICATIONS

DE102005056377A1 (Machhammer et al. English language machine translation) (Year: 2007).*
(Continued)

*Primary Examiner* — Amy C Bonaparte
*Assistant Examiner* — Derek Rhoades
(74) *Attorney, Agent, or Firm* — Faegre Drinker Biddle & Reath LLP

(57) ABSTRACT

A process for the continuous production of either acrolein or acrylic acid as the target product from propene comprising a catalyzed gas phase partial oxidation of propene to yield a product gas containing the target product, transferring the target product in a separating zone from the product gas into
(Continued)

the liquid phase and conducting out of the separating zone a stream of residual gas the major portion of which is returned into the partial oxidation and the remaining portion of said stream is purged from the process as off-gas from which synthesis gas can be produced or which can be added to synthesis gas produced otherwise.

18 Claims, 1 Drawing Sheet

(51) Int. Cl.
*B01J 35/55* (2024.01)
*C07C 45/50* (2006.01)

(56) References Cited

U.S. PATENT DOCUMENTS

| | | | |
|---|---|---|---|
| 5,315,037 A | 5/1994 | Sakamoto et al. | |
| 5,684,188 A | 11/1997 | Hefner et al. | |
| 5,821,390 A | 10/1998 | Ruppel et al. | |
| 6,090,977 A | 7/2000 | Hefner et al. | |
| 6,312,658 B1 | 11/2001 | Hufton et al. | |
| 7,183,428 B2 | 2/2007 | Ueno et al. | |
| 7,211,692 B2 * | 5/2007 | Dieterle et al. | C07C 51/16 562/535 |
| 8,334,395 B2 | 12/2012 | Andresen et al. | |
| 9,115,067 B1 * | 8/2015 | Bunning et al. | C07C 45/35 568/479 |
| 10,457,634 B2 * | 10/2019 | Erlandsson et al. | C07C 273/14 |
| 2004/0015012 A1 | 1/2004 | Hammon et al. | |
| 2005/0020851 A1 | 1/2005 | Olbert et al. | |
| 2005/0042154 A1 | 2/2005 | Olbert et al. | |
| 2009/0018220 A1 | 1/2009 | Fitzpatrick | |

FOREIGN PATENT DOCUMENTS

| | | | | |
|---|---|---|---|---|
| DE | 4431957 A1 | 3/1995 | | |
| DE | 19815281 A1 | 10/1999 | | |
| DE | 19855913 A1 | 6/2000 | | |
| DE | 19910506 A1 | 9/2000 | | |
| DE | 10046928 A1 | 4/2002 | | |
| DE | 10213998 A1 | 3/2003 | | |
| DE | 102004032129 A1 | 3/2005 | | |
| DE | 102005009885 A1 | 9/2006 | | |
| DE | 102005013039 A1 | 9/2006 | | |
| DE | 102005037678 A1 | 2/2007 | | |
| DE | 102005056377 A1 * | 5/2007 | | C07C 47/22 |
| DE | 102018200841 A1 | 7/2019 | | |
| EP | 0293859 A1 | 12/1988 | | |
| EP | 0700714 A1 | 3/1996 | | |
| EP | 0700983 A2 | 3/1996 | | |
| EP | 0714700 A2 | 6/1996 | | |
| EP | 0731080 A1 | 9/1996 | | |
| EP | 1159244 A1 | 12/2001 | | |
| EP | 1180508 A1 | 2/2002 | | |
| EP | 1005908 B1 | 9/2006 | | |
| GB | 2146636 A | 4/1985 | | |
| WO | 97/48669 A1 | 12/1997 | | |
| WO | 00/53556 A1 | 9/2000 | | |
| WO | 00/53557 A1 | 9/2000 | | |
| WO | 00/53558 A1 | 9/2000 | | |
| WO | 00/53559 A1 | 9/2000 | | |
| WO | 02/00587 A1 | 1/2002 | | |
| WO | 02/24620 A2 | 3/2002 | | |
| WO | 03/68721 A1 | 8/2003 | | |
| WO | 2004/007404 A1 | 1/2004 | | |
| WO | 2004/007405 A1 | 1/2004 | | |
| WO | 2004/085363 A1 | 10/2004 | | |
| WO | 2004/085365 A2 | 10/2004 | | |
| WO | 2004/085367 A1 | 10/2004 | | |
| WO | 2004/085368 A2 | 10/2004 | | |
| WO | 2004/085369 A1 | 10/2004 | | |
| WO | 2004/108267 A1 | 12/2004 | | |
| WO | 2004/108284 A1 | 12/2004 | | |
| WO | 2005/030380 A2 | 4/2005 | | |
| WO | 2005/030393 A1 | 4/2005 | | |
| WO | 2005/047224 A1 | 5/2005 | | |
| WO | 2005/047226 A1 | 5/2005 | | |
| WO | 2005/049200 A1 | 6/2005 | | |
| WO | 2005/095315 A2 | 10/2005 | | |
| WO | 2007/017431 A1 | 2/2007 | | |
| WO | 2007/071737 A1 | 6/2007 | | |
| WO | 2007/082827 A1 | 7/2007 | | |
| WO | 2008/087116 A1 | 7/2008 | | |
| WO | 2008/090190 A1 | 7/2008 | | |
| WO | 2009/000494 A2 | 12/2008 | | |
| WO | 2009/078898 A1 | 6/2009 | | |
| WO | 2009/078899 A1 | 6/2009 | | |
| WO | 2010/000764 A2 | 1/2010 | | |
| WO | 2010/028977 A1 | 3/2010 | | |
| WO | 2010/028991 A1 | 3/2010 | | |
| WO | 2010/066645 A2 | 6/2010 | | |
| WO | 2010/067945 A1 | 6/2010 | | |
| WO | 2011/000808 A2 | 1/2011 | | |
| WO | 2011/134932 A1 | 11/2011 | | |
| WO | 2012/049246 A2 | 4/2012 | | |
| WO | 2013/007736 A1 | 1/2013 | | |
| WO | 2013/167405 A1 | 11/2013 | | |
| WO | 2014/122044 A1 | 8/2014 | | |
| WO | 2015/039982 A1 | 3/2015 | | |
| WO | 2015/067659 A1 | 5/2015 | | |
| WO | 2015/104397 A1 | 7/2015 | | |
| WO | 2015/128356 A1 | 9/2015 | | |
| WO | 2015/135968 A1 | 9/2015 | | |
| WO | 2015/145311 A1 | 10/2015 | | |
| WO | 2017/108878 A1 | 6/2017 | | |
| WO | 2018/029215 A1 | 2/2018 | | |
| WO | 2018/210720 A1 | 11/2018 | | |

OTHER PUBLICATIONS

International Search Report and Written Opinion received for PCT Patent Application No. PCT/EP2020/069894, mailed on Oct. 6, 2020, 7 pages.
European Search Report for EP Patent Application No. 19188112.7, Issued on Feb. 21, 2020, 3 pages.
International Preliminary Report on Patentability received for PCT Patent Application No. PCT/EP2020/069894, mailed on Feb. 3, 2022, 10 pages.

* cited by examiner

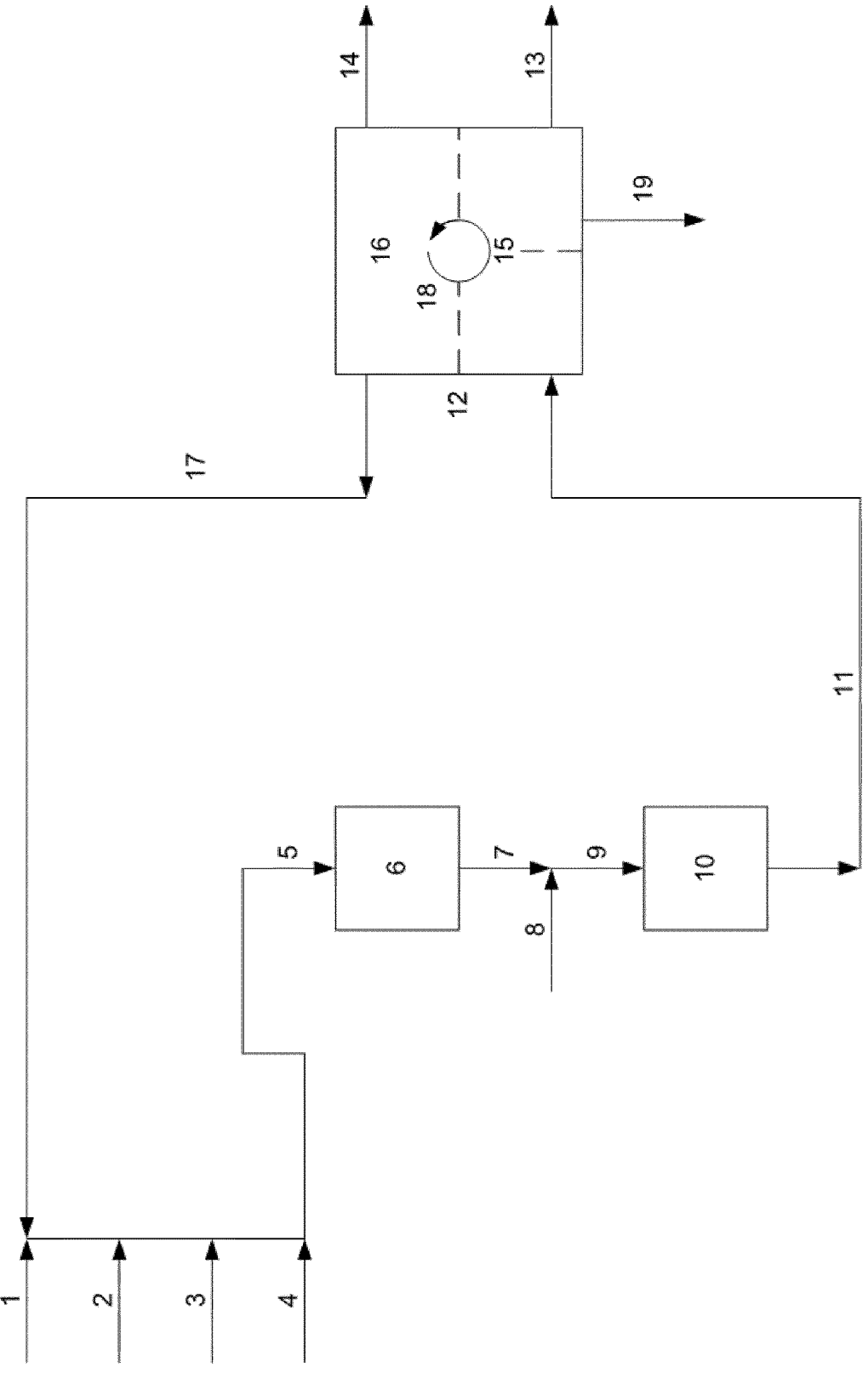

PROCESS FOR THE CONTINUOUS PRODUCTION OF EITHER ACROLEIN OR ACRYLIC ACID AS THE TARGET PRODUCT FROM PROPENE

CROSS-REFERENCE TO RELATED APPLICATIONS

This application is a national stage application (under 35 U.S.C. § 371) of, PCT/EP2020/069894 filed Jul. 14, 2020, which claims benefit of European Application No. 19188112.7, filed Jul. 24, 2019, both of which are incorporated herein by reference in their entirety.

The present invention relates to a process for the continuous production of either acrolein or acrylic acid as the target product from propene comprising under stationary operating conditions A) as an obligatory measure continuously passing in a first reaction stage a stream of a starting reaction gas mixture 1 consisting of from 2 to 15% by volume of propene, from 2.4 to 37.5% by volume of molecular oxygen, from 0.5 to 20% by volume of water, from 0 to 20% by volume of molecular nitrogen, from 0.5 to 30% by volume of carbon monoxide, from 1 to 65% by volume of carbon dioxide, from 0 to 80% by volume of one or more than one hydrocarbon selected from the group consisting of methane, ethane, propane, n-butane, isobutane and ethene, and from >0 to 5% by volume of other compounds including but not limited to acrolein and/or acrylic acid, and containing the molecular oxygen and the propene in a molar $O_2$:propene ratio ranging from 1.2 to 2.5, the carbon dioxide and the carbon monoxide in a molar $CO_2$:CO ratio ranging from 1 to 4, and the molecular oxygen and the molecular nitrogen in a molar $O_2$:$N_2$ ratio of at least 0.5, at a reaction temperature of from 250° C. to 500° C. and a working pressure of from 1 bar to 6 bar through a first fixed catalyst bed comprising shaped catalyst bodies whose active mass is at least one multimetal oxide containing molybdenum (Mo), bismuth (Bi) and iron (Fe) in such a way, that the propene conversion on single pass is from 80 mol % to 99 mol % and the accompanying selectivity $S^A$ of the formation of the target product acrolein is from 70 mol % to 99 mol % to obtain a stream of a the target product acrolein containing product gas mixture 1 leaving the first reaction stage, and, B) in case of acrylic acid being the target product, optionally reducing the temperature of the product gas mixture leaving the first reaction stage by direct, indirect or direct and indirect cooling, optionally adding secondary gas to said product gas mixture in the form of molecular oxygen, or inert gas, or molecular oxygen and inert gas, and subsequently continuously passing in a second reaction stage a stream of the thus resulting starting reaction gas mixture 2 consisting of from 2 to 15% by volume of acrolein, from 1 to 45% by volume of molecular oxygen, from 2 to 30% by volume of water, from 0 to 20% by volume of molecular nitrogen, from 0.5 to 30% by volume of carbon monoxide, from 1 to 65% by volume of carbon dioxide, from 0 to 80% by volume of one or more than one hydrocarbon selected from the group consisting of methane, ethane, propane, n-butane, isobutane and ethene, and from >0 to 5% by volume of other compounds including but not limited to propene and/or acrylic acid, and containing the molecular oxygen and the acrolein in a molar $O_2$:acrolein ratio ranging from 0.5 to 3, the carbon dioxide and the carbon monoxide in a molar $CO_2$:CO ratio ranging from 1 to 4, and the molecular oxygen and the molecular nitrogen in a molar $O_2$:$N_2$ ratio of at least 0.25, at a reaction temperature of from 200° C. to 450° C. and a working pressure of from 1 bar to 6 bar through a second fixed catalyst bed comprising shaped catalyst bodies whose active mass is at least one multimetal oxide containing molybdenum (Mo) and vanadium (V) in such a way, that the acrolein conversion on single pass is from 95 mol % to 99.99 mol % and the accompanying selectivity $S^{AA}$ of the formation of the target product acrylic acid assessed over both reaction stages and based on converted propene is from 80 mol % to 99.9 mol % to obtain a stream of a the target product acrylic acid containing product gas mixture 2 leaving the second reaction stage, and C) either continuously transporting the stream of the target product acrolein containing product gas mixture 1 or the stream of the target product acrylic acid containing product gas mixture 2 into a separating zone and separating in the separating zone the respective target product from the respective product gas mixture through transferring at least 95 mol % of the respective target product contained in the respective product gas mixture from the gaseous phase into the liquid phase and continuously conducting out of the separating zone a total mass flow M of a residual gas mixture R which contains, of the total molar amount of those compounds contained in the product gas mixture continuously transported into the separating zone, which have as pure compounds at a working pressure of 1 bar a boiling point (herein the term boiling point shall also include "or sublimation point") below 250 K, at least 95 mol % and

D) recycling as gaseous stream P having the same composition as the residual gas mixture R a partial stream of the total mass flow M of residual gas mixture R continuously conducted out of the separating zone into the first reaction stage 1 as feed stream for preparing the stream of the starting reaction gas mixture 1 which shall contain the gaseous stream P, and discharging of the production process as off-gas stream O, having the same composition as the residual gas mixture R, the difference between the total mass flow M of residual gas mixture R continuously conducted out of the separating zone and the mass flow of recycle gaseous stream P.

In this document, continuous operation/production means, that starting reaction gas mixture 1 is fed continuously to the first reaction stage over a relatively long period, as a rule more than one day, preferably at least a few (at least 2, or 3, or 4, or 5) days, without interruption and target product in its desired purity is removed continuously from the separating zone.

Acrolein is an important intermediate, for example for the preparation of glutaraldehyde, methionine, 1,3-propanediol, 3-picoline, folic acid and acrylic acid.

Acrylic acid is an important commodity chemical which finds use, inter alia, as a monomer for preparing polymers which are used as binders, for example in disperse distribution in aqueous medium. A further field of use of acrylic acid polymers is that of superabsorbents in the hygiene sector and other fields of application.

It is generally known that acrylic acid can be produced particularly selectively by heterogeneously catalyzed gasphase partial oxidation of propene using molecular oxygen over catalysts which are present in a solid aggregate state. The active masses of the catalysts used are normally oxide compositions. Apart from oxygen they usually contain more than one other element (multielement oxide compositions). Particularly frequently the catalytically active oxide compositions used are those comprising more than one metallic (in particular transition metal) element. These are referred to as multimetal oxide compositions. The multielement oxide compositions are usually not simple physical mixtures of oxides of the elemental constituents, but heterogeneous mixtures of complex poly-compounds of these elements.

As is generally known to those skilled in the art, gasphase partial oxidation of propene to acrylic acid proceeds essentially in two steps in succession along the reaction coordinate, of which the first leads to acrolein and the second from acrolein to acrylic acid. As a result, if a process is suitable for production of acrylic acid from propene by heterogeneously catalyzed gas-phase partial oxidation, it is automatically also suitable for the preparation of acrolein from propene, since the production of acrylic acid can at any time be stopped at the acrolein stage.

Furthermore, the fact that the reaction proceeds in two temporally successive steps makes it possible, in a manner known per se, to carry out the production of acrylic acid from propene by heterogeneous-catalytic gas-phase partial oxidation in two successive oxidation stages, with the oxidic catalyst used in each of the two oxidation stages being able to be optimally matched. Thus, for the first oxidation stage (propene→acrolein), preference is generally given to catalysts based on multimetal oxides containing the element combination Mo—Bi—Fe, while for the second oxidation stage (acrolein→acrylic acid) preference is normally given to catalysts based on multimetal oxides containing the element combination Mo—V. Appropriate multimetal oxide catalysts for the two oxidation stages have been described many times and are well known to those skilled in the art (cf., for example EP-1005908, WO 00/53559, WO 00/53556, WO 00/53557, WO 02/24620, WO 2004/085368, WO 2004/085367, WO 2004/085365, WO 2004/085363, WO 2004/108284, WO 2004/108267, WO 2005/030393, WO 2005/047226, WO 2005/047224, WO 2005/049200, WO 2007/082827, WO 2008/087116, WO 2010/000764, WO 2010/028977, WO 2010/028991, WO 2010/066645, WO 2011/134932, WO 2012/049246, WO 2013/007736, WO 2013/167405, WO 2015/039982, WO 2015/067659, WO 2015/0128356 and DE-102018200841).

Usually the multimetal oxide active compositions are not applied in powder form but shaped to certain catalyst geometries. For example, unsupported catalysts can be prepared from the powder of the active composition or its uncalcined and/or partially calcined precursor composition (in the latter two cases final calcination is carried out after shaping) by compacting to the desired catalyst geometry (for example by tableting or extruding), optionally with the addition of assistants, for example graphite, hexagonal boron nitride or stearic acid as lubricants and/or shaping assistants and reinforcing agents such as microfibers of glass, asbestos, silicon carbide or potassium titanate. Examples of suitable unsupported catalyst geometries include solid cylinders or hollow cylinders as well as spheres.

The pulverulent active composition or its pulverulent precursor composition which is yet to be calcined and/or partially calcined may of course also be shaped by applying to pre-shaped inert catalyst supports. The coating of the support bodies to produce the coated catalyst is generally performed in a suitable rotatable vessel, as disclosed, for example, by DE-A 2909671, EP-A 293859 or EP-A 714700. To coat the support bodies, the powder composition to be applied is appropriately moistened and dried again after application, for example by means of hot air (and subsequently calcined in case of e.g. coating with pulverulent precursor composition which is yet to be calcined). Alternatively, pulverulent active composition or its pulverulent precursor composition advantageously can also be coated onto shaped support bodies (carriers) in a fluidized bed process as exemplarily described in WO 2005/030380. Useful support materials are materials which substantially behave inert regarding both the respective target reaction on which the production process is based and side reactions that accompany the target reaction (cf., for example porous or non-porous aluminium oxides, silicon dioxide, thorium dioxide, zirconium dioxide, silicon carbide or silicates such as magnesium silicate or aluminium silicate). As the unsupported catalyst geometries, the support bodies can have a regular or irregular shape, although preference is given to regularly shaped support bodies having distinct surface roughness, for example spheres, solid or hollow cylinders.

In general, the heterogeneously catalyzed gas-phase partial oxidation of propene to acrolein as well as of acrolein to acrylic acid is carried out at elevated reaction temperature (normally a few hundred ° C., typically from 250° C. to 500° C. in case of propene to acrolein, and 200° C. to 450° C. in case of acrolein to acrylic acid). The working pressure (absolute pressure) is normally in both cases in the range from 1 bar to 6 bar.

The relevant shaped catalyst bodies are usually part of a fixed catalyst bed through which the relevant reaction gas mixture containing the reactants molecular oxygen and propene or molecular oxygen and acrolein pass through at the relevant reaction temperature and working pressure. The target reaction occurs during the residence time of the reaction mixture in the fixed catalyst bed through which it is passed. In the propene to acrolein stage the propene conversion on single pass is typically from 80 mol % to 99 mol % and the accompanying selectivity $S^A$ of the formation of the target product acrolein is typically from 70 mol % to 99 mol %. In the acrolein to acrylic acid stage the acrolein conversion on single pass is typically from 95 mol % to 99.99 mol % and the accompanying selectivity $S^{AA}$ of the formation of the target product acrylic acid assessed over both reaction stages and based on converted propene is from 80 mol % to 99.9 mol %.

The simplest implementation form of a relevant reaction (oxidation) stage therefore comprises a tube-bundle reactor in the contact tubes (reaction tubes) of which the relevant fixed catalyst bed is charged. For purposes of control of the reaction temperature within the reaction tubes technologically advantageously a fluid (e.g. liquid) heat exchange medium (e.g. a salt melt) is passed through the space surrounding the contact tubes (cf., for example EP-A 700714 and EP-A 700983). As an alternative, a thermoplate reactor in which the fixed catalyst bed is present as a flat arrangement between cooling plates can also be used (cf., for example, US-A 2005/0042154 and US-A 2005/0020851).

Similarly, the two oxidation stages can be implemented in the form of an oxidation reactor system comprising two oxidation reactors in series and optionally a heat exchanger between the two reactors for cooling the reaction gas mixture leaving the first reactor if desired. Using this arrangement, the other reaction conditions (e.g. reaction temperatures) can be optimally matched in a simple manner in the respective oxidation stage. In principle, foresaid set up enables to transfer the product gas mixture of the first oxidation stage without any intermediate treatment to the second oxidation stage. However, the molecular oxygen required for the second oxidation stage is here advantageously fed only to the second oxidation reactor. In an alternative embodiment the heterogeneously catalyzed gas-phase partial oxidation of propylene to acrylic acid can also be carried out in a single reactor. In this case, both reaction steps e.g. may occur in one oxidation reactor loaded with a catalyst charge which changes abruptly along the reaction coordinate.

All possible design variants have in common, that, owing to the pronounced exothermic character of the partial oxidation of propene or acrolein, the oxidation reactors are customarily fed with a starting reaction gas mixture which contains the reactants molecular oxygen and propene or molecular oxygen and acrolein diluted with a gas which is essentially inert under the conditions of the respective gas-phase partial oxidation. Here, inert diluent gases are those, whose constituents (components) remain unaltered to an extent of more than 95 mol %, preferably more than 98 mol %, under the conditions of the heterogeneously catalyzed gas-phase partial oxidation on single pass through the respective reaction stage. Usually the inert diluent gas comprises the major proportion by volume of the respective starting reaction gas mixture (feed reaction gas mixture). The effect of inert diluent gases is primarily based on simple dilution of the reactants and their ability to absorb reaction heat. Examples for possible inert diluent gases are hydrocarbons selected from the group consisting of methane, ethane, propane, n-butane, isobutane and ethene, water ($H_2O$), molecular nitrogen ($N_2$), carbon oxides (CO, $CO_2$) and any mixture of some or all aforementioned gases. Inert diluent gases having as pure compounds at a working pressure of 1 bar a boiling point below 250 K are preferred.

Regarding the stoichiometry of the respective partial oxidation step to give the desired target compound it is generally necessary to use the molecular oxygen used as oxidant in the respective fed reaction gas mixture in at least stoichiometric or in superstoichiometric amounts (e.g. to reoxidize the multimetal oxide active composition of the catalyst applied and to reduce carbon deposits on the surface of the catalyst).

The separation of the respective target product (acrolein or acrylic acid) from the respective product gas mixture resulting in the respective heterogeneously catalyzed partial gas phase oxidation is usually carried out in a corresponding separating zone through transferring at least 95 mol % of the respective target product contained in the respective product gas mixture from the gaseous phase into the liquid phase. This can be done as known from the prior art processes.

In general, the respective product gas mixture on entry into the separating zone will initially be subjected to indirect and/or direct cooling (such cooling can already cause a separation of constituents of the target product containing product gas mixture continuously transported into the separating zone, which have as pure compounds at a working pressure of 1 bar a boiling point above the boiling point of the target product, from said product gas mixture). Transferring the target product present in the product gas mixture which has been cooled in this way or present in uncooled product gas mixture into the liquid phase can be carried out by absorption into a liquid absorbent and/or by condensation (e.g. fractional condensation) as described, for example, in U.S. Pat. No. 3,433,840, WO 2008/090190, WO 2011/000808, U.S. Pat. No. 7,183,428, WO 2014/122044, U.S. Pat. No. 5,315,037, WO 2003/068721, DE-A 10213998, and DE-A 3429391. Useful absorbents for substantially both target products are either water or aqueous solutions, or high boiling organic solvents. Subsequent workup of the resulting, the desired target product containing, liquid phase in the separating zone through application of thermal separation processes such as stripping, distillation, rectification (including azeotropic rectification respectively distillation), extraction and/or crystallization finally yields the target product in its desired purity which normally is continuously withdrawn from the separation zone into which the product mixture is also continuously fed.

Those constituents of the target product containing product gas mixture continuously transported into the separating zone which have as pure compounds at a working pressure of 1 bar a boiling point below the boiling point of pure water remain in the separating zone mainly in the gaseous phase (in case of water itself and of constituents having under corresponding conditions a boiling point above that of pure water, the specific working conditions applied for transferring the target product from the respective product gas mixture into the liquid phase determine the respective amount that remains of these constituents and water in the residual gas mixture) and are contained in a residual gas mixture of which a total mass flow is continuously conducted out of the separating zone. Especially those compounds contained in the product gas mixture continuously transported into the separating zone, which have as pure compounds at a working pressure of 1 bar a boiling point below 250 K (such compounds above all include the respective components of the inert diluent gas applied), are a major portion of the residual gas mixture. Typically, at least 95 mol % of the total molar amount of those compounds being components of the product gas mixture continuously transported into the separating zone and having as pure compounds at a working pressure of 1 bar a boiling point below 250 K are (under stationary operating conditions) finally contained in the total mass stream of the residual gas mixture continuously conducted out of the separating zone.

Normally, said residual gas mixture still contains remaining unconverted propene. As propene is a valuable raw material of the production process and due to above explanations, there is a natural interest to recycle the total mass flow of the residual gas mixture continuously conducted out of the separating zone into the propene to acrolein reaction stage as feed charge for preparing the starting reaction gas mixture fed into said reaction stage. This would on the one hand help to increase both the overall ("on multiple pass") propene conversion and the resulting yield of the target product (e.g. acrylic acid) of the production process and on the other hand provide a suitable source of inert diluent gas usable for preparing said starting reaction gas mixture.

However, a complete recirculation of the relevant total mass flow of the residual gas mixture continuously conducted out of the separating zone as feed for the relevant starting reaction gas mixture would not be feasible. This is because to prevent accumulation of certain components of the residual gas mixture in the production process which for example are continuously by-produced in a reaction stage (for example CO, $CO_2$ or $H_2O$) or otherwise continuously introduced into the production process (e.g. molecular nitrogen ($N_2$) optionally contained as a companion of molecular oxygen ($O_2$) in the source of fresh molecular oxygen (e.g. air) used for the preparation of the respective starting gas mixture continuously fed into the respective reaction stage), under stationary operating conditions at least a balancing portion of the total mass stream of the residual gas mixture continuously conducted out of the separating zone has to be continuously discharged of (from) the production process as off-gas. Technologically advantageously the off-gas has the same composition as the residual gas mixture and only the difference between the total mass flow of the residual gas mixture continuously conducted out of the separating zone and the mass flow of the off-gas stream continuously discharged of the production process is recirculated (returned as a circular gas flow) as feed stream, which consequently also has the same composition as the residual gas mixture, for preparing the stream of the relevant starting reaction gas mixture.

For the majority of processes recommended according to the prior art for producing either acrolein or acrylic acid as the target product by heterogeneously catalyzed gas-phase partial oxidation of propene the feed gas streams used for preparing the stream of the starting reaction gas mixture fed into the propene to acrolein reaction stage consist of a stream of ambient air (based on its total volume comprising about 78% by volume $N_2$ and about 21% by volume $O_2$), a stream of chemical grade propene (consisting of about 95% by volume propene and about 5% by volume propane) and the stream of the recirculated portion of the residual gas mixture resulting in the process. Consequently, the mass flow of the off-gas stream in case of these processes as a rule is 38% or more of the total mass flow of residual gas mixture continuously conducted out of the separating zone (cf., for example WO 2008/090190 or WO 2011/000808). Since the molecular nitrogen ($N_2$) content of the off-gas in aforesaid production processes in addition is normally 85% by volume or more, such off-gas mainly due to economic reasons is usually not further used as a raw material for another synthesis but just disposed of through combustion (cf. WO 97/48669) in order at least to benefit from the resulting combustion energy. A disadvantage of this procedure is that, in addition to carbon dioxide already contained in the off-gas before its combustion, combustion of carbon containing constituents of the off-gas produces additional carbon dioxide whose outlet into the ambient air makes the carbon dioxide footprint of the process for producing either acrolein or acrylic acid as the target product from propene worse.

EP-A 731080 is directed, inter alia, to a process for the continuous heterogeneously catalyzed gas phase partial oxidation of propene in an oxidation reactor to yield as target product either acrolein or acrylic acid. In the EP-A 731080 production process the starting reaction gas mixture fed to the oxidation reactor consists apart from propene and molecular oxygen of an inert diluent gas preferably consisting of more than 85% by volume and best of 100% by volume of a combustible saturated hydrocarbon (other than in case of the WO 2008/090190 or WO 2011/000808 process the molecular oxygen required for such EP-A 731080 process is taken from an essentially pure molecular oxygen source. After one passage of the reaction gas mixture through the oxidation reactor according to the teaching of EP-A 731080 the aforesaid combustible constituents of the inert diluent gas present in the production gas stream leaving the oxidation reactor are not at all recirculated into the heterogeneously gas-phase partial oxidation but (preferably directly) further used for production of synthesis gas (one disadvantage of such procedure is that the total amount of saturated hydrocarbon introduced into the starting reaction gas mixture via an independent feed stream is only used in a single pass as inert diluent gas). In case residual gas mixture continuously conducted out of the separating zone is fed as such to such further use this would improve the carbon dioxide footprint of the EP-A 731080 process over the carbon dioxide footprint of the WO 2011/000808 respectively WO 2008/090190 process, however, in such case unconverted propene still contained in said residual gas mixture also is not recirculated to the oxidation reactor which disadvantageously would abate both the overall propene conversion and the resulting yield of the target product (e.g. acrylic acid) of the production process. If alternatively, unreacted propene still contained in said residual gas mixture would be separated off beforehand the relevant further use and separately recirculated to the oxidation reactor to increase the propene overall conversion, this would require additional efforts and disadvantageously appreciably reduce the efficiency of the EP-A 731080 production process. The hint additionally given in EP-A 731080, that optionally none-combustible inert diluent gas constituents (including those which are only formed as by-products in the course of the reaction) such as $N_2$, $CO_2$ and $H_2O$ also could be separated off beforehand the relevant further use and be discharged into the atmosphere neither would be efficient nor helpful regarding the target of improving the carbon dioxide footprint of the process.

U.S. Pat. No. 5,684,188 is directed to a process for the continuous heterogeneously catalyzed gas-phase partial oxidation of propene to acrolein, acrylic acid or a mixture thereof in an oxidation reactor whose starting reaction gas (feed gas) mixture comprises, apart from propene and molecular oxygen as oxidant, only at least one diluent gas which is essentially inert under the conditions of the heterogeneously catalyzed gas-phase oxidation, where, in continuous operation, at least a part of the essentially inert diluent gas constituents present in the product gas mixture is separated off therefrom and is reused as a constituent of the feed to the oxidation reactor, wherein the essentially inert diluent gas mixture of the feed gas mixture in continuous operation comprises more than 85% by volume, preferably at least 99% by volume and best 100% by volume of at least one saturated hydrocarbon having from 1 to 5 carbon atoms.

A very particular aspect of the teaching of U.S. Pat. No. 5,684,188 however is, that the saturated hydrocarbons used as inert diluent gas constituents of the starting reaction gas mixture are, unlike inert diluent gas constituents such as $N_2$, $H_2O$ and $CO_2$, considered materials of value. Therefore, according to U.S. Pat. No. 5,684,188 a prerequisite for an economical operation of its process is the recycling of saturated hydrocarbon present in the product gas mixture as feed for the starting reaction gas mixture. Consequently, from the point of view of U.S. Pat. No. 5,684,188 for the purpose of this recirculation the saturated hydrocarbons have to be separated not only from the target product in the product gas mixture, but also from by-product gases such as $CO_2$ and $H_2O$. Additionally, according to U.S. Pat. No. 5,684,188 unreacted starting material (propene) and/or intermediate (acrolein) still present in the product gas mixture can also be separated and recirculated to the oxidation reactor as feed for the preparation of the starting reaction gas mixture. Such separating hydrocarbons from the other constituents of the product gas mixture however disadvantageously reduces the economic efficiency of the process.

It therefore is an object of the present invention to provide a process for the continuous production of either acrolein or acrylic acid as the target product by heterogeneously catalyzed gas-phase partial oxidation of propene and subsequent separating the target product from the respective product gas mixture in a separating zone through transferring it from the product gas mixture into the liquid phase, whose off-gas has a generation and composition which, other than in case of the processes of U.S. Pat. No. 5,684,188, WO 2008/090190, WO 2011/000808 and EP-A 731080, enables, if so desired to improve the carbon dioxide balance of the process, its (preferably direct) further using as raw material for the production of synthesis gas (also "syngas") and/or as addition into synthesis gas already produced without causing/involving significant economic disadvantages regarding its generation and/or using.

It is another object of the present invention to provide a process that additionally enables both high overall propene conversions and high resulting yields of target product (e.g. acrylic acid).

It is a further object of this invention to provide a process that in preferred embodiments is carried out outside the explosive range.

We have found that all these objects are achieved by a process for the continuous production of either acrolein or acrylic acid as the target product from propene comprising under stationary operating conditions A) as an obligatory measure continuously passing in a first reaction stage a stream of a starting reaction gas mixture 1 consisting of from 2 to 15% by volume of propene, from 2.4 to 37.5% by volume of molecular oxygen, from 0.5 to 20% by volume of water, from 0 to 20% (preferably 0 to 10%) by volume of molecular nitrogen, from 0.5 to 30% by volume of carbon monoxide, from 1 to 65% by volume of carbon dioxide, from 0 to 80% by volume of one or more than one hydrocarbon selected from the group consisting of methane, ethane, propane, n-butane, isobutane and ethene, and from >0 to 5% by volume of other compounds including but not limited to acrolein and/or acrylic acid, and containing the molecular oxygen and the propene in a molar $O_2$:propene ratio ranging from 1.2 to 2.5, the carbon dioxide and the carbon monoxide in a molar $CO_2$:CO ratio ranging from 1 to 4, and the molecular oxygen and the molecular nitrogen in a molar $O_2$:$N_2$ ratio of at least 0.5, at a reaction temperature of from 250° C. to 500° C. and a working pressure of from 1 bar to 6 bar through a first fixed catalyst bed comprising shaped catalyst bodies whose active mass is at least one multimetal oxide containing molybdenum (Mo), bismuth (Bi) and iron (Fe) in such a way, that the propene conversion on single pass is from 80 mol % to 99 mol % and the accompanying selectivity $S^A$ of the formation of the target product acrolein is from 70 mol % to 99 mol % to obtain a stream of a the target product acrolein containing product gas mixture 1 leaving the first reaction stage, and, B) in case of acrylic acid being the target product, optionally reducing the temperature of the product gas mixture leaving the first reaction stage by direct, indirect or direct and indirect cooling, optionally adding secondary gas to said product gas mixture in the form of molecular oxygen, or inert gas, or molecular oxygen and inert gas, and subsequently continuously passing in a second reaction stage a stream of the thus resulting starting reaction gas mixture 2 consisting of from 2 to 15% by volume of acrolein, from 1 to 45% by volume of molecular oxygen, from 2 to 30% by volume of water, from 0 to 20% (preferably 0 to 10%) by volume of molecular nitrogen, from 0.5 to 30% by volume of carbon monoxide, from 1 to 65% by volume of carbon dioxide, from 0 to 80% by volume of one or more than one hydrocarbon selected from the group consisting of methane, ethane, propane, n-butane, isobutane and ethene, and from >0 to 5% by volume of other compounds including but not limited to propene and/or acrylic acid, and containing the molecular oxygen and the acrolein in a molar $O_2$:acrolein ratio ranging from 0.5 to 3, the carbon dioxide and the carbon monoxide in a molar $CO_2$:CO ratio ranging from 1 to 4, and the molecular oxygen and the molecular nitrogen in a molar $O_2$:$N_2$ ratio of at least 0.25, at a reaction temperature of from 200° C. to 450° C. and a working pressure of from 1 bar to 6 bar through a second fixed catalyst bed comprising shaped catalyst bodies whose active mass is at least one multimetal oxide containing molybdenum (Mo) and vanadium (V) in such a way, that the acrolein conversion on single pass is from 95 mol % to 99.99 mol % and the accompanying selectivity $S^{AA}$ of the formation of the target product acrylic acid assessed over both reaction stages and based on converted propene is from 80 mol % to 99.9 mol % to obtain a stream of a the target product acrylic acid containing product gas mixture 2 leaving the second reaction stage, and C) either continuously transporting the stream of the target product acrolein containing product gas mixture 1 or the stream of the target product acrylic acid containing product gas mixture 2 into a separating zone and separating in the separating zone the respective target product from the respective product gas mixture through transferring at least 95 mol % of the respective target product contained in the respective product gas mixture from the gaseous phase into the liquid phase and continuously conducting out of the separating zone a total mass flow M of a residual gas mixture R which contains, of the total molar amount of those compounds contained in the product gas mixture continuously transported into the separating zone, which have as pure compounds at a working pressure of 1 bar a boiling point below 250 K, at least 95 mol % (preferably at least 96 mol %, especially preferred at least 97 mol % and best at least 98 mol %, or at least 99 mol %, or at least 99.5 mol % but normally less than 100 mol %)

and

D) recycling as gaseous stream P having the same composition as the residual gas mixture R a partial stream of the total mass flow M of residual gas mixture R continuously conducted out of the separating zone into the first reaction stage 1 as feed stream for preparing the stream of the starting reaction gas mixture 1 which shall contain the gaseous stream P, and discharging of the production process as off-gas stream O, having the same composition as the residual gas mixture R, the difference between the total mass flow M of residual gas mixture R continuously conducted out of the separating zone and the mass flow of recycle gaseous stream P, wherein a) the mass flow of the recycle gaseous stream P is at least 65% but not more than 99.5% of the total mass flow M of residual gas mixture R continuously conducted out of the separating zone, b) the mass flow of the off-gas stream O is not more than 35% but at least 0.5% of the total mass flow M of residual gas mixture R continuously conducted out of the separating zone, and c) the composition C of the residual gas mixture R is from 0.01 to 1% by volume of propene, from 1 to 10% by volume of molecular oxygen, from 0.5 to 25% by volume of water, from 0 to 20% (preferably 0 to 10%) by volume of molecular nitrogen, from 0.5 to 40% by volume of carbon monoxide, from 1 to 75% by volume of carbon dioxide, from 0 to 92% by volume of one or more than one hydrocarbon selected from the group consisting of methane, ethane, propane, n-butane, isobutane and ethene, and from 0.01 to 5% by volume of other compounds including but not limited to acrolein and/or acrylic acid.

Advantageous according to the invention the reaction temperature in the first reaction stage is 280° C. to 480° C., preferably 290° C. to 470° C. and more preferably 300° C. to 450° C. The working pressure in the first reaction stage of the inventive process is preferably from 1 to 5 bar, more preferably from 1 to 4 bar and most preferably from 1 to 3.5 bar. It is favorable when the propene conversion on single pass in the first reaction stage of the inventive process is in the range from 85 mol % to 99 mol %. Better said conversion is from 90 mol % to 99 mol % and the best said conversion is from 92 mol % to 98.5 mol %. The accompanying selectivity $S^A$ of the formation of the target product acrolein in the first reaction stage is advantageously from 75 mol % to 99 mol % and better from 80 mol % to 99 mol %.

Advantageous according to the invention the reaction temperature in the second reaction stage is 210° C. to 430° C., preferably 220° C. to 410° C. and more preferably 230° C. to 390° C. The working pressure in the second reaction stage of the inventive process is preferably from 1 to 5 bar, more preferably from 1 to 4 bar and most preferably from 1 to 3.5 bar. It is favorable when the acrolein conversion on single pass in the second reaction stage of the inventive process is in the range from 97 mol % to 99.95 mol %. Better said conversion is from 98 mol % to 99.9 mol % and the best said conversion is from 99 mol % to 99.8 mol %. The accompanying selectivity $S^{AA}$ of the formation of the target product acrylic acid assessed over both reaction stages and based on converted propene is advantageously from 83 mol % to 99 mol %, better from 85 mol % to 99 mol % and the best from 87 mol % to 99 mol %.

Due to the envisaged subsequent optional use of the off-gas of the inventive process for production of synthesis gas, ambient air is not suitable as source of the molecular oxygen required as oxidant for the purposes (such as preparing (forming, generating) starting reaction gas mixture 1) of the inventive process (including the optional addition of a molecular oxygen containing secondary gas to the product gas mixture 1 between the first reaction stage and the second reaction stage of the inventive process for preparing starting reaction gas mixture 2) because of its high molecular nitrogen content. In contrast, mixtures of molecular oxygen and inert gas containing at least 90% by vol., preferably at least 95% by vol., more preferably at least 98% by vol., even better at least 99% by vol. and best from 99.4% by vol. to 99.9% by vol. or from 99.5% by vol. to 99.8% by vol. of molecular oxygen are suitable as such oxygen sources for aforesaid purposes. Air depleted of molecular nitrogen are such mixtures (compared to using ambient air as an oxygen source, a using of molecular oxygen of a purity of at least 90% by vol. $O_2$ and of not more than 10% by vol. $N_2$ also has the advantage, that the quality of the oxygen source is decoupled from and no longer affected by undesirable environmental influences at the respective production site (e.g. no corrosive damage due to chloride content in the ambient air; in addition, the compressor required for compressing ambient air to working pressure can be omitted)). Accordingly, (molecular) oxygen of a purity of at least 90% by vol. $O_2$ and of not more than 10% by vol. $N_2$, or of at least 95% by vol. $O_2$ and of not more than 5% by vol. $N_2$, or of at least 98% by vol. $O_2$ and of not more than 2% by vol. $N_2$, or of at least 99% by vol. $O_2$ and of not more than 1% by vol. $N_2$, or of from 99.4% by vol. to 99.9% by vol. $O_2$ and of from 0.1% by vol. to 0.6% by vol. $N_2$, or of from 99.5% by vol. to 99.8% by vol. $O_2$ and of from 0.2% by vol. to 0.5% by vol. $N_2$, are suitable as such oxygen sources.

Of course, pure molecular oxygen (with a purity of 100% by vol. $O_2$) can also be used as an advantageous oxygen source for the inventive process.

As possible sources of the starting material propene (propene source, raw propene, propene feedstock) used to prepare starting reaction gas mixture 1 polymer grade propene (containing ≥99% by vol. propene and ≤1% by vol. propane), chemical grade propene (containing ≥90% by vol. propene and ≤10% by vol. but 2% by vol. propane) and refinery grade propene (containing ≥70% by vol. propene and 30% by vol. but 15% by vol. propane) can be applied (e.g. those specifically defined in WO 2004/007405). Since part of propane accompanying propene in aforesaid propene sources finally also appears in the off-gas of the inventive process and heterogeneously catalyzed steam reforming of saturated hydrocarbons is a suitable means to produce synthesis gas, chemical grade propene is a very preferred propene source for the inventive process.

Preferably in the inventive process the mass flow of the recycle gaseous stream P is at least 70% but not more than 99.5% of the mass flow M of residual gas mixture R continuously conducted out of the separating zone and the mass flow of the off-gas stream O is not more than 30% but at least 0.5% of the total mass flow M of residual gas mixture R continuously conducted out of the separating zone.

Particularly preferred in the inventive process the mass flow of the recycle gaseous stream P is at least 80% but not more than 99.0% of the mass flow M of residual gas mixture R continuously conducted out of the separating zone and the mass flow of the off-gas stream O is not more than 20% but at least 1.0% of the total mass flow M of residual gas mixture R continuously conducted out of the separating zone.

Even more preferred in the inventive process the mass flow of the recycle gaseous stream P is at least 90% but not more than 99.0% of the mass flow M of residual gas mixture R continuously conducted out of the separating zone and the mass flow of the off-gas stream O is not more than 10% but at least 1.0% of the total mass flow M of residual gas mixture R continuously conducted out of the separating zone.

Most preferred in the inventive process the mass flow of the recycle gaseous stream P is at least 95% but not more than 98.0% of the mass flow M of residual gas mixture R continuously conducted out of the separating zone and the mass flow of the off-gas stream O is not more than 5% but at least 2.0% of the total mass flow M of residual gas mixture R continuously conducted out of the separating zone.

A first highly preferred embodiment of the inventive process is a process for the continuous production of either acrolein or acrylic acid as the target product from propene comprising under stationary operating conditions A) as an obligatory measure continuously passing in a first reaction stage a stream of a starting reaction gas mixture 1 consisting of from 2 to 15% by volume of propene,
from 2.4 to 37.5% by volume of molecular oxygen,
from 0.5 to 10% by volume of water,
from 0 to 10% (preferably 0 to 5%) by volume of molecular nitrogen,
from 15 to 25% by volume of carbon monoxide,
from 20 to 55% by volume of carbon dioxide,
from 10 to 30% by volume of at least one hydrocarbon selected from the group consisting of methane, ethane, propane, n-butane, isobutane and ethene (preferably essentially only propane), and
from >0 to 5% by volume of other compounds including but not limited to acrolein and/or acrylic acid, and containing the molecular oxygen and the propene in a molar $O_2$:propene ratio ranging from 1.2 to 2.5,
the carbon dioxide and the carbon monoxide in a molar $CO_2$:CO ratio ranging from 1 to 4,
and the molecular oxygen and the molecular nitrogen in a molar $O_2$:$N_2$ ratio of at least 0.5, at a reaction temperature of from 250° C. to 500° C. and a working pressure of from 1 bar to 6 bar through a first fixed catalyst bed comprising shaped catalyst bodies whose active mass is at least one multimetal oxide containing molybdenum (Mo), bismuth (Bi) and iron (Fe) in such a way, that the propene conversion on single pass is from 80 mol % to 99 mol % and the accompanying selectivity $S^A$ of the formation of the target product acrolein is from 70 mol % to 99 mol % to obtain a stream of a the target product acrolein containing product gas mixture 1 leaving the first reaction stage,
and, B) in case of acrylic acid being the target product, optionally reducing the temperature of the product gas mixture leaving the first reaction stage by direct, indirect or direct and indirect cooling,
optionally adding secondary gas to said product gas mixture in the form of molecular oxygen, or inert gas, or molecular oxygen and inert gas, and
subsequently continuously passing in a second reaction stage a stream of the thus resulting starting reaction gas mixture 2 consisting of from 2 to 15% by volume of acrolein,
from 1 to 45% by volume of molecular oxygen,
from 2 to 20% by volume of water,
from 0 to 10% (preferably 0 to 5%) by volume of molecular nitrogen,
from 15 to 25% by volume of carbon monoxide,
from 20 to 55% by volume of carbon dioxide,
from 10 to 30% by volume of at least one hydrocarbon selected from the group consisting of methane, ethane, propane, n-butane, isobutane and ethene (preferably essentially only propane), and
from >0 to 5% by volume of other compounds including but not limited to propene and/or acrylic acid, and containing the molecular oxygen and the acrolein in a molar $O_2$:acrolein ratio ranging from 0.5 to 3,
the carbon dioxide and the carbon monoxide in a molar $CO_2$:CO ratio ranging from 1 to 4, and
the molecular oxygen and the molecular nitrogen in a molar $O_2$:$N_2$ ratio of at least 0.25, at a reaction temperature of from 200° C. to 450° C. and a working pressure of from 1 bar to 6 bar through a second fixed catalyst bed comprising shaped catalyst bodies whose active mass is at least one multimetal oxide containing molybdenum (Mo) and vanadium (V) in such a way, that the acrolein conversion on single pass is from 95 mol % to 99.99 mol % and the accompanying selectivity $S^{AA}$ of the formation of the target product acrylic acid assessed over both reaction stages and based on converted propene is from 80 mol % to 99.9 mol % to obtain a stream of a the target product acrylic acid containing product gas mixture 2 leaving the second reaction stage, and C) either continuously transporting the stream of the target product acrolein containing product gas mixture 1 or the stream of the target product acrylic acid containing product gas mixture 2 into a separating zone and separating in the separating zone the respective target product from the respective product gas mixture through transferring at least 95 mol % of the respective target product contained in the respective product gas mixture from the gaseous phase into the liquid phase and continuously conducting out of the separating zone a total mass flow M of a residual gas mixture R which contains, of the total molar amount of those compounds contained in the product gas mixture continuously transported into the separating zone, which have as pure compounds at a working pressure of 1 bar a boiling point below 250 K, at least 95 mol % and D) recycling as gaseous stream P having the same composition as the residual gas mixture R a partial stream of the total mass flow M of residual gas mixture R continuously conducted out of the separating zone into the first reaction stage 1 as feed stream for preparing the stream of the starting reaction gas mixture 1 which shall contain the gaseous stream P, and discharging of the production process as off-gas stream O, having the same composition as the residual gas mixture R, the difference between the total mass flow M of residual gas mixture R continuously conducted out of the separating zone and the mass flow of recycle gaseous stream P,
wherein a) the mass flow of the recycle gaseous stream P is at least 90% but not more than 99% of the total mass flow M of residual gas mixture R continuously conducted out of the separating zone, b) the mass flow of the off-gas stream O is not more than 10% but at least 1% of the total mass flow M of residual gas mixture R continuously conducted out of the separating zone, and c) the composition C of the residual gas mixture R is
from 0.05 to 0.5% by volume of propene,
from 1 to 4% by volume of molecular oxygen,
from 0.5 to 10% by volume of water,
from 0 to 10% (preferably 0 to 5%) by volume of molecular nitrogen,
from 15 to 30% by volume of carbon monoxide,
from 30 to 60% by volume of carbon dioxide,
from 10 to 50% by volume of at least one hydrocarbon selected from the group consisting of methane, ethane, propane, n-butane, isobutane and ethene (preferably essentially only propane), and
from 0.01 to 5% by volume of other compounds including but not limited to acrolein and/or acrylic acid.

In case of the aforesaid first highly preferred embodiment the feed streams forming (used for preparing) starting reaction gas mixture 1 preferably consist only of a feedstock stream of chemical grade propene (propene feedstock containing ≥90% by vol. propene and ≤10% by vol. but ≥2% by vol. propane), a stream of molecular oxygen of the purity ≥99.0% by vol. and ≤99.9% by vol. $O_2$ and ≤1% by vol. and ≥0.1% by vol. $N_2$, and recycle gaseous stream P.

A second highly preferred embodiment of the inventive process is a process for the continuous production of either acrolein or acrylic acid as the target product from propene comprising under stationary operating conditions A) as an obligatory measure continuously passing in a first reaction stage a stream of a starting reaction gas mixture 1 consisting of
from 2 to 15% by volume of propene,
from 2.4 to 37.5% by volume of molecular oxygen,
from 0.5 to 10% by volume of water,
from 0 to 10% (preferably 0 to 5%) by volume of molecular nitrogen,
from 1.2 to 15% by volume of carbon monoxide,
from 3 to 30% by volume of carbon dioxide,
from 40 to 80% by volume of at least one hydrocarbon selected from the group consisting of methane, ethane, propane, n-butane, isobutane and ethene (preferably at least 80 mol % of the total molar amount of these hydrocarbons is methane), and
from >0 to 5% by volume of other compounds including but not limited to acrolein and/or acrylic acid,
and containing
the molecular oxygen and the propene in a molar $O_2$:propene ratio ranging from 1.2 to 2.5,
the carbon dioxide and the carbon monoxide in a molar $CO_2$:CO ratio ranging from 1 to 4,
the molecular oxygen and the molecular nitrogen in a molar $O_2$:$N_2$ ratio of at least 0.5, and
the carbon monoxide and the total molar amount of hydrocarbons in a molar CO:total hydrocarbons ratio ranging from >0 to 0.3,
at a reaction temperature of from 250° C. to 500° C. and a working pressure of from 1 bar to 6 bar through a first fixed catalyst bed comprising shaped catalyst bodies whose active mass is at least one multimetal oxide containing molybdenum (Mo), bismuth (Bi) and iron (Fe) in such a way, that the propene conversion on single pass is from 80 mol % to 99 mol % and the accompanying selectivity $S^A$ of the formation of the target product acrolein is from 70 mol % to 99 mol % to obtain a stream of a the target product acrolein containing product gas mixture 1 leaving the first reaction stage,
and, B) in case of acrylic acid being the target product,
optionally reducing the temperature of the product gas mixture leaving the first reaction stage by direct, indirect or direct and indirect cooling,
optionally adding secondary gas to said product gas mixture in the form of molecular oxygen, or inert gas, or molecular oxygen and inert gas, and
subsequently continuously passing in a second reaction stage a stream of the thus resulting starting reaction gas mixture 2 consisting of
from 2 to 15% by volume of acrolein,
from 1 to 45% by volume of molecular oxygen,
from 2 to 20% by volume of water,
from 0 to 10% (preferably 0 to 5%) by volume of molecular nitrogen,
from 1.2 to 15% by volume of carbon monoxide,
from 3 to 30% by volume of carbon dioxide,
from 40 to 80% by volume of at least one hydrocarbon selected from the group consisting of methane, ethane, propane, n-butane, isobutane and ethene (preferably at least 80 mol % of the total molar amount of these hydrocarbons is methane), and
from >0 to 5% by volume of other compounds including but not limited to propene and/or acrylic acid,
and containing
the molecular oxygen and the acrolein in a molar $O_2$:acrolein ratio ranging from 0.5 to 3,
the carbon dioxide and the carbon monoxide in a molar $CO_2$:CO ratio ranging from 1 to 4,
the molecular oxygen and the molecular nitrogen in a molar $O_2$:$N_2$ ratio of at least 0.25, and
the carbon monoxide and the total molar amount (quantity) of hydrocarbons (including acrolein) in a molar CO:total hydrocarbons ratio ranging from >0 to 0.3,
at a reaction temperature of from 200° C. to 450° C. and a working pressure of from 1 bar to 6 bar through a second fixed catalyst bed comprising shaped catalyst bodies whose active mass is at least one multimetal oxide containing molybdenum (Mo) and vanadium (V) in such a way, that the acrolein conversion on single pass is from 95 mol % to 99.99 mol % and the accompanying selectivity $S^{AA}$ of the formation of the target product acrylic acid assessed over both reaction stages and based on converted propene is from 80 mol % to 99.9 mol % to obtain a stream of a the target product acrylic acid containing product gas mixture 2 leaving the second reaction stage,
and C) either continuously transporting the stream of the target product acrolein containing product gas mixture 1 or the stream of the target product acrylic acid containing product gas mixture 2 into a separating zone and separating in the separating zone the respective target product from the respective product gas mixture through transferring at least 95 mol % of the respective target product contained in the respective product gas mixture from the gaseous phase into the liquid phase and continuously conducting out of the separating zone a total mass flow M of a residual gas mixture R which contains, of the total molar amount of those compounds contained in the product gas mixture continuously transported into the separating zone, which have as pure compounds at a working pressure of 1 bar a boiling point below 250 K, at least 95 mol % and D) recycling as gaseous stream P having the same composition as the residual gas mixture R a partial stream of the total mass flow M of residual gas mixture R continuously conducted out of the separating zone into the first reaction stage 1 as feed stream for preparing the stream of the starting reaction gas mixture 1 which shall contain the gaseous stream P, and discharging of the production process as off-gas stream O, having the same composition as the residual gas mixture R, the difference between the total mass flow M of residual gas mixture R continuously conducted out of the separating zone and the mass flow of recycle gaseous stream P, wherein
  a) the mass flow of the recycle gaseous stream P is at least 75% but not more than 98% of the total mass flow M of residual gas mixture R continuously conducted out of the separating zone,
  b) the mass flow of the off-gas stream O is not more than 25% but at least 2% of the total mass flow M of residual gas mixture R continuously conducted out of the separating zone, and
  c) the composition C of the residual gas mixture R is
    from 0.05 to 0.8% by volume of propene,
    from 1 to 4% by volume of molecular oxygen,
    from 0.5 to 10% by volume of water,
    from 0 to 10% (preferably 0 to 5%) by volume of molecular nitrogen,
    from 1.2 to 15% by volume of carbon monoxide,
    from 3 to 30% by volume of carbon dioxide,
    from 45 to 90% by volume of at least one hydrocarbon selected from the group consisting of methane, ethane, propane, n-butane, isobutane and ethene (preferably at least 80 mol % of the total molar amount of these hydrocarbons is methane), and
    from 0.01 to 5% by volume of other compounds including but not limited to acrolein and/or acrylic acid.

In case of the aforesaid second highly preferred embodiment the feed streams forming (used for preparing) starting reaction gas mixture 1 preferably consist only of a propene feedstock stream of polymer grade propene (propene feedstock containing ≥99% by vol. propene and ≤1% by vol. propane) or chemical grade propene (propene feedstock containing ≥90% by vol. propene and ≤10% by vol. but ≥2% by vol. propane), a stream of molecular oxygen of the purity ≥99.0% by vol. and ≤99.9% by vol. $O_2$ and ≤1% by vol. and ≥0.1% by vol. $N_2$, recycle gaseous stream P and an additional stream of at least one hydrocarbon selected from the group consisting of methane, natural gas, ethane, propane, n-butane, isobutane and ethene (preferably at least 80 mol % (better at least 90 mol % and more preferably at least 95 mol % and best 100 mol %) of the total molar amount of these hydrocarbons is methane or natural gas).

In principle the stationary production process according to the invention can be carried out with both non-ignitable (non-explosive) and ignitable (explosive) gas mixtures (regarding ignitability of gas mixtures see U.S. Pat. Nos. 6,090,977 and 5,684,188), provided in each case it is carried out with adequate safety measures (see line 21 to 31 on page 7 of WO 2004/007405). What is crucial in answering the question of whether a gas mixture is explosive (ignitable) or not is whether combustion (ignition, explosion) initiated by a local ignition source (for example a glowing platinum wire) spreads in the gas mixture present under certain conditions (pressure, temperature) or not (cf. DIN 51649 and the experiment description in WO 04/007405, especially its page 2). When there is spreading, the mixture shall be classified here as explosive (ignitable). When there is no spreading, the mixture is classified in this document as non-explosive (non-ignitable). As disclosed in WO 04/007404 it is easily possible to determine for a certain number of compounds which at a certain temperature and pressure may constitute a variety of gas mixtures showing different compositions, the explosion limit line. This is the line which in the explosion diagram (it shows the explosion behavior versus the composition) separates the explosive gas mixtures from the non-explosive ones. Under the in this document relevant stationary operating conditions as a rule of thumb, it is considered that when the starting reaction gas mixture 1 is non-explosive (it usually comprises the highest concentration of molecular oxygen; sections [0028], [0029] and [0030] of US-A 2004/0015012 apply correspondingly), this normally also applies to the reaction gas mixtures formed (resulting) therefrom within the inventive process. Preferably the inventive process is carried out outside the explosive (ignitable) range. From an economic point of view, it is preferred, to carry out the inventive process by applying starting reaction gas mixtures 1 which at the reaction conditions are non-explosive on the one hand and on the other hand have high concentrations of reactants propene and molecular oxygen (this correspondingly applies to the reactants acrolein and molecular oxygen in starting reaction gas mixture 2). Because of all the aforesaid the ratio $Q=(n_{CO})/(n_{CO}+n_{hydrocarbon})$ in the starting reaction gas mixture 1 of the inventive process preferably ranges from >0 to 0.8, more preferably from 0.005 to 0.7 and best from 0.005 to 0.6 ($n_{CO}$ means the total molar amount of carbon monoxide contained in the starting reaction gas mixture 1 and $n_{hydrocarbon}$ means the total molar amount of hydrocarbons (saturated and unsaturated) contained in the starting reaction gas mixture 1). The relationship $Q=(n_{CO})/(n_{CO}+n_{hydrocarbon})$ >0 to 0.8 (more preferably from 0.005 to 0.7 and best from 0.005 to 0.6) also applies in the same way to starting reaction gas mixture 2. However relating to starting reaction gas mixture 2 $n_{hydrocarbon}$ means the total molar amount of hydrocarbons (saturated and unsaturated) plus the total molar amount of acrolein contained in starting reaction gas mixture 2. The above formula first takes into account that while gases like $CO_2$, $N_2$, $H_2O$ and all noble gases are gases whose mixtures with molecular oxygen ($O_2$) under normal conditions are not capable of combustion reaction spreading from an ignition source at any mixing ratios (accordingly such gases are designated "nonflammable gases"), carbon monoxide (CO) is a flammable gas whose mixtures with $O_2$ are capable of a combustion reaction spreading from an ignition source at certain mixing ratios. In addition, this formula takes into account that the desired and catalytically promoted target oxidations (the primary reactions) of propene to acrolein respectively of acrolein to acrylic acid in the inventive process are always accompanied by undesired secondary reactions, among which the main ones are combustion reactions of propene respectively acrolein forming carbon monoxide and carbon dioxide and that, based on the total mass flow M of residual gas mixture R continuously conducted out of the separating zone, the compared to the state of the art processes in the inventive process increased proportion of recycle gaseous stream P correspondingly increases the concentration of carbon monoxide in starting reaction gas mixture 1 and in starting reaction gas mixture 2 with an enhanced risk of deflagration. Finally, the above formula takes also into account the fact well-known from the prior art, that through the presence of fuel gases such as saturated and unsaturated hydrocarbons in starting reaction gas mixture 1 respectively 2 such flammability behavior can be restricted (cf. Chem. Technik 50. Jg. Heft 5, September/October 1998, page 241 to 245).

What is important in case of the continuous operation of the invention process with compositions of starting reaction gas mixtures 1 which are outside the explosive area is (as the safety measures otherwise applied in this case normally are comparatively limited), that the continuous operation has a cut-out mechanism which prevents the composition of a reaction gas starting mixture 1 which is outside the explosion area from migrating into the explosion area during the continuous operation (in particular in the steady state) as a result of accidental faults in the gas streams fed to the formation of starting reaction gas mixture 1. This cut-out respectively shutdown mechanism can be configured in the following simple manner in accordance with the teaching of WO 2004/007405, WO 2015/104397 and WO 2018/029215:

a) an explosion diagram (the pressure and temperature dependence of an explosion diagram is limited and where changes are not too large, can be neglected; section [0122] of US 2004/0015012 applies correspondingly) characteristic of the starting reaction gas mixture 1 (as long as the specific heat of nonflammable inert diluent gases does not differ considerably from each other they influence the explosion diagram in the same way) and in which explosive and nonexplosive compositions are delineated from one another as a function of the composition of starting reaction gas mixture 1 is stored in a computer (for safety reasons, it may be expedient to deposit in the computer as an explosion diagram not the curve of the experimentally determined explosion limit but a switching curve shifted downward relative to this by a safety margin (see section [0065] of US-A 2004/0015012);

b) a data set is continuously determined by determination of the amount and optionally composition of the gaseous feed streams forming starting reaction gas mixture 1;

c) the computer continuously calculates an instantaneous operating point of the starting reaction gas mixture 1 in the explosive diagram from the data set obtained in b);

d) if the distance of the operating point from the closest explosive limit is below a prescribed minimum value, the flow of the gaseous streams feeding starting reaction gas mixture 1 is automatically interrupted (closed).

Preferably the feed streams are not closed simultaneously. Rather, the sequence of closing the gaseous feed streams preferably is selected as follows (due to safety reasons):

1. the feed stream comprising fresh molecular oxygen=feedstock (source) of molecular oxygen (including any optional addition of a molecular oxygen containing secondary gas to the product gas mixture 1 between the first reaction stage and the second reaction stage for forming starting reaction gas mixture 2);

2. the feed stream comprising fresh propene=propene feedstock;

3. feed streams of other hydrocarbons optionally co-used as inert diluent gases for the starting reaction gas mixture 1;

4. an optionally co-used feed stream of steam which also may serve as inert diluent gas in starting reaction gas mixture 1 and additionally is known as a means for increasing the catalytic activity of the multimetal oxide catalysts used in the production process; and 5. recycle gaseous stream P.

Such shutdown mechanism expediently will also be installed regarding starting reaction gas mixture 2.

In addition, $n_{CO}$ and $n_{hydrocarbon}$ may continuously be determined for the given starting reaction gas mixture 1 and the given starting reaction gas mixture 2 and the resulting values continuously be fed into a computer who based on the determined values continuously calculates for each of the two starting reaction gas mixtures the ratio $Q=(n_{CO})/(n_{CO}+n_{hydrocarbon})$. In case any Q approaches the value 0.7 or 0.8, the flow of the gaseous streams feeding starting reaction gas mixture 1 respectively starting reaction gas mixture 2 (e.g. any secondary molecular oxygen containing gas stream optionally added between the first and second reaction stage) again is automatically interrupted (closed) as described above.

To generate (form) the stream of starting reaction gas mixture 1 the individual feed streams usually are fed to the first reaction stage (the first oxidation reactor) in such a way, that they arrive coming from separate feed lines (usually, all feed streams are already essentially compressed to the inlet pressure required to enter the first reaction stage), and are first fed to a mixer (for example a static mixer (cf. a chamber with internals which generate turbulences)), in which they are homogeneously mixed and then, if necessary after heating to the inlet temperature, fed to the first reaction stage (to the first oxidation reactor). The entry of the individual feed gases into the line leading to the static mixer is (in flow direction along said line) due to safety reasons preferably carried out in the opposite sequence (in the reverse order) as the closing of the gaseous feed streams in case of a cut-out respectively shutdown of the production process (that is first (1.) recycle gaseous stream P and last (5.) the feed stream comprising fresh molecular oxygen).

But even if the selected composition of the homogeneously mixed starting reaction gas mixture 1 is a nonexplosive one, the problem remains, that at the (local) point where the feed stream containing the fresh molecular oxygen is supplied (even if at that point it would be supplied into a (feed) stream Z which contains the streams of recycle gaseous stream P, an optionally co-used feed stream of steam, any optionally co-used feed streams of co-used inert hydrocarbons other than propene and the feed stream of the fresh propene (propene feedstock) already perfectly homogeneously mixed) the locally resulting gas mixture is normally an explosive one (this problem would even exist if ambient air would be used as source of fresh oxygen, however due to the comparatively high content of molecular nitrogen in air the problem would be less serious (less severe)).

In accordance with the invention the following procedure is therefore advantageously used. First, as described above, a simple static mixture is used to generate the homogeneously mixed feed stream Z. This stream is then mixed with the feed stream (the source) comprising fresh molecular oxygen (with a stream of molecular oxygen of the purity ≥90% by vol. $O_2$ (preferably ≥95% by vol. $O_2$) and ≤10% by vol. $N_2$ (preferably ≤5% by vol. $N_2$) with the aid of a mixing device which is particularly suitable relating to the problem to be solved, namely to optimally protect the local formation of an explosive gas mixture. After leaving the mixing device, the resulting starting reaction gas mixture 1 is fed into the first reaction stage (the respective oxidation reactor).

Such a device being suitable for the relevant purpose is disclosed in WO 2009/078898 respectively in U.S. Pat. No. 8,334,395. When using this device for the relevant mixing, the gaseous feed stream Z is mixed with the feed stream of fresh molecular oxygen (with the source of molecular oxygen) in a gas mixer in the presence of coarse water droplet environment. The water droplets surround and contact entrained particles in either the fresh molecular oxygen containing gas stream or the feed stream Z. The water acts to suppress, prevent and quench ignition of the hydrocarbon and carbon monoxide gas in the mixer which would otherwise be caused by energetic collisions between such particles and structures within the gas mixer.

An alternative mixing device suitable for the relevant purposes discloses WO 2007/071737. Carrying out the mixing in this mixing device comprises conveying the gaseous feed stream Z as a first stream and the gaseous stream containing the fresh molecular oxygen (the source of molecular oxygen) as a second stream into a microchannel apparatus, allowing mixing to occur, and withdrawing the mixture. The advantage of this mixing device is that it enables a mixing process which minimizes the length of time that the molecular oxygen/(hydrocarbon+CO) containing mixture may exist in the relevant explosive region. The gases are mixed on a "microlevel", i.e. on a very small scale, within process microchannels of the microchannel apparatus. Initially after intermingling of both feeds there will of course be pockets of oxygen-rich and oxygen-poor mixtures, however the splitting up and recombination of the oxygen flow in the process microchannels and, where present, via the microchannel orifices, will establish an average oxygen concentration below explosion limits. As the gas mixture progresses through the microchannel apparatus, these pockets will disappear, and the gases will become well-mixed on a microlevel.

A further suitable mixing device is disclosed in U.S. Pat. No. 8,404,189 respectively in WO 2009/078899. This gas mixer includes a vessel containing the feed stream Z (the first gas stream) and a hollow pipe located internal to the vessel containing the feed stream of fresh molecular oxygen (the second gas stream). The internal pipe further includes a mixer tip at the peripheral end thereof. The mixer tip includes a body having an internal passage for conducting the second gas out of the pipe and an opening introducing the second gas stream into the first gas stream in a radial plane at an acute angle relative to the longitudinal axis of the pipe. The pipe further includes a deflector on its external surface in longitudinal alignment with the opening of the mixer tip. The deflector serves to deflect any entrained particles within the first gas stream away from the mixing zone where the two streams mix, minimizing the risk of ignition of the hydrocarbon and CO containing gas Z.

In case of adding a source of molecular oxygen such as molecular oxygen of a purity of $\geq 90\%$ by vol. and 10% by vol. $N_2$ to the product gas mixture 1 leaving the first reaction stage to generate starting reaction gas mixture 2, preferably any of above described mixing devices is correspondingly applied (in such case stream of product gas mixture 1 will have the position stream Z has in the above described).

At the transition from a first stationary operating state to a second stationary operating state whereby in the second stationary operating state the load of the fixed catalyst bed in the first reaction stage with starting reaction gas mixture 1 under otherwise unchanged conditions is higher than in the first stationary operating state, it is due to safety (to be constantly outside the explosive area during the transition) and other reasons advantageous to proceed in such a way, that the propene load is increased again and again in small successive steps and after each such step, before carrying out the next such step, the load with molecular oxygen (including any molecular oxygen containing secondary gas introduced between the first and the second reaction stage) is correspondingly increased (balanced) until the new stationary operating condition is reached (both stationary operating conditions are assumed as non-explosive). In case in the second stationary operating state the load of the fixed catalyst bed in the first reaction stage with starting reaction gas mixture 1 under otherwise unchanged conditions is lower than in the first stationary operating state, it is due to safety and other reasons correspondingly advantageous to proceed for the transition in such a way, that the load with molecular oxygen (including any molecular oxygen containing secondary gas introduced between the first and the second reaction stage) is reduced again and again in small successive steps and after each such step, before carrying out the next such step, the load with propene is correspondingly reduced (balanced) until the new stationary operating condition is reached (both stationary operating conditions are assumed as non-explosive).

To start up the production process the individual feed streams necessary for generating (forming) starting reaction gas mixture 1 are opened (started up) in the opposite sequence (in the reverse order) as in case of the closing of these feed streams for a shutdown of the production process. Instead of recycle gaseous stream P, at the beginning lean air can be used. This is a mixture consisting of 4 to 6% by vol. of $O_2$ and of 94 to 96% by vol. $N_2$. A subsequent feed stream preferably is only started up after the volume flow of the previously opened feed stream has already reached at least 70% of its target value at stationary operation.

Another option to start up the invention process is to proceed in an equivalent manner as taught in EP-A 1180508.

Furthermore, preference is given to inventive processes in which the following conditions are simultaneously fulfilled:
   a) starting reaction gas mixture 1 contains from 3 to 10% by volume propene, from 3.9 to 23% by volume molecular oxygen and contains the molecular oxygen and the propene in a molar $O_2$:propene ratio ranging from 1.3 to 2.1; and (only in case acrylic acid is the target product; otherwise b) is not applicable)
   b) starting reaction gas mixture 2 contains from 3 to 10% by volume acrolein, from 1.8 to 25% by volume of molecular oxygen and contains the molecular oxygen and the acrolein in a molar $O_2$:acrolein ratio ranging from 0.6 to 2.5.

In addition, such inventive processes are particularly preferred in which the following conditions are simultaneously fulfilled:
   a) starting reaction gas mixture 1 contains from 4 to 9% by volume propene, from 5.6 to 19.8% by volume molecular oxygen and contains the molecular oxygen and the propene in a molar $O_2$:propene ratio ranging from 1.4 to 2.2; and (only in case acrylic acid is the target product; otherwise b) is not applicable)
   b) starting reaction gas mixture 2 contains from 4 to 9% by volume acrolein, from 2.8 to 18% by volume of molecular oxygen and contains the molecular oxygen and the acrolein in a molar $O_2$:acrolein ratio ranging from 0.7 to 2.0.

Even more preferred are those inventive processes in which the following conditions are simultaneously fulfilled:
   a) starting reaction gas mixture 1 contains from 5 to 8% by volume propene, from 7.5 to 16.8% by volume molecular oxygen and contains the molecular oxygen and the propene in a molar $O_2$:propene ratio ranging from 1.5 to 2.1; and (only in case acrylic acid is the target product; otherwise b) is not applicable)

b) starting reaction gas mixture 2 contains from 4.5 to 8% by volume acrolein, from 3.6 to 12% by volume of molecular oxygen and contains the molecular oxygen and the acrolein in a molar $O_2$:acrolein ratio ranging from 0.8 to 1.5.

As already addressed above, starting reaction gas mixture 1 of the inventive process basically is formed (prepared) from at least three feed streams:

a) a stream comprising fresh propene (=propene not yet used in the process; propene feedstock) such as refinery propene, chemical grade propene and/or polymer grade propene;

b) a stream comprising fresh molecular oxygen (=molecular oxygen not yet used in the process; the source of molecular oxygen) such as molecular oxygen of a purity of at least (≥) 95% by vol. (in relation to the total volume) $O_2$ and not more than (≤) 5% by vol. $N_2$; and c) recycle gaseous stream P.

Further feed streams to the formation of starting reaction gas mixture 1 may be streams of at least one hydrocarbon selected from the group consisting of methane, natural gas, ethane, propane, n-butane, isobutane and ethene (preferably consisting of methane, natural gas and propane). Additionally, a stream of steam ($H_2O$) may be a feed stream to the formation of reaction gas mixture 1. As the separation of the target products (especially in case of the target product acrylic acid) from water in the separating zone is energy consuming such feed stream of steam is not necessarily preferred.

In this document, the loading of a fixed catalyst bed with a reaction gas (e.g. starting reaction gas mixture 1) is understood to mean the amount of reaction gas in standard liters (=l (STP); the volume in liters that the corresponding amount of reaction gas would take up under standard conditions (0° C., 1 bar)) which is conducted through one liter of fixed catalyst bed per hour. The loading may also be based only on one constituent of the reaction gas. In that case, it is the amount of this component in standard liters which is conducted as a constituent of the reaction gas through one liter of the fixed catalyst bed per hour (l (STP)/l·h). Pure inert material beds (bed sections) here are not counted toward the fixed catalyst bed whereas fixed beds (fixed bed sections) consisting of a mixture of catalysts and inert shaped diluent bodies are here included (such counted) as a whole.

The term syngas (synthesis gas) in this document is understood to mean a gas mixture G which contains molecular hydrogen ($H_2$) and at least one of the carbon oxides CO (carbon monoxide) and $CO_2$ (carbon dioxide) and optionally one or more of the constituents from the group C* consisting of hydrocarbons $C_nH_m$ (e.g. methane, ethane, propane, n-butane, isobutane and ethene) in which $1 \leq n \leq 4$ and $4 \leq m \leq 10$, molecular nitrogen ($N_2$), molecular oxygen ($O_2$), water ($H_2O$) and the noble gases (especially He, Ne, Ar, Kr, Xe and Rn) with the proviso that the total molar amount of $H_2$, CO and $CO_2$ contained in the gas mixture G, based on the total molar amount of all constituents contained in the gas mixture G, is at least 90 mol %, the total molar amount of $H_2$, CO, $CO_2$ and constituents from the group C* contained in the gas mixture G, based on the total molar amount of all constituents contained in the gas mixture G, is at least 99 mol %, and the total molar amount of CO and $CO_2$ contained in the gas mixture G, based on the total molar amount of $H_2$, CO and $CO_2$ contained in the gas mixture G, is at least 25 mol % but not more than 50 mol %.

Such gases are named "synthesis gases" since they can be used in a manner known per se for the synthesis of chemical compounds containing C and H and optionally O (e.g. US-A 2009/0018220 and WO 2010/067945 describe the synthesis of methanol from CO and $CO_2$ containing synthesis gas; WO 2015/145311 describes the synthesis of hydrocarbons by Fischer Tropsch synthesis from CO and $CO_2$ containing synthesis gas; further on, synthesis gas can be used for production of oxygenates e.g. via hydroformylation of unsaturated hydrocarbons such as olefins and acetylenes; WO 2005/095315 discloses the hydroformylation of propene with synthesis gas rich in CO to butyraldehyde; said butyraldehyde can be further converted into butanol by hydrogenation as described in EP-B 1027315 or in U.S. Pat. Nos. 3,925,490; 5,041,683 describes the synthesis of alcohols and aldehydes from alkenes and synthesis gas; butanol and acrylic acid (optionally obtained by the inventive process) may be further converted into butyl acrylate as described in U.S. Pat. Nos. 2,886,591; 5,227,544 describes the synthesis of 2-ethylhexanol (which may be esterified with acrylic acid to yield 2-ethylhexyl acrylate) from butyraldehyde; acetic acid (2 $CO+2H_2 \rightarrow CH_3COOH$), ethanol ($CH_3OH+CO+H_2 \rightarrow CH_3$—$CH_2$—OH) and glycol (2 $CO+3H_2 \rightarrow HOCH_2$—$CH_2OH$) may also be produced from syngas).

It is well known (see e.g. Ullmann's Encyclopedia of Industrial Chemistry, Fifth Completely Revised Edition, Volume A12 (Formamides to Hexamethylendiamine), VCH Verlagsgesellschaft mbH, D-6940 Weinheim, pages 178 and 179, section 1.3.) that synthesis gas e.g. can be produced (normally such production is made on purpose, i.e. the resulting syngas is directly processed further into the subsequent products) by heterogeneously catalyzed steam reformation of hydrocarbons in the gas phase:

$$C_xH_y + xH_2O \leftrightarrow xCO + (x+0.5y)H_2, \text{ and}$$

heterogeneously catalyzed hydrogenation of $CO_2$ in the gas phase:

$$CO_2 + H_2 \leftrightarrow CO + H_2O.$$

Both reactions preferably are carried out at high temperatures and high pressures (see e.g. U.S. Pat. Nos. 6,312,658, 4,233,179 and WO 2009/000494) and applying well known catalysts. A combined application of both reactions (see e.g. WO 2015/135968 and U.S. Pat. No. 4,233,179) makes it possible to control the composition of the resulting product gas mixture ("syngas") within certain limits as desired.

According to U.S. Pat. No. 3,506,418 gaseous hydrocarbons can also be reformed dry with carbon dioxide instead of steam, e.g.:

$$3CO_2 + C_3H_8 \leftrightarrow 6CO + 4H_2, \text{ or}$$

$$CO_2 + CH_4 \leftrightarrow 2CO + 2H_2.$$

Through partial gas phase combustion of hydrocarbons and/or organic compounds being composed of C, H and O formation of CO and $H_2O$ is possible:

$$C_xH_y + (x/2+y/4)O_2 \leftrightarrow xCO + y/2H_2O.$$

In case of gas mixtures containing all relevant reactants (as in case of certain off-gases of the inventive process) an overlap of all four above outlined reaction types can be applied to produce the intended syngas composition. However, it is also possible to add to off-gas produced by an inventive process before using it for production of any syngas one or more of those reactants, such as hydrocarbons from the group consisting of methane, natural gas, ethane, propane, n-butane, isobutane and ethene. Preferably, how- ever, such hydrocarbons (preferably propane and/or meth- ane (respectively natural gas)) are already part of starting reaction gas mixture 1, as their presence has a positive influence (see e.g. U.S. Pat. Nos. 6,090,977 and 5,684,188) on the ignition behavior of starting reaction gas mixture 1 as a whole due to their own combustibility as well as on the suppression of undesired hot spot formation within the fixed catalyst bed due their increased molar heat capacity $C_p$ which enables these compounds to absorb reaction heat to a comparatively high extent.

One of the essential aspects of the present invention is, that the relevant off-gas discharged from the process carried out for production of the target product acrolein or acrylic acid has only a limited content of molecular nitrogen. This is because such molecular nitrogen will finally be contained in the resulting "synthesis gas". Chemical synthesis pro- cesses based on synthesis gas (such as hydroformylation of e.g. propene) normally are however continuous processes which do not result in 100% conversion of the starting materials (e.g. propene) involved. Accordingly, the resulting product mixtures still contain unreacted raw material and the inert molecular nitrogen. It is of course economically desir- able that said unreacted raw materials be recycled into the respective synthesis process. However, for the continuous chemical synthesis gas process (e.g. hydroformylation) being operated successfully on an industrial scale, it is important to establish a steady state between the feed materials, including any recycle, and the degree of reaction. It is therefore important to prevent excessive $N_2$ accumula- tion (build-up) in the reaction system due to recycle of the unreacted components. However, molecular nitrogen is dif- ficult to separate from other compounds involved such as CO, $CO_2$, propene, $H_2$ and others. Thus, to prevent signifi- cant $N_2$ accumulation (build-up) due to recycle, it is neces- sary to vent off at least some of the molecular nitrogen. This removal is all the more pronounced, as higher the $N_2$ content of the off-gas used for syngas production is. As any such $N_2$ removal necessarily also will involve the removal of some remaining raw material, it automatically will cause some undesired inefficiencies and economic debits in the process.

In this regard it is advantageous that due to the increase in volume during the production of syngas (corresponding to the increase in the number of molecules) from off-gas, the concentration of molecular nitrogen at the transition from off-gas to syngas may drop to an economically still rather acceptable level with a view to subsequent uses of the syngas produced.

The realization of the one-stage heterogeneously cata- lyzed partial oxidation of propene to the target product acrolein (and normally small amounts of acrylic acid as by-product) or of the two-stage heterogeneously catalyzed partial oxidation of propene to the target product acrylic acid (and normally small amounts of acrolein as by-product) using a starting reaction gas mixture 1 may in an equivalent manner be carried out as described for similar reaction gas mixtures in the documents EP-A 700714 (first reaction stage; as described there, but also in corresponding coun- tercurrent mode of salt bath and starting reaction gas mixture 1 over the tube bundle reactor), EP-A 700893 (second reaction stage; as described there, but also in corresponding countercurrent mode of salt bath and starting reaction gas mixture 2 over the tube bundle reactor), WO 04/085369 (the two-stage process), WO 04/85363, DE-A 10313212 (first reaction stage), EP-A 1159 248 (the two-stage process), EP-A 1159246 (second reaction stage), EP-A 1 159 247 (the two-stage process), DE-A 19948248 (the two-stage pro- cess), WO 04/085368 (the two-stage process), DE-A 102004021764 (the two-stage process), WO 04/085362 (first reaction stage), WO 04/085370 (second reaction stage), WO 04/085365 (second reaction stage), WO 04/085367 (the two-stage process), EP-A 990636, EP-A 1 007007 and EP-A 1106598.

This is especially true of all working examples contained in these documents. They may be carried out as described in these documents, but with the difference that the starting reaction gas mixture used for the first reaction stage (pro- pene to acrolein) is a starting reaction gas mixture 1 gener- ated in accordance with the invention. Regarding the remaining parameters, the procedure is as in the working examples of the documents mentioned (especially regarding the fixed catalyst beds and reactant loading of the fixed catalyst beds). When the procedure in the aforementioned working examples of the prior art is in two stages and there is secondary oxygen feeding between the two reaction stages, the feeding is undertaken in a corresponding manner, but is adjusted in its amount to the effect that the molar ratio of molecular oxygen to acrolein in the starting reaction gas mixture 2 of the second reaction stage corresponds to that as required in this document (ranging from 0.5 to 3).

Advantageously in accordance with the invention, the amounts of molecular oxygen in starting reaction gas mix- ture 1 respectively in starting reaction gas mixture 2 are such that product gas mixture 1 when leaving the first reaction stage respectively the product gas mixture 2 when leaving the second reaction stage still comprises unconverted molecular oxygen (appropriately from ≥0.5 to 6% by vol- ume, advantageously from 1 to 5% by volume, preferably from 2 to 4% by volume).

Multimetal oxide catalysts particularly suitable for the respective reaction stage have been described many times before and are well known to those skilled in the art. For example, EP-A 253409 refers on page 5 to corresponding US patents.

Favorable catalysts for the respective oxidation stage are also disclosed by DE-A 4431957, DE-A 102004025445 and DE-A 4431949. This is especially true of those of the general formula I in the two of these three addressed documents which have the earlier publication date. Particularly advan- tageous catalysts for the respective oxidation stage are disclosed by the documents DE-A 10325488, DE-A 10325487, DE-A 10353954, DE-A 10344149, DE-A 10351269, DE-A 10350812 and DE-A 10350822.

For the first reaction stage of the invention process applicable catalysts are catalysts whose active mass is at least one multimetal oxide composition comprising Mo, Bi and Fe.

Such catalytically active multimetal oxide compositions are in particular the multimetal oxide active compositions of the general formula I of DE-A 19955176, the multimetal oxide active compositions of the general formula I of DE-A 19948523, the multimetal oxide active compositions of the general formulae I, II and III of DE-A 10101695, the multimetal oxide active compositions of the general formu- lae I, II and III of DE-A 19948248 and the multimetal oxide active compositions of the general formulae I, II and III of DE-A 19955168 and also the multimetal oxide active com- positions specified in EP-A 700714.

Also suitable for the first reaction stage are the multimetal oxide catalysts comprising Mo, Bi and Fe which are disclosed in the documents Research Disclosure No. 497012 of Aug. 29, 2005, DE-A 10046957, DE-A 10063162, DE-C 3338380, DE-A 19902562, EP-A 15565, DE-C 2380765, EP-A 807465, EP-A 2793 74, DE-A 3300044, EP-A 575897, U.S. Pat. No. 4,438,217, DE-A 19855913, WO 98/24746, DE-A 19746210 (those of the general formula II), JP-A 91/294239, EP-A 293224 and EP-A 700 714. This especially applies to the exemplary embodiments in these documents, and among these, preference is given to those of EP-A 15565, EP-A 575897, DE-A 19746210 and DE-A 19855913. Emphasis is given in this context to a catalyst according to example 1c from EP-A 15565 and to a catalyst to be prepared in a corresponding manner but whose active composition has the composition $Mo_{12}Ni_{6.5}Zn_2Fe_2Bi_1P_{0.0065}K_{0.06}O_x \cdot 10SiO_2$. Emphasis is also given to the example having the serial number 3 from DE-A 19855913 (stoichiometry: $Mo_{12}Co_7Fe_3Bi_{0.6}K_{0.08}Si_{1.6}O_x$) as an unsupported hollow cylinder catalyst of geometry 5 mm×3 mm×2 mm (external diameter×height×internal diameter) and also to the unsupported multimetal oxide II catalyst according to example 1 of DE-A 19746210. Mention should also be made of the multimetal oxide catalysts of U.S. Pat. No. 4,438,217. The latter is especially true when these hollow cylinders have a geometry of 5.5 mm×3 mm×3.5 mm, or 5 mm×2 m×2 mm, or 5 mm×3 mm×2 mm, or 6 mm×3 mm×3 mm, or 7 mm×3 mm×4 mm (each external diameter×height×internal diameter). Further possible catalyst geometries in this context are extrudates (for example length 7.7 mm and diameter 7 mm; or length 6.4 mm and diameter 5.7 mm).

A multitude of the multimetal oxide active compositions suitable for the step from propene to acrolein can be encompassed by the general formula I $$Mo_{12}Bi_aFe_bX^1_cX^2_dX^3_eX^4_fO_n \qquad (I)$$

in which the variables are each defined as follows:
$X^1$=nickel and/or cobalt,
$X^2$=thallium, an alkali metal and/or an alkaline earth metal,
$X^3$=zinc, phosphorus, arsenic, boron, antimony, tin, cerium, lead and/or tungsten,
$X^4$=silicon, aluminum, titanium and/or zirconium,
a=from 0.5 to 5,
b=from 0.01 to 5, preferably from 2 to 4,
c=from 0 to 10, preferably from 3 to 10,
d=from 0 to 2, preferably from 0.02 to 2,
e=from 0 to 8, preferably from 0 to 5,
f=from 0 to 10 and
n=a number which is determined by the valency and frequency of the elements in I other than oxygen.
They are obtainable in a manner known per se (see, for example, DE-A 4023239) and are customarily shaped in substance to give spheres, rings or cylinders or else used in the form of coated catalysts, i.e. pre-shaped inert support bodies coated with the active composition.

In principle, active compositions of the general formula I can be prepared in a simple manner by obtaining a very intimate, preferably finely divided dry mixture having a composition corresponding to their stoichiometry from suitable sources of their elemental constituents and calcining it at temperatures of from 350 to 650° C. The calcination may be effected either under inert gas or under an oxidative atmosphere, for example air (mixture of inert gas and oxygen) and also under a reducing atmosphere (for example mixture of inert gas, $NH_3$, CO and/or $H_2$). The calcination time can be from a few minutes to a few hours and typically decreases with temperature. Useful sources for the elemental constituents of the multimetal oxide active compositions I are those compounds which are already oxides and/or those compounds which can be converted to oxides by heating, at least in the presence of oxygen.

In addition to the oxides, such useful starting compounds include in particular halides, nitrates, formates, oxalates, citrates, acetates, carbonates, amine complexes, ammonium salts and/or hydroxides (compounds such as $NH_4OH$, $(NH_4)_2CO_3$, $NH_4NO_3$, $NH_4CHO_2$, $CH_3COOH$, $NH_4CH_3CO_2$ and/or ammonium oxalate which decompose and/or can be decomposed on later calcining at the latest to give compounds which are released in gaseous form can be additionally incorporated into the intimate dry mixture).

The starting compounds for preparing multimetal oxide active compositions I can be intimately mixed in dry or in wet form. When they are mixed in dry form, the starting compounds are appropriately used as finely divided powders and subjected to calcination after mixing and optional compacting. However, preference is given to intimate mixing in wet form. Typically, the starting compounds are mixed with each other in the form of an aqueous solution and/or suspension. Particularly intimate dry mixtures are obtained in the mixing process described when the starting materials are exclusively sources of the elemental constituents in dissolved form. The solvent used is preferably water. Subsequently, the aqueous composition obtained is dried, and the drying process is preferably effected by spray-drying the aqueous mixture at exit temperatures of from 100 to 150° C.

The multimetal oxide active compositions of the general formula I will be used for the "propene→acrolein" step shaped to certain catalyst geometries, and the shaping may be effected either before or after the final calcination. For example, unsupported catalysts can be prepared from the powder form of the active composition or its uncalcined and/or partially calcined precursor composition by compacting to the desired catalyst geometry (for example by tableting or extruding), optionally with the addition of assistants, for example graphite or stearic acid as lubricants and/or shaping assistants and reinforcing agents such as microfibers of glass, asbestos, silicon carbide or potassium titanate. Instead of graphite, it is also possible to use hexagonal boron nitride as an assistant in the shaping, as recommended by DE-A 102005037678. Examples of suitable unsupported catalyst geometries include solid cylinders or hollow cylinders having an external diameter and a length of from 2 to 10 mm. In the case of the hollow cylinder, a wall thickness of from 1 to 3 mm is advantageous. The unsupported catalyst can of course also have spherical geometry, and the spherical diameter can be from 2 to 10 mm.

A particularly favorable hollow cylinder geometry is 5 mm×3 mm×2 mm (external diameter×length×internal diameter), especially in the case of unsupported catalysts.

The pulverulent active composition or its pulverulent precursor composition which is yet to be calcined and/or partially calcined may of course also be shaped by applying to pre-shaped inert catalyst supports. The coating of the support bodies to produce the coated catalysts is generally performed in a suitable rotatable vessel, as disclosed, for example, by DE-A 2909671, EP-A 293859 or EP-A 714700. To coat the support bodies, the powder composition to be applied is appropriately moistened and dried again after application, for example by means of hot air. The coating thickness of the powder composition applied to the support body is appropriately selected within the range from 10 to 1000 μm, preferably within the range from 50 to 500 μm and more preferably within the range from 150 to 250 μm.

Useful support materials are the customary porous or nonporous aluminum oxides, silicon dioxide, thorium dioxide, zirconium dioxide, silicon carbide or silicates such as magnesium silicate or aluminum silicate. They generally behave substantially inertly with respect to the target reaction on which the process according to the invention is based. The support bodies can have a regular or irregular shape, although preference is given to regularly shaped support bodies having distinct surface roughness, for example spheres or hollow cylinders. Suitable support bodies are substantially nonporous, surface-roughened spherical supports made of steatite whose diameter is from 1 to 10 mm or to 8 mm, preferably from 4 to 5 mm. However, suitable support bodies are also cylinders, whose length is from 2 to 10 mm and whose external diameter is from 4 to 10 mm. In the case of rings suitable in accordance with the invention as support bodies, the wall thickness is also typically from 1 to 4 mm. Annular support bodies to be used with preference in accordance with the invention have a length of from 2 to 6 mm, an external diameter of from 4 to 8 mm and a wall thickness of from 1 to 2 mm. Support bodies suitable in accordance with the invention are in particular also rings of geometry 7 mm×3 mm×4 mm (external diameter×length×internal diameter). The fineness of the catalytically active oxide compositions to be applied to the surface of the support body is of course adjusted to the desired coating thickness (cf. EP-A 714700).

Multimetal oxide active compositions preferably to be used for the step from propene to acrolein are also compositions of the general formula II $$[Bi_{a''}Z^2_{b''}O_{x''}]_{p''}[Z^2_{12}Z^3_{c''}Z^4_{d''}Fe_{e''}Z^5_{f''}Z^6_{g''}Z^7_{h''}O_{y''}]_{q''} \qquad (II)$$

in which the variables are each defined as follows:
$Z^2$=molybdenum or molybdenum and tungsten,
$Z^3$=nickel and/or cobalt,
$Z^4$=thallium, an alkali metal and/or an alkaline earth metal,
$Z^5$=phosphorus, arsenic, boron, antimony, tin, cerium and/or lead,
$Z^6$=silicon, aluminum, titanium and/or zirconium,
$Z^7$=copper, silver and/or gold,
a''=from 0.1 to 1,
b''=from 0.2 to 2,
c''=from 3 to 10,
d''=from 0.02 to 2,
e''=from 0.01 to 5, preferably from 0.1 to 3,
f''=from 0 to 5,
g''=from 0 to 10,
h''=from 0 to 1,
x'',y''=numbers which are determined by the valency and frequency of the elements in II other than oxygen,
p'',q''=numbers whose p''/q'' ratio is from 0.1 to 5, preferably from 0.5 to 2,
comprising three-dimensional regions of the chemical composition $Bi_{a''}Z^2_{b''}O_{x''}$ which are delimited from their local environment owing to their different composition from their local environment, and whose maximum diameter (longest direct line passing through the center of the region and connecting two points on the surface (interface) of the region) is from 1 nm to 100 µm, frequently from 10 nm to 500 nm or from 1 µm to 50 or 25 µm.

Very particular preference is given to those compositions II in which $Z^2_{b''}$=(tungsten)$_{b''}$ and $Z^2_{12}$=(molybdenum)$_{12}$.

It is also advantageous when at least 25 mol % (preferably at least 50 mol % and more preferably at least 100 mol %) of the total proportion of $[Bi_{a''}Z^2_{b''}O_{x''}]_{p''}$ of the multimetal oxide compositions II is in the form of three-dimensional regions of the chemical composition $[Bi_{a''}Z^2_{b''}O_{x''}]$ which are delimited from their local environment owing to their different chemical composition from their local environment, and whose maximum diameter is in the range from 1 nm to 100 µm.

Regarding the shaping, the statements made for the multimetal oxide composition I catalysts correspondingly apply to multimetal oxide composition II catalysts.

The preparation of multimetal oxide active compositions II is described, for example, in EP-A 575 897 and in DE-A 198 55 913.

The inert support materials recommended above are also useful, inter alia, as inert materials for the dilution and/or delimitation of the appropriate fixed catalyst beds, or as a preliminary bed which protects them and/or heats the gas mixture.

For the second step (the second reaction stage), the heterogeneously catalyzed gas phase partial oxidation of acrolein to acrylic acid, useful active multimetal oxide compositions for the catalysts required are, as already stated, in principle all multimetal oxide compositions comprising Mo and V, for example those of DE-A 100 46 928.

A multitude thereof, for example those of DE-A 19815281, can be encompassed by the general formula III $$Mo_{12}V_aX^1_bX^2_cX^3_dX^4_eX^5_fX^6_gO_n \qquad (III)$$

in which the variables are each defined as follows:
$X^1$=W, Nb, Ta, Cr and/or Ce,
$X^2$=Cu, Ni, Co, Fe, Mn and/or Zn,
$X^3$=Sb and/or Bi,
$X^4$=one or more alkali metals,
$X^5$=one or more alkaline earth metals,
$X^6$=Si, Al, Ti and/or Zr,
a=from 1 to 6,
b=from 0.2 to 4,
c=from 0.5 to 18,
d=from 0 to 40,
e=from 0 to 2,
f=from 0 to 4,
g=from 0 to 40 and
n=a number which is determined by the valency and frequency of the elements in III other than oxygen.

Embodiments which are preferred in accordance with the invention among the active multimetal oxides III are those which are encompassed by the following definitions of the variables of the general formula III:
$X^1$=W, Nb and/or Cr,
$X^2$=Cu, Ni, Co and/or Fe,
$X^3$=Sb,
$X^4$=Na and/or K,
$X^5$=Ca, Sr and/or Ba,
$X^6$=Si, Al and/or Ti,
a=from 1.5 to 5,
b=from 0.5 to 2,
c=from 0.5 to 3,
d=from 0 to 2,
e=from 0 to 0.2,
f=from 0 to 1 and
n=a number which is determined by the valency and frequency of the elements in III other than oxygen.

However, multimetal oxides III which are very particularly preferred in accordance with the invention are those of the general formula IV $$Mo_{12}V_{a'}Y^1_{b'}Y^2_{c'}Y^5_{f'}Y^6_{g'}O_{n'} \qquad (IV)$$

where $Y^1$=W and/or Nb, $Y^2$=Cu and/or Ni, $Y^5$=Ca and/or Sr, $Y^6$=Si and/or Al, a'=from 2 to 4, b'=from 1 to 1.5, c'=from 1 to 3, f'=from 0 to 0.5, g'=from 0 to 8 and n'=a number which is determined by the valency and frequency of the elements in IV other than oxygen.

The multimetal oxide active compositions (III) which are suitable in accordance with the invention are obtainable in a manner known per se, for example disclosed in DE-A 4335973 or in EP-A 714700.

In principle, multimetal oxide active compositions suitable for the "acrolein→acrylic acid" step, especially those of the general formula III, can be prepared in a simple manner by obtaining a very intimate, preferably finely divided dry mixture having a composition corresponding to their stoichiometry from suitable sources of their elemental constituents and calcining it at temperatures of from 350 to 600° C. The calcination may be carried out either under inert gas or under an oxidative atmosphere, for example air (mixture of inert gas and oxygen), and alternatively also under a reducing atmosphere (for example mixtures of inert gas and reducing gases such as $H_2$, $NH_3$, CO, methane and/or acrolein or the reducing gases mentioned themselves). The calcination time can be from a few minutes to a few hours and typically decreases with temperature. Useful sources for the elemental constituents of the multimetal oxide active compositions III include those compounds which are already oxides and/or those compounds which can be converted to oxides by heating, at least in the presence of oxygen.

The starting compounds for the preparation of multimetal oxide compositions III can be intimately mixed in dry or in wet form. When they are mixed in dry form, the starting compounds are appropriately used in the form of finely divided powder and subjected to calcining after mixing and, if appropriate, compaction. However, preference is given to intimate mixing in wet form.

This is typically done by mixing the starting compounds with one another in the form of an aqueous solution and/or suspension. Particularly intimate dry mixtures are obtained in the mixing process described when the starting materials are exclusively sources of the elemental constituents in dissolved form. The solvent used is preferably water. Subsequently, the aqueous composition obtained is dried, and the drying process is preferably effected by spray-drying the aqueous mixture at exit temperatures of from 100 to 150° C.

The resulting multimetal oxide compositions, especially those of the general formula III, will be used for the acrolein oxidation shaped to certain catalyst geometries, and the shaping may be effected before or after the final calcination. For example, unsupported catalysts can be prepared from the powder form of the active composition or its uncalcined precursor composition by compacting to the desired catalyst geometry (for example by tableting or extruding), optionally with the addition of assistants, for example graphite or stearic acid as lubricants and/or shaping assistants and reinforcing agents such as microfibers of glass, asbestos, silicon carbide or potassium titanate. Examples of suitable unsupported catalyst geometries are solid cylinders or hollow cylinders having an external diameter and a length of from 2 to 10 mm. In the case of the hollow cylinders, a wall thickness of from 1 to 3 mm is appropriate. The unsupported catalyst may of course also have spherical geometry, in which case the spherical diameter may be from 2 to 10 mm (e.g. 8.2 mm or 5.1 mm).

The pulverulent active composition or its pulverulent precursor composition which is yet to be calcined can of course also be shaped by applying to pre-shaped inert catalyst supports. The coating of the support bodies to prepare the coated catalysts is generally performed in a suitable rotatable vessel, as disclosed, for example, by DE-A 2909671, EP-A 293859 or by EP-A 714700.

To coat the support bodies, the powder composition to be applied is appropriately moistened and is dried again after application, for example by means of hot air. The coating thickness of the powder composition applied to the support body is appropriately selected within the range from 10 to 1000 μm, preferably within the range from 50 to 500 μm and more preferably within the range from 150 to 250 μm.

Useful support materials are customary porous or nonporous aluminum oxides, silicon dioxide, thorium dioxide, zirconium dioxide, silicon carbide or silicates such as magnesium silicate or aluminum silicate. The support bodies may have a regular or irregular shape, although preference is given to regularly shaped support bodies having distinct surface roughness, for example spheres or hollow cylinders with grit layer. Suitable support bodies include substantially nonporous, surface-roughened, spherical supports made of steatite, whose diameter is from 1 to 10 mm or to 8 mm, preferably from 4 to 5 mm. In other words, suitable spherical geometries may have diameters of 8.2 mm or 5.1 mm. However, suitable support bodies also include cylinders whose length is from 2 to 10 mm and whose external diameter is from 4 to 10 mm. In the case of rings as support bodies, the wall thickness is also typically from 1 to 4 mm. Annular support bodies to be used with preference have a length of from 2 to 6 mm, an external diameter of from 4 to 8 mm and a wall thickness of from 1 to 2 mm. Suitable support bodies are also in particular rings of geometry 7 mm×3 mm×4 mm (external diameter×length×internal diameter). The fineness of the catalytically active oxide compositions to be applied to the surface of the support body is of course adapted to the desired coating thickness (cf. EP-A 714700).

Multimetal oxide catalysts which are outstandingly suitable for the "acrolein→acrylic acid" step are also those of DE-A 19815281, especially in case having multimetal oxide active compositions of the general formula I of this document.

Advantageously, unsupported catalyst rings are used for the step from propene to acrolein and coated catalyst rings for the step from acrolein to acrylic acid.

The performance of the partial oxidation of the process according to the invention from propene to acrolein may be carried out with the catalysts described, for example, in a single-zone multiple catalyst tube fixed bed reactor, as described by DE-A 4431957. In this case, reaction gas mixture and heat carrier (heat exchange medium) may be conducted in cocurrent or in countercurrent viewed over the reactor.

The reaction working pressure is in the range from 1 to 6 bar (=absolute pressure; the highest value is at the entrance into the first reaction stage (into the corresponding reactor)) and the overall space velocity on the first fixed catalyst bed of starting reaction gas mixture 1 is preferably from 1500 to 4000 or to 6000 l (STP)/l·h or more. The propene loading (the propene hourly space velocity on the first fixed catalyst bed) is typically from 50 or from 90 to 200 l (STP)/l·h or to 300 l (STP)/l·h or more. Propene loadings above 135 l (STP)/l·h, or ≥140 l (STP)/l·h, or ≥150 l (STP)/l·h, or ≥160 l (STP)/l·h, or ≥170 l (STP)/l·h are particularly preferred in accordance with the invention, since the inventive starting reaction gas mixture 1 fed into reaction stage 1, owing to its composition, causes favorable hotspot behavior (all of the aforementioned applies irrespective of the specific selection of the fixed bed reactor).

The flow to the single-zone multiple catalyst tube fixed bed reactor of the charge gas mixture (starting reaction gas mixture 1) is preferably from above. The heat exchange medium used is appropriately a salt melt, preferably consisting of 60% by weight of potassium nitrate ($KNO_3$) and 40% by weight of sodium nitrite ($NaNO_2$), or of 53% by weight of potassium nitrate ($KNO_3$), 40% by weight of sodium nitrite ($NaNO_2$) and 7% by weight of sodium nitrate ($NaNO_3$).

Viewed over the reactor, salt melt and reaction gas mixture may, as already stated, be conducted either in cocurrent or in countercurrent. The salt melt itself is preferably conducted in a meandering manner around the catalyst tubes.

When the flow of starting reaction gas mixture 1 to the catalyst tubes is from top to bottom, it is appropriate to charge the catalyst tubes with catalyst from bottom to top as follows (for the flow of starting reaction gas mixture 1 from bottom to top, the charge sequence is appropriately reversed):

first, to a length of from 40 to 80 or to 60% of the catalyst tube length, either only catalyst or a mixture of catalyst and inert material, the latter, based on the mixture, making up a proportion by weight of up to 30 or up to 20% by weight (section C);

following this, to a length of from 20 to 50 or to 40% of the total tube length, either only catalyst or a mixture of catalyst and inert material, the latter, based on the mixture, making up a proportion by weight of up to 40% by weight (section B); and finally, to a length of from 10 to 20% of the total tube length, a bed of inert material (section A) which is preferably selected such that it causes a very small pressure drop.

Section C is preferably undiluted.

The aforementioned charge variant is especially appropriate when the catalysts used are those according to Research Disclosure No. 497012 of Aug. 29, 2005, Example 1 of DE-A 10046957 or according to Example 3 of DE-A 10046957 and the inert material used is steatite rings having the geometry 7 mm×7 mm×4 mm (external diameter× height×internal diameter). With respect to the salt bath temperature, the statements of DE-A 4431957 apply correspondingly.

However, the performance of the partial oxidation in the first reaction stage, from propene to acrolein, may also be carried out with the catalysts described, for example, in a two-zone multiple catalyst tube fixed bed reactor, as described by DE-A 19910506, DE-A 102005009885, DE-A 102004032129, DE-A 102005013039, DE-A 102005009891, and DE-A 102005010111. Advantageously in accordance with the invention, the inventive partial oxidation of propene to acrolein is effected as described in EP-A 1 159 244 and most preferably as described in WO 2000/53558, WO 04/085363, WO 2004/085367, WO 2004/085369, WO 2004/085368, WO 04/085362, WO 2004/085369, WO 2007/08287 and WO 2012/049246.

In other words, a partial oxidation of propene to acrolein to be carried out in the first reaction stage can be carried out particularly advantageously over a first fixed catalyst bed having increased propene loading and at least two temperature zones.

In this regard reference is made to documents EP-A 1159244, WO 2000/53558, WO 04/085363, WO 2004/085367, WO 2004/085369, WO 2004/085368, WO 04/085362, WO 2007/08287 and WO 2012/049246 which also are considered an integral part of this document.

The performance of the second step in the case of a two-stage partial oxidation of propene to acrylic acid, i.e. the partial oxidation of acrolein to acrylic acid, may be carried out with the catalysts described, for example, in a one-zone multiple catalyst tube fixed bed reactor as described in DE-A 4431949. In this reaction stage, starting reaction gas mixture 2 and heat carrier can be conducted in cocurrent or in countercurrent viewed over the reactor. In general, the product gas mixture of the preceding inventive propene partial oxidation to acrolein is in principle conducted as such (optionally after intermediate cooling (this may be effected indirectly or directly by, for example, secondary molecular oxygen addition), i.e. without prior secondary component removal, into the second reaction stage, i.e. into the acrolein partial oxidation.

The molecular oxygen required for the second step, the acrolein partial oxidation, may already be present in starting reaction gas mixture 1 for the propene partial oxidation to acrolein. However, it may also be added partly or fully directly to the product gas mixture 1 of the first reaction stage, i.e. the propene partial oxidation to acrolein (this can be effected in the form of oxygen of the purity ≥90% by vol. $O_2$ and ≤90% by vol. $N_2$).

As in the first reaction stage (propene→acrolein), the reaction pressure in the second reaction stage (acrolein→acrylic acid) too is typically in the range from 1 to 6 bar (=absolute pressure; the highest value is at the entrance into the second reaction stage (into the corresponding reactor)) and the total space velocity on the second fixed catalyst bed of starting reaction gas mixture 2 is preferably from 1500 to 4000 or to 6000 l (STP)/l·h or more. The acrolein loading (the acrolein hourly space velocity on the second fixed catalyst bed) is typically from 40 or from 80 to 190 l (STP)/l·h, or to 290 l (STP)/l·h or more. Acrolein loadings above 125 l (STP)/l·h, or ≥130 l (STP)/l·h, or ≥140 l (STP)/l·h, or ≥150 l (STP)/l·h, or ≥160 l (STP)/l·h are particularly preferred, since the starting reaction gas mixture 2 to be fed in accordance with the invention into reaction stage 2, owing to its composition, causes favorable hotspot behavior (all of the aforementioned applies irrespective of the specific selection of the fixed bed reactor).

The flow to the single-zone multiple catalyst tube fixed bed reactor of the charge gas mixture (starting reaction gas mixture 2) is likewise preferably from above. The heat exchange medium used in the second stage too is appropriately a salt melt, preferably consisting of 60% by weight of potassium nitrate ($KNO_3$) and 40% by weight of sodium nitrite ($NaNO_2$), or of 53% by weight of potassium nitrate ($KNO_3$), 40% by weight of sodium nitrite ($NaNO_2$) and 7% by weight of sodium nitrate ($NaNO_3$). Viewed over the reactor, as already stated, salt melt and reaction gas mixture (charge gas mixture) may be conducted either in cocurrent or in countercurrent. The salt melt itself is preferably conducted in a meandering manner around the catalyst tubes.

When the flow of starting reaction gas mixture 2 to the catalyst tubes is from top to bottom, it is appropriate to charge the catalyst tubes with catalyst from bottom to top as follows:

first, to a length of from 50 to 80 or to 70% of the catalyst tube length, either only catalyst or a mixture of catalyst and inert material, the latter, based on the mixture, making up a proportion by weight of up to 30 (or up to 20) % by weight (section C);

following this, to a length of from 20 to 40% of the total tube length, either only catalyst or a mixture of catalyst and inert material, the latter, based on the mixture, making up a proportion by weight of up to 50 or up to 40% by weight (section B); and finally, to a length of from 5 to 20% of the total tube length, a bed of inert material (section A) which is preferably selected such that it causes a very small pressure drop.

Section C is preferably undiluted. As is quite generally the case for the heterogeneously catalyzed gas phase partial oxidation of acrolein to acrylic acid (especially at high acrolein loadings on the fixed catalyst bed and high steam contents of the charge gas mixture), section B may also consist of two successive catalyst dilutions (for the purpose of minimizing hotspot temperature and hotspot temperature sensitivity). From bottom to top, first with up to 30 (or 20) % by weight of inert material and subsequently with from >20% by weight to 50 or to 40% by weight of inert material. Section C is then preferably undiluted.

For flow of starting reaction gas mixture 2 to the catalyst tubes from bottom to top, the catalyst tube charge is appropriately reversed.

The aforementioned charge variant is especially appropriate when the catalysts used are those according to preparation example 5 of DE-A 10046928 or those according to DE-A 19815281 and the inert material used is steatite rings having the geometry 7 mm×7 mm×4 mm or 7 mm×7 mm×3 mm (in each case external diameter×height×internal diameter). With respect to the salt bath temperature, the statements of DE-A 4431949 apply correspondingly.

However, the performance of the partial oxidation of acrolein to acrylic acid may also be carried out with the catalysts described, for example, in a two-zone multiple catalyst tube fixed bed reactor as described in DE-A 19910508, EP-A 1159246, WO 2004/085365, WO 2004/085370, WO 2007/08287, WO 2004/085367, WO 2004/085368 and WO 2004/085369. Also in the case in which an acrolein partial oxidation as described above is carried out as the second stage of a two-stage propene partial oxidation to acrylic acid in a two-zone multiple catalyst tube fixed bed reactor, the charge gas mixture (starting reaction gas mixture 2) will appropriately be obtained directly by using the product gas mixture of the partial oxidation directed to the first step (propene→acrolein) (optionally after indirect or direct (for example by supplying secondary oxygen of the purity ≥90% by vol. $O_2$ and ≤10% by vol. $N_2$) intermediate cooling thereof) (as has already been described above). The oxygen required for the acrolein partial oxidation is preferably added between the first reaction stage and the second reaction stage in the form of (secondary) oxygen of the purity ≥90% by vol. $O_2$ and ≤10% by vol. $N_2$, preferably of the purity ≥95% by vol. $O_2$ and ≤5% by vol. $N_2$, or of the purity 98% by vol. $O_2$ and ≤2% by vol. $N_2$, or of the purity ≥99% by vol. $O_2$ and ≤1% by vol. $N_2$, or of the purity 99.4% to 99.9% by vol. $O_2$ and 0.1 to 0.6% by vol. $N_2$, or of the purity 99.5% to 99.8% by vol. $O_2$ and of from 0.2 to 0.5% by vol. $N_2$ and, for example, added directly to the product gas mixture 1 of the first step of the two-stage partial oxidation (propene→acrolein). However, it may also, as described above, already be present in the starting reaction gas mixture 1 for the first reaction stage.

In a two-stage partial oxidation of propene to acrylic acid with direct further use of the product gas mixture 1 of the first step of the partial oxidation to charge the second step of the partial oxidation, two one-zone multiple catalyst tube fixed bed reactors (at high reactant loading on the catalyst bed, as is quite generally the case, preference is given to countercurrent mode between reaction gas and salt bath (heat carrier) viewed over the tube bundle reactor) or two two-zone multiple catalyst tube fixed bed reactors will generally be connected in series. A mixed series connection (one-zone/two-zone or vice versa) is also possible.

Advantageously in accordance with the invention, the inventive partial oxidation of acrolein to acrylic acid is effected as described in DE-A 19910508, EP-A 1159246, WO 2000/53558, WO 2004/085365, WO 2004/085370, WO 2007/08287, WO 2004/085367, WO 2004/085368 and WO 2004/085369.

In other words, a partial oxidation of acrolein to acrylic acid to be carried out in the second reaction stage can be carried out particularly advantageously over a second fixed catalyst bed having increased acrolein loading and at least two temperature zones.

In this regard reference is made to the documents DE-A 19910508, EP-A 1159246, WO 2000/53558, WO 2004/085365, WO 2004/085370, WO 2007/08287, WO 2004/085367, WO 2004/085368 and WO 2004/085369 which also are considered an integral part of this document.

Between the reactors may be disposed an intermediate cooler which optionally may comprise inert beds which can perform a filter function. The salt bath temperature of multiple catalyst tube reactors for the first step of the two-stage partial oxidation of propene to acrylic acid is generally from 250 to 500° C. The salt bath temperature of multiple catalyst tube reactors for the second step of the partial oxidation of propene to acrylic acid, the partial oxidation of acrolein to acrylic acid, is usually from 200 to 450° C. The reaction temperature is regulated by means of the salt bath temperature. In addition, the heat exchange media (preferably salt melts) are normally conducted through the relevant multiple catalyst tube fixed bed reactors in such amounts that the difference between their input temperature and their output temperature is generally 5° C. (in countercurrent as well as in cocurrent operation). As already mentioned, both steps of the partial oxidation of propene to acrylic acid may also be implemented in one two zone reactor ("single reactor") over one fixed catalyst bed in which the multimetal oxide changes its composition along the reaction tubes from Mo, Bi and Fe containing to Mo and V containing. The salt bath temperature in each reaction zone will be individually adjusted.

Overall, a tube bundle reactor within which the catalyst charge changes appropriately along the individual catalyst tubes with completion of the first reaction step (such two-stage propene partial oxidations in a single reactor are taught, for example, by EP-A 911 313, EP-A 979 813, EPA-990 636 and DE-A 28 30 765) forms the simplest implementation form of the two oxidation stages for the two steps of the partial oxidation from propene to acrylic acid. Optionally, the charge of the catalyst tubes with catalyst is interrupted by an inert material bed.

However, preference is given to implementing the two oxidation stages in the form of two reactors connected in series such as two thermoplate reactors connected in series or two tube bundle reactors connected in series. The latter may be disposed in one reactor, in which case the transition from one tube bundle to the other tube bundle is formed by a bed of inert material which is not accommodated in the catalyst tube (and is appropriately accessible on foot). While the catalyst tubes are generally flowed around by a heat carrier, this does not reach an inert material bed accommodated as described above. Advantageously, the two catalyst tube bundles are therefore accommodated in spatially separate reactors. In general, an intermediate cooler is disposed between the two tube bundle reactors in order to reduce any acrolein post-combustion proceeding in the product gas mixture 1 which leaves the first oxidation stage (reactor).

Generally the fixed catalyst bed in case of each of the two reaction stages in the reaction tubes of the respective tube bundle reactor is charged in such a manner and the reactor design designed so, that in case during operation of the production the temperature of the respective salt bath is at any time increased by +1° C. everywhere within the respective catalyst bed the temperature increase within the catalyst bed is ≤+9° C., preferably ≤+7° C., better ≤+5° C. or ≤+3° C., but ≥0° C. (see also e.g. U.S. Pat. No. 8,618,336).

In the process according to the invention, metering of, for example, cold oxygen source to the product gas mixture 1 of the first partial oxidation stage can also bring about cooling thereof by a direct route before it is used further as a constituent of a starting reaction gas mixture 2 for the second partial oxidation stage.

At this point it should be noted that applicant surprisingly has found that the catalysts applied in the two reaction stages of the invention process are obviously not capable of catalyzing the combustion of by-product CO with $O_2$ contained in the reaction gas mixtures to yield $CO_2$. This fact makes it possible to enrich CO in the invention process by means of a comparatively high recycle gas ratio K (K=(mass flow of the recycle gas stream P)/(total mass flow M of residual gas mixture R continuously conducted out of the separating zone)) and to generate off-gas streams O which are rich in CO. Further using such off-gas rich in CO for production of synthesis gas is possible in a particular simple way by just mixing the off-gas as such into a synthesis gas produced elsewhere and making use of the resulting mixture as new synthesis gas for synthesis purposes.

By conversion $U^X$ (mol %) of a compound X in a reaction zone in this document it is meant the percentage of the molar amount of said compound X fed to the relevant reaction zone, which in the reaction zone is transformed into the target product and by-products.

By selectivity $S^Y$ (mol %) of the formation of a compound Y in a reaction zone due to conversion of compound X in said reaction zone in this document it is meant the molar amount of compound Y formed in the reaction zone expressed as percentage of the molar amount of the compound X converted in the reaction zone.

By yield $A^Y$ (mol %) of product Y achieved in aforesaid reaction zone due to conversion of compound X in said reaction zone in this document it is meant the product [$U^X$ (mol %)×$S^Y$ (mol %)] divided by 100 mol %.

Product gas mixture 1 respectively product gas mixture 2 contain substantially the target product acrolein (accompanied by small amounts of by-product acrylic acid) respectively acrylic acid (accompanied by small amounts of by-product acrolein), steam (formed as by-product and/or used additionally as inert diluent gas), any unconverted molecular oxygen (as already stated herein, with a view to the lifetime of the catalysts used, it is favorable when the content of molecular oxygen contained in the respective product gas mixture is still >0% by vol., such as e.g. 1.5% by vol. to 4% by vol.) and also other by-products or secondary components having as pure compounds at a working pressure of 1 bar boiling points higher ("high boilers") or lower ("low boilers") than the target product such as CO, $CO_2$, lower aldehydes and/or lower alkene carboxylic acids (e.g. formaldehyde, acetaldehyde, propionaldehyde, formic acid, acetic acid and propionic acid), maleic anhydride, benzaldehyde, aromatic carboxylic acids and aromatic carboxylic anhydrides such as phthalic anhydride and benzoic acid, propane as possible companion of propene or used additionally as inert diluent gas and other optionally co-used inert diluent gases such as $N_2$ and one or more than one hydrocarbon from the group consisting of methane, ethane, n-butane, isobutane and ethene.

The separation of the respective target product (acrolein or acrylic acid) from the respective product gas mixture resulting in the respective heterogeneously catalyzed partial gas phase oxidation (from product gas mixture 1 or product gas mixture 2) is carried out in the invention process in a corresponding separation zone through transferring at least 95 mol % (preferably at least 96 mol %, more preferably at least 97 mol %, better at least 98 mol % and best at least 99 mol % (however normally not more than 99.8 mol %) of the respective target product contained in the respective product gas mixture from the gaseous phase into the liquid phase. This can be done as known from the prior art processes. In general in these processes the respective prior product gas mixture on entry into the separating zone will initially be subjected to indirect and/or direct cooling (such cooling can already cause a separation of constituents of the target product containing product gas mixture continuously transported into the separating zone, which have as pure compounds at a working pressure of 1 bar a boiling point above the boiling point of the target product, from said product gas mixture). As in the prior art, transferring the target product present in the product gas mixture which has been cooled in this way or present in uncooled product gas mixture into the liquid phase preferably will be carried out by absorption into a liquid absorbent and/or by condensation (preferably fractional condensation) as e.g. described in the respective prior art references cited in WO 2007/074045 and WO 2007/060036. Useful absorbents for substantially both target products are either water or aqueous solutions, or high boiling organic solvents. Subsequent workup of the resulting, the desired target product containing, liquid phase within the separating zone through application of thermal separation processes such as stripping, distillation, rectification (including azeotropic rectification respectively distillation), extraction and/or crystallization (all these separation processes are part of the separating zone, belong to the separating zone) finally yields the target product in its desired purity which normally is continuously withdrawn from the separation (separating) zone into which the respective product mixture is also continuously fed. During the processing of the liquid phase containing the respective target product and/or during the cooling of the respective product gas mixture from the target product and from the low boilers separated high boilers expediently are also continuously led out of the separating zone. Diacrylic acid and polyacrylic acids (both Michael adducts) being among the high boilers subsequently may by be cracked by exposure to elevated temperature and the acrylic acid monomers resulting therefrom returned into the separating zone.

Those constituents of the target product containing product gas mixture continuously transported into the separating zone which have as pure compounds at a working pressure of 1 bar a boiling point below the boiling point of pure water remain in the separating zone mainly in the gaseous phase (in case of water itself and of constituents having under corresponding conditions a boiling point above that of pure water, the specific working conditions applied for transferring the target product from the respective product gas mixture into the liquid phase determine the respective amount that remains in the residual gas mixture) and are contained in a residual gas mixture R of which a total mass flow M is continuously conducted out of the separating zone. Especially those compounds contained in the product gas mixture continuously transported into the separating zone, which have as pure compounds at a working pressure of 1 bar a boiling point below 250 K (such compounds above all include the respective components of the inert diluent gas applied), are a major portion of the residual gas mixture R. At least 95 mol % of the total molar amount of those compounds being components of the product gas mixture continuously transported into the separating zone and having as pure compounds at a working pressure of 1 bar a boiling point below 250 K are under the applicable transfer conditions (under stationary operating conditions) finally contained in the total mass stream M of the residual gas mixture R continuously conducted out of the separating zone.

In practice, both the absorptive and/or the condensative conversion of the respective target product from the gaseous to the liquid phase are typically undertaken in separation columns comprising separating internals (for enlarging the mass transfer surface area). Useful separating internals include all known internals. In other words, it is possible to use either trays such as bubble-cap trays, dual-flow trays or valve trays, random packings, for example Raschig rings, or structured packings, for example Sulzer packings, as separating internals. The respective product gas mixture is normally conducted into the separation column ascending from the bottom upward. In the context of an absorptive condensation, the absorbent is normally moved (conducted) from the top downward in the separation column. The liquid absorbate running downward essentially forms the liquid phase comprising the target product (and secondary components having a higher and similar boiling point). It will be continuously be withdrawn from the lower part of the absorption column by side withdrawal (preferred) and/or withdrawal from the sump. In the fractional condensation, the relatively high-boiling constituents of the product gas mixture (including e.g. target product acrylic acid) are condensed ascending into it. The condensate comprising enriched target product, particularly acrylic acid, is generally conducted out of the condensation column via side draw removal and essentially forms the liquid phase comprising the target product (and secondary components having a higher and similar boiling point). It will be appreciated that absorption and condensation may also be employed superimposed on one another. This is, for example, always the case when heat is withdrawn additionally from the system in the absorption process by direct and/or indirect cooling.

Preference is given to conducting the respective product gas mixture into the separation column with a temperature reduced by indirect cooling, or by direct cooling or by direct and indirect cooling. Advantageously the indirect cooling is undertaken in indirect heat exchangers in a manner known per se, while direct cooling is typically effected by spraying e.g. absorbent precooled in a quench apparatus or precooled bottoms liquid from the separation column into the respective product gas mixture. A common feature of the above-described absorptive and/or condensative processes (separation processes) is that, at the top of the particular separation column comprising separating internals, into whose lower section the respective product gas mixture, preferably after preceding direct and/or indirect cooling thereof as described, is typically conducted, a residual gas stream remains which comprises mainly those constituents of the product gas mixture whose boiling point at standard pressure (1 bar) is <250 K (i.e. the constituents which are difficult to condense or else volatile).

These include, for example, molecular nitrogen used additionally in the partial oxidation as an inert diluent gas, excess molecular oxygen remaining relative to the reaction stoichiometry in the partial oxidation, carbon oxides (CO and/or $CO_2$) formed as a by-product or used additionally as inert diluent gases in starting reaction gas mixture 1, but also propene unconverted in the partial oxidation and optionally co-used diluent gases such as methane, natural gas, ethane, ethene and propane. In favorable cases, this remaining gas may already be the residual gas mixture R. However, aforesaid remaining residual gas stream may still contain noticeable quantities of steam. This content of $H_2O$, where desired, easily may be reduced by applying additional condensation measures (e.g. corresponding indirect cooling). The resulting condensate in literature usually is designated as "acid water" (it typically contains some target product acrylic acid and/or carboxylic acid by-products such as acetic acid). In such aforesaid cases the gas stream remaining after such additional condensation then is the residual gas mixture R.

The composition C of as described resulting residual gas mixture R normally is
    from 0.01 to 1% by volume of propene,
    from 1 to 10% by volume of molecular oxygen,
    from 0.5 to 25% by volume of water,
    from 0 to 20% by volume of molecular nitrogen,
    from 0.5 to 40% by volume of carbon monoxide,
    from 1 to 75% by volume of carbon dioxide,
    from 0 to 92% by volume of one or more than one
        hydrocarbon selected from the group consisting of
        methane, ethane, propane, n-butane, isobutane and
        ethene (preferably essentially only propane), and
    from 0.01 to 5% by volume of other compounds including
        but not limited to acrolein and/or acrylic acid.

With advantage, not the total amount of the stream of residual gas mixture R will be conducted out of the separating zone. This is because partial quantities of the residual gas mixture R e.g. advantageously may be used for stripping target product (e.g. acrylic acid) from liquid phases containing target product (e.g. acrylic acid) such as acid water or being produced during further purification of the target product containing absorbate or condensate which is continuously withdrawn from the separating column. Subsequently the target product laden stripping gas preferably will be returned again into the separating column.

However, from the total mass flow M of residual gas mixture R which will be continuously conducted out of the separating zone a partial stream (=gaseous stream) having the same composition as the residual gas mixture R will continuously be recycled into the first reaction stage as feed stream for preparing the stream of starting reaction gas mixture 1 and the difference between the total mass flow M of residual gas mixture R continuously conducted out of the separating zone and the mass flow of the recycle gaseous stream P will continuously discharged of the production process as off-gas stream O, and all of the aforesaid with the proviso that
    a) the mass flow of the recycle gaseous stream P is at least
        65% but not more than 99.5% of the total mass flow M
        of residual gas mixture R continuously conducted out
        of the separating zone, and b) the mass flow of the off-gas stream O is not more than 35% but at least 0.5% of the total mass flow M of residual gas mixture R continuously conducted out of the separating zone.

For the invention process applicable absorptive and/or condensative processes of transferring target product acrolein respectively target product acrylic acid from similar product gas mixtures into the liquid phase are e.g. described in detail in the documents US-A 3433840, WO 2014/22044, WO 2003/068721 and DE 10213998 (all directed to the absorption of acrolein by aqueous absorbents), WO 2008/090190 and WO 2013/139590 (both directed to fractional condensation of acrylic acid), WO 2011/000808 and DE-A 10336386 (both directed to absorption of acrylic acid through high boiling organic solvents) and DE-A 3429391, U.S. Pat. Nos. 7,183,428 and 5,315,037 (all directed to absorption of acrylic acid by aqueous absorbents).

The further removal of the respective target product from the liquid phase up to the desired degree of purity of the target product can be undertaken by a wide variety of different combinations of a wide variety of different thermal separation processes. These may be, for example, combinations of extractive, desorptive, crystallizative, rectificative, azeotropically distillative, azeotropically rectificative, distillative and/or stripping processes. All these processes are part of the separating zone and advantageously linked to the separating column through appropriate recycle streams into said column.

It will be appreciated that all process steps performed in the separating zone are carried out with inhibition of undesired polymerization of the respective target product. The procedure may be as described in the prior art cited. An outstanding position among the entirety of the available acrylic acid process stabilizers is assumed by dibenzo-1,4-thiazine (PTZ=phenothiazine), 4-hydroxy-2,2,6,6-tetramethylpiperidine-1-oxyl (4-OH-TEMPO) and p-methoxyphenol (MEHQ). They may, for example, each alone or in pairs or as a three-substance mixture, be part of the acrylic acid-containing liquid phase. Hydroquinone is an excellent inhibitor for acrolein. Typically, the total amount of polymerization inhibitors in the respective liquid phases, based on target product present therein, is from 0.001 to 2% by weight. Molecular oxygen dissolved in the relevant liquid phases usually additionally helps to promote the polymerization inhibition.

FIG. 1 (FIG. 1) of this document shows a schematic block diagram of the invention production process for production of acrylic acid as target product. The reference numerals of FIG. 1 are defined as follows:

1: optional stream of steam
2: optional streams of one or more than one hydrocarbon selected from the group consisting of methane, natural gas, ethane, propane, n-butane, isobutane and ethane
3: stream of propene feedstock
4: stream of source of molecular oxygen
5: starting reaction gas mixture 1
6: first reaction stage
7: product gas mixture 1
8: optional stream of secondary gas
9: starting reaction gas mixture 2
10: second reaction stage
11: product gas mixture 2
12: separating zone
13: stream of target product acrylic acid in its desired purity (produced through work-up of liquid phases 15 within the separating zone) e.g. fed into a storage tank 14: off-gas stream O discharged of the production process and fed to syngas production
15: liquid phases into which target product acrylic acid has been transferred from production gas mixture 2
16: residual gas mixture R
17: recycling gaseous stream P
18: optional streams of residual gas mixture R circled within the separating zone
17+14: total mass flow M of residual gas mixture R continuously conducted out of the separating zone
19: high boilers (e.g. separated from target product acrylic acid through work-up of liquid phases 15 within the separating zone) led out of the separating zone Thus, the present application encompasses, more particularly, the following embodiments:

1. A process for the continuous production of either acrolein or acrylic acid as the target product from propene comprising under stationary operating conditions A) as an obligatory measure continuously passing in a first reaction stage a stream of a starting reaction gas mixture 1 consisting of
   from 2 to 15% by volume of propene,
   from 2.4 to 37.5% by volume of molecular oxygen,
   from 0.5 to 20% (preferably 0 to 10%) by volume of water,
   from 0 to 20% by volume of molecular nitrogen,
   from 0.5 to 30% by volume of carbon monoxide,
   from 1 to 65% by volume of carbon dioxide,
   from 0 to 80% by volume of one or more than one hydrocarbon selected from the group consisting of methane, ethane, propane, n-butane, isobutane and ethene, and
   from >0 to 5% by volume of other compounds including but not limited to acrolein and/or acrylic acid,
   and containing
      the molecular oxygen and the propene in a molar $O_2$:propene ratio ranging from 1.2 to 2.5,
      the carbon dioxide and the carbon monoxide in a molar $CO_2$:CO ratio ranging from 1 to 4,
      and the molecular oxygen and the molecular nitrogen in a molar $O_2$:$N_2$ ratio of at least 0.5,
   at a reaction temperature of from 250° C. to 500° C. and a working pressure of from 1 bar to 6 bar through a first fixed catalyst bed comprising shaped catalyst bodies whose active mass is at least one multimetal oxide containing molybdenum (Mo), bismuth (Bi) and iron (Fe) in such a way, that the propene conversion on single pass is from 80 mol % to 99 mol % and the accompanying selectivity $S^A$ of the formation of the target product acrolein is from 70 mol % to 99 mol % to obtain a stream of a the target product acrolein containing product gas mixture 1 leaving the first reaction stage,
   and, B) in case of acrylic acid being the target product,
   optionally reducing the temperature of the product gas mixture leaving the first reaction stage by direct, indirect or direct and indirect cooling,
   optionally adding secondary gas to said product gas mixture in the form of molecular oxygen, or inert gas, or molecular oxygen and inert gas, and
   subsequently continuously passing in a second reaction stage a stream of the thus resulting starting reaction gas mixture 2 consisting of from 2 to 15% by volume of acrolein, from 1 to 45% by volume of molecular oxygen, from 2 to 30% by volume of water, from 0 to 20% (preferably 0 to 10%) by volume of molecular nitrogen, from 0.5 to 30% by volume of carbon monoxide, from 1 to 65% by volume of carbon dioxide, from 0 to 80% by volume of one or more than one hydrocarbon selected from the group consisting of methane, ethane, propane, n-butane, isobutane and ethene, and from >0 to 5% by volume of other compounds including but not limited to propene and/or acrylic acid, and containing the molecular oxygen and the acrolein in a molar $O_2$:acrolein ratio ranging from 0.5 to 3, the carbon dioxide and the carbon monoxide in a molar $CO_2$:CO ratio ranging from 1 to 4, and the molecular oxygen and the molecular nitrogen in a molar $O_2$:$N_2$ ratio of at least 0.25, at a reaction temperature of from 200° C. to 450° C. and a working pressure of from 1 bar to 6 bar through a second fixed catalyst bed comprising shaped catalyst bodies whose active mass is at least one multimetal oxide containing molybdenum (Mo) and vanadium (V) in such a way, that the acrolein conversion on single pass is from 95 mol % to 99.99 mol % and the accompanying selectivity $S^{AA}$ of the formation of the target product acrylic acid assessed over both reaction stages and based on converted propene is from 80 mol % to 99.9 mol % to obtain a stream of a the target product acrylic acid containing product gas mixture 2 leaving the second reaction stage, and C) either continuously transporting the stream of the target product acrolein containing product gas mixture 1 or the stream of the target product acrylic acid containing product gas mixture 2 into a separating zone and separating in the separating zone the respective target product from the respective product gas mixture through transferring at least 95 mol % of the respective target product contained in the respective product gas mixture from the gaseous phase into the liquid phase and continuously conducting out of the separating zone a total mass flow M of a residual gas mixture R which contains, of the total molar amount of those compounds contained in the product gas mixture continuously transported into the separating zone, which have as pure compounds at a working pressure of 1 bar a boiling point below 250 K, at least 95 mol % and D) recycling as gaseous stream P having the same composition as the residual gas mixture R a partial stream of the total mass flow M of residual gas mixture R continuously conducted out of the separating zone into the first reaction stage 1 as feed stream for preparing the stream of the starting reaction gas mixture 1 which shall contain the gaseous stream P, and discharging of the production process as off-gas stream O, having the same composition as the residual gas mixture R, the difference between the total mass flow M of residual gas mixture R continuously conducted out of the separating zone and the mass flow of recycle gaseous stream P, wherein a) the mass flow of the recycle gaseous stream P is at least 65% but not more than 99.5% of the total mass flow M of residual gas mixture R continuously conducted out of the separating zone, b) the mass flow of the off-gas stream O is not more than 35% but at least 0.5% of the total mass flow M of residual gas mixture R continuously conducted out of the separating zone, and c) the composition C of the residual gas mixture R is from 0.01 to 1% by volume of propene, from 1 to 10% by volume of molecular oxygen, from 0.5 to 25% by volume of water, from 0 to 20% (preferably 0 to 10%) by volume of molecular nitrogen, from 0.5 to 40% by volume of carbon monoxide, from 1 to 75% by volume of carbon dioxide, from 0 to 92% by volume of one or more than one hydrocarbon selected from the group consisting of methane, ethane, propane, n-butane, isobutane and ethene, and from 0.01 to 5% by volume of other compounds including but not limited to acrolein and/or acrylic acid.

2. The process according to embodiment 1, wherein the reaction temperature in the first reaction stage is 280° C. to 480° C.

3. The process according to embodiment 1, wherein the reaction temperature in the first reaction stage is 290° C. to 470° C.

4. The process according to embodiment 1, wherein the reaction temperature in the first reaction stage is 300° C. to 450° C.

5. The process according to any of embodiments 1 to 4, wherein the working pressure in the first reaction stage is 1 to 5 bar.

6. The process according to any of embodiments 1 to 4, wherein the working pressure in the first reaction stage is 1 to 4 bar.

7. The process according to any of embodiments 1 to 4, wherein the working pressure in the first reaction stage is 1 to 3.5 bar.

8. The process according to any of embodiments 1 to 7, wherein the propene conversion on single pass in the first reaction stage is in the range from 85 mol % to 99 mol %.

9. The process according to any of embodiments 1 to 7, wherein the propene conversion on single pass in the first reaction stage is in the range from 90 mol % to 99 mol %.

10. The process according to any of embodiments 1 to 7, wherein the propene conversion on single pass in the first reaction stage is in the range from 92 mol % to 98.5 mol %.

11. The process according to any of embodiments 1 to 10, wherein the accompanying selectivity $S^A$ of the formation of the target product acrolein in the first reaction stage is from 75 mol % to 99 mol %.

12. The process according to any of embodiments 1 to 10, wherein the accompanying selectivity $S^A$ of the formation of the target product acrolein in the first reaction stage is from 80 mol % to 99 mol %.

13. The process according to any of embodiments 1 to 12, wherein the reaction temperature in the second reaction stage is 210° C. to 430° C.

14. The process according to any of embodiments 1 to 12, wherein the reaction temperature in the second reaction stage is 220° C. to 410° C.

15. The process according to any of embodiments 1 to 12, wherein the reaction temperature in the second reaction stage is 230° C. to 390° C.

16. The process according to any of embodiments 1 to 15, wherein the working pressure in the second reaction stage is from 1 to 5 bar.

17. The process according to any of embodiments 1 to 15, wherein the working pressure in the second reaction stage is from 1 to 4 bar.

18. The process according to any of embodiments 1 to 15, wherein the working pressure in the second reaction stage is from 1 to 3.5 bar.

19. The process according to any of embodiments 1 to 18, wherein the acrolein conversion on single pass in the second reaction stage is in the range from 97 mol % to 99.95 mol %.

20. The process according to any of embodiments 1 to 18, wherein the acrolein conversion on single pass in the second reaction stage of the inventive process is in the range from 98 mol % to 99.9 mol %.

21. The process according to any of embodiments 1 to 18, wherein the acrolein conversion on single pass in the second reaction stage of the inventive process is in the range from 99 mol % to 99.8 mol %.

22. The process according to any of embodiments 1 to 21, wherein the accompanying selectivity $S^{AA}$ of the formation of the target product acrylic acid assessed over both reaction stages and based on converted propene is from 83 mol % to 99 mol %.

23. The process according to any of embodiments 1 to 21, wherein the accompanying selectivity $S^{AA}$ of the formation of the target product acrylic acid assessed over both reaction stages and based on converted propene is from 85 mol % to 99 mol %.

24. The process according to any of embodiments 1 to 21, wherein the accompanying selectivity $S^{AA}$ of the formation of the target product acrylic acid assessed over both reaction stages and based on converted propene is from 87 mol % to 99 mol %.

25. The process according to any of embodiments 1 to 24, wherein the following conditions are simultaneously fulfilled:
   a) starting reaction gas mixture 1 contains from 3 to 10% by volume propene, from 3.9 to 23% by volume molecular oxygen and contains the molecular oxygen and the propene in a molar $O_2$:propene ratio ranging from 1.3 to 2.1; and (only in case acrylic acid is the target product; otherwise b) is not applicable)
   b) starting reaction gas mixture 2 contains from 3 to 10% by volume acrolein, from 1.8 to 25% by volume of molecular oxygen and contains the molecular oxygen and the acrolein in a molar $O_2$:acrolein ratio ranging from 0.6 to 2.5.

26. The process according to any of embodiments 1 to 24, wherein the following conditions are simultaneously fulfilled:
   a) starting reaction gas mixture 1 contains from 4 to 9% by volume propene, from 5.6 to 19.8% by volume molecular oxygen and contains the molecular oxygen and the propene in a molar $O_2$:propene ratio ranging from 1.4 to 2.2; and (only in case acrylic acid is the target product; otherwise b) is not applicable)
   b) starting reaction gas mixture 2 contains from 4 to 9% by volume acrolein, from 2.8 to 18% by volume of molecular oxygen and contains the molecular oxygen and the acrolein in a molar $O_2$:acrolein ratio ranging from 0.7 to 2.0.

27. The process according to any of embodiments 1 to 24, wherein the following conditions are simultaneously fulfilled:
   a) starting reaction gas mixture 1 contains from 5 to 8% by volume propene, from 7.5 to 16.8% by volume molecular oxygen and contains the molecular oxygen and the propene in a molar $O_2$:propene ratio ranging from 1.5 to 2.1; and (only in case acrylic acid is the target product; otherwise b) is not applicable)
   b) starting reaction gas mixture 2 contains from 4.5 to 8% by volume acrolein, from 3.6 to 12% by volume of molecular oxygen and contains the molecular oxygen and the acrolein in a molar $O_2$:acrolein ratio ranging from 0.8 to 1.5.

28. The process according to any of embodiments 1 to 27, wherein the first fixed catalyst bed of the first reaction stage comprises catalyst bodies whose active mass is at least one multimetal oxide of the general formula I $$Mo_{12}Bi_aFe_bX^1_cX^2_dX^3_eX^4_fO_n \qquad (I)$$

in which the variables are each defined as follows:
$X^1$=nickel and/or cobalt,
$X^2$=thallium, an alkali metal and/or an alkaline earth metal,
$X^3$=zinc, phosphorus, arsenic, boron, antimony, tin, cerium, lead and/or tungsten,
$X^4$=silicon, aluminum, titanium and/or zirconium,
a=from 0.5 to 5,
b=from 0.01 to 5,
c=from 0 to 10,
d=from 0 to 2,
e=from 0 to 8,
f=from 0 to 10 and
n=a number which is determined by the valency and frequency of the elements in I other than oxygen.

29. The process according to any of embodiments 1 to 27, wherein the first fixed catalyst bed of the first reaction stage comprises catalyst bodies whose active mass is at least one multimetal oxide of the general formula I $$Mo_{12}Bi_aFe_bX^1_cX^2_dX^3_eX^4_fO_n \qquad (I)$$

in which the variables are each defined as follows:
$X^1$=nickel and/or cobalt,
$X^2$=thallium, an alkali metal and/or an alkaline earth metal,
$X^3$=zinc, phosphorus, arsenic, boron, antimony, tin, cerium, lead and/or tungsten,
$X^4$=silicon, aluminum, titanium and/or zirconium,
a=from 0.5 to 5,
b=from 2 to 4,
c=from 3 to 10,
d=from 0.02 to 2,
e=from 0 to 5,
f=from 0 to 10 and
n=a number which is determined by the valency and frequency of the elements in I other than oxygen.

30. The process according to any of embodiments 1 to 27, wherein the first fixed catalyst bed of the first reaction stage comprises catalyst bodies whose active mass is at least one multimetal oxide of the general formula II $$[Bi_{a''}Z^2_{b''}O_{x''}]_{p''}[Z^2_{12}Z^3_{c''}Z^4_{d''}Fe_{e''}Z^5_{f''}Z^6_{g''}Z^7_{h''}O_{y''}]_{q''} \qquad (II)$$

in which the variables are each defined as follows:
$Z^2$=molybdenum or molybdenum and tungsten,
$Z^3$=nickel and/or cobalt,
$Z^4$=thallium, an alkali metal and/or an alkaline earth metal, $Z^5$=phosphorus, arsenic, boron, antimony, tin, cerium and/or lead, $Z^6$=silicon, aluminum, titanium and/or zirconium, $Z^7$=copper, silver and/or gold, a″=from 0.1 to 1, b″=from 0.2 to 2, c″=from 3 to 10, d″=from 0.02 to 2, e″=from 0.01 to 5, f″=from 0 to 5, g″=from 0 to 10, h″=from 0 to 1, x″,y″=numbers which are determined by the valency and frequency of the elements in II other than oxygen, p″,q″=numbers whose p″/q″ ratio is from 0.1 to 5, comprising three-dimensional regions of the chemical composition $Bi_{a''}Z^2_{b''}O_{x''}$ which are delimited from their local environment owing to their different composition from their local environment, and whose maximum diameter (longest direct line passing through the center of the region and connecting two points on the surface (interface) of the region) is from 1 nm to 100 μm.

31. The process according to embodiment 30, wherein in the general formula II $Z^2_{b''}$=(tungsten)$_{b''}$ and $Z^2_{12}$=(molybdenum)$_{12}$.

32. The process according to any of embodiments 1 to 31, wherein the second fixed catalyst bed of the second reaction stage comprises catalyst bodies whose active mass is at least one multimetal oxide of the general formula III $$Mo_{12}V_aX^1_bX^2_cX^3_dX^4_eX^5_fX^6_gO_n \qquad (III)$$

in which the variables are each defined as follows:

$X^1$=W, Nb, Ta, Cr and/or Ce, $X^2$=Cu, Ni, Co, Fe, Mn and/or Zn, $X^3$=Sb and/or Bi, $X^4$=one or more alkali metals, $X^5$=one or more alkaline earth metals, $X^6$=Si, Al, Ti and/or Zr, a=from 1 to 6, b=from 0.2 to 4, c=from 0.5 to 18, d=from 0 to 40, e=from 0 to 2, f=from 0 to 4, g=from 0 to 40 and n=a number which is determined by the valency and frequency of the elements in III other than oxygen.

33. The process according to embodiment 32, wherein the variables of the general formula III are each defined as follows:

$X^1$=W, Nb and/or Cr, $X^2$=Cu, Ni, Co and/or Fe, $X^3$=Sb, $X^4$=Na and/or K, $X^5$=Ca, Sr and/or Ba, $X^6$=Si, Al and/or Ti, a=from 1.5 to 5, b=from 0.5 to 2, c=from 0.5 to 3, d=from 0 to 2, e=from 0 to 0.2, f=from 0 to 1, g=from 0 to 40 and n=a number which is determined by the valency and frequency of the elements in III other than oxygen.

34. The process according to any of embodiments 1 to 31, wherein the second fixed catalyst bed of the second reaction stage comprises catalyst bodies whose active mass is at least one multimetal oxide of the general formula IV $$Mo_{12}V_{a'}Y^1_{b'}Y^2_{c'}Y^5_{f'}Y^6_{g'}O_{n'} \qquad (IV)$$

in which the variables are each defined as follows:

$Y^1$=W and/or Nb, $Y^2$=Cu and/or Ni, $Y^5$=Ca and/or Sr, $Y^6$=Si and/or Al, a′=from 2 to 4, b′=from 1 to 1.5, c′=from 1 to 3, f′=from 0 to 0.5, g′=from 0 to 8 and n′=a number which is determined by the valency and frequency of the elements in IV other than oxygen.

35. The process according to any of embodiments 1 to 34, wherein the propene hourly space velocity on the first fixed catalyst bed in the first reaction stage is from 50 to 300 1 (STP)/l·h.

36. The process according to any of embodiments 1 to 34, wherein the propene hourly space velocity on the first fixed catalyst bed in the first reaction stage is from 90 to 200 1 (STP)/l·h.

37. The process according to any of embodiments 1 to 34, wherein the propene hourly space velocity on the first fixed catalyst bed in the first reaction stage is from 135 to 200 1 (STP)/l·h.

38. The process according to any of embodiments 1 to 37, wherein the acrolein hourly space velocity on the second fixed catalyst bed in the second reaction stage is from 40 to 290 1 (STP)/l·h.

39. The process according to any of embodiments 1 to 37, wherein the acrolein hourly space velocity on the second fixed catalyst bed in the second reaction stage is from 80 to 190 1 (STP)/l·h.

40. The process according to any of embodiments 1 to 37, wherein the acrolein hourly space velocity on the second fixed catalyst bed in the second reaction stage is from 125 to 190 1 (STP)/l·h.

41. The process according to any of embodiments 1 to 40, wherein shaped catalyst bodies of the first fixed catalyst bed in the first reaction stage are unsupported rings and of the second fixed catalyst bed are coated rings.

42. The process according to embodiment 41, wherein the unsupported rings have an external diameter of 2 to 10 mm, a length of 2 to 10 mm and a wall thickness of 1 to 3 mm.

43. The process according to embodiment 41 or 42, wherein the coated rings have an external diameter of 4 to 10 mm, a length of 2 to 10 mm and a wall thickness of 1 to 4 mm.

44. The process according to any of embodiments 1 to 43, wherein starting reaction gas mixture 1 is formed from feed streams comprising recycle gaseous stream P;

a propene source;

a source of molecular oxygen;

optionally a stream of steam; and

optionally one or more streams of one or more than one hydrocarbon selected from the group consisting of methane, natural gas, ethane, propane, n-butane, isobutane and ethene.

45. The process according to any of embodiments 1 to 44, wherein starting reaction gas mixture 1 is formed from feed streams comprising oxygen of a purity of at least 90% by vol. $O_2$ and not more than 10% by vol. $N_2$ as source of molecular oxygen.

46. The process according to any of embodiments 1 to 44, wherein starting reaction gas mixture 1 is formed from feed streams comprising oxygen of a purity of at least 95% by vol. $O_2$ and not more than 5% by vol. $N_2$ as source of molecular oxygen.

47. The process according to any of embodiments 1 to 44, wherein starting reaction gas mixture 1 is formed from feed streams comprising oxygen of a purity of at least 98% by vol. $O_2$ and not more than 2% by vol. $N_2$ as source of molecular oxygen.

48. The process according to any of embodiments 1 to 44, wherein starting reaction gas mixture 1 is formed from feed streams comprising oxygen of a purity of at least 99% by vol. $O_2$ and not more than 1% by vol. $N_2$ as source of molecular oxygen.

49. The process according to any of embodiments 1 to 44, wherein starting reaction gas mixture 1 is formed from feed streams comprising oxygen of a purity of from 99.4% by vol. to 99.9% by vol. $O_2$ and of from 0.1% by vol. to 0.6% by vol. $N_2$ as source of molecular oxygen.

50. The process according to any of embodiments 1 to 44, wherein starting reaction gas mixture 1 is formed from feed streams comprising oxygen of a purity of from 99.5% by vol. to 99.8% by vol. $O_2$ and of from 0.2% by vol. to 0.5% by vol. $N_2$ as source of molecular oxygen.

51. The process according to any of embodiments 1 to 50, wherein as secondary gas oxygen of a purity of at least 90% by vol. $O_2$ and not more than 10% by vol. $N_2$ is added to product gas mixture 1 leaving the first reaction stage.

52. The process according to any of embodiments 1 to 50, wherein as secondary gas oxygen of a purity of at least 95% by vol. $O_2$ and of not more than 5% by vol. $N_2$ is added to product gas mixture 1 leaving the first reaction stage.

53. The process according to any of embodiments 1 to 50, wherein as secondary gas oxygen of a purity of at least 98% by vol. $O_2$ and of not more than 2% by vol. $N_2$ is added to product gas mixture 1 leaving the first reaction stage.

54. The process according to any of embodiments 1 to 50, wherein as secondary gas oxygen of a purity of at least 99% by vol. $O_2$ and of not more than 1% by vol. $N_2$ is added to product gas mixture 1 leaving the first reaction stage.

55. The process according to any of embodiments 1 to 50, wherein as secondary gas oxygen of a purity of from 99.4% by vol. to 99.9% by vol. $O_2$ and of from 0.1% by vol. to 0.6% by vol. $N_2$ is added to product gas mixture 1 leaving the first reaction stage.

56. The process according to any of embodiments 1 to 50, wherein as secondary gas oxygen of a purity of from 99.5% by vol. to 99.8% by vol. $O_2$ and of from 0.2% by vol. to 0.5% by vol. $N_2$ is added to product gas mixture 1 leaving the first reaction stage.

57. The process according to any of embodiments 1 to 56, wherein starting reaction gas mixture 1 is formed from feed streams comprising propene feedstock containing ≥99% by vol. propene and ≤1% by vol. propane.

58. The process according to any of embodiments 1 to 56, wherein starting reaction gas mixture 1 is formed from feed streams comprising propene feedstock containing ≥90% by vol. propene and ≤10% by vol. but ≥2% by vol. propane.

59. The process according to any of embodiments 1 to 56, wherein starting reaction gas mixture 1 is formed from feed streams comprising propene feedstock containing ≥70% by vol. propene and ≤30% by vol. but ≥15% by vol. propane.

60. The process according to any of embodiments 1 to 59, wherein as secondary gas inert gas is added to the product gas leaving the first reaction stage.

61. The process according to any of embodiments 1 to 60, wherein starting reaction gas mixture 1 is formed from feed streams comprising one or more streams of at least one hydrocarbon selected from the group consisting of methane, natural gas, ethane, propane, n-butane, isobutane and ethene.

62. The process according to any of embodiments 1 to 61, wherein the mass flow of the recycle gaseous stream P is at least 70% but not more than 99.5% of the mass flow M of residual gas mixture R continuously conducted out of the separating zone and the mass flow of the off-gas stream O is not more than 30% but at least 0.5% of the total mass flow M of residual gas mixture R continuously conducted out of the separating zone.

63. The process according to any of embodiments 1 to 61, wherein the mass flow of the recycle gaseous stream P is at least 80% but not more than 99.0% of the mass flow M of residual gas mixture R continuously conducted out of the separating zone and the mass flow of the off-gas stream O is not more than 20% but at least 1.0% of the total mass flow M of residual gas mixture R continuously conducted out of the separating zone.

64. The process according to any of embodiments 1 to 61, wherein the mass flow of the recycle gaseous stream P is at least 95% but not more than 98.0% of the mass flow M of residual gas mixture R continuously conducted out of the separating zone and the mass flow of the off-gas stream O is not more than 5% but at least 2.0% of the total mass flow M of residual gas mixture R continuously conducted out of the separating zone.

65. The process according to any of embodiments 1 to 61, wherein the process comprises under stationary operating conditions A) as an obligatory measure continuously passing in a first reaction stage a stream of a starting reaction gas mixture 1 consisting of from 2 to 15% by volume of propene, from 2.4 to 37.5% by volume of molecular oxygen, from 0.5 to 10% by volume of water, from 0 to 10% (preferably 0 to 5%) by volume of molecular nitrogen, from 15 to 25% by volume of carbon monoxide, from 20 to 55% by volume of carbon dioxide, from 10 to 30% by volume of at least one hydrocarbon selected from the group consisting of methane, ethane, propane, n-butane, isobutane and ethene (preferably essentially only propane), and from >0 to 5% by volume of other compounds including but not limited to acrolein and/or acrylic acid,
and containing
the molecular oxygen and the propene in a molar $O_2$:propene ratio ranging from 1.2 to 2.5,
the carbon dioxide and the carbon monoxide in a molar $CO_2$:CO ratio ranging from 1 to 4,
and the molecular oxygen and the molecular nitrogen in a molar $O_2$:$N_2$ ratio of at least 0.5,
at a reaction temperature of from 250° C. to 500° C. and a working pressure of from 1 bar to 6 bar through a first fixed catalyst bed comprising shaped catalyst bodies whose active mass is at least one multimetal oxide containing molybdenum (Mo), bismuth (Bi) and iron (Fe) in such a way, that the propene conversion on single pass is from 80 mol % to 99 mol % and the accompanying selectivity $S^4$ of the formation of the target product acrolein is from 70 mol % to 99 mol % to obtain a stream of a the target product acrolein containing product gas mixture 1 leaving the first reaction stage,
and,
B) in case of acrylic acid being the target product, optionally reducing the temperature of the product gas mixture leaving the first reaction stage by direct, indirect or direct and indirect cooling,
optionally adding secondary gas to said product gas mixture in the form of molecular oxygen, or inert gas, or molecular oxygen and inert gas, and
subsequently continuously passing in a second reaction stage a stream of the thus resulting starting reaction gas mixture 2 consisting of
from 2 to 15% by volume of acrolein,
from 1 to 45% by volume of molecular oxygen,
from 2 to 20% by volume of water,
from 0 to 10% (preferably 0 to 5%) by volume of molecular nitrogen,
from 15 to 25% by volume of carbon monoxide,
from 20 to 55% by volume of carbon dioxide,
from 10 to 30% by volume of at least one hydrocarbon selected from the group consisting of methane, ethane, propane, n-butane, isobutane and ethene (preferably essentially only propane), and
from >0 to 5% by volume of other compounds including but not limited to propene and/or acrylic acid,
and containing
the molecular oxygen and the acrolein in a molar $O_2$:acrolein ratio ranging from 0.5 to 3,
the carbon dioxide and the carbon monoxide in a molar $CO_2$:CO ratio ranging from 1 to 4, and
the molecular oxygen and the molecular nitrogen in a molar $O_2$:$N_2$ ratio of at least 0.25,
at a reaction temperature of from 200° C. to 450° C. and a working pressure of from 1 bar to 6 bar through a second fixed catalyst bed comprising shaped catalyst bodies whose active mass is at least one multimetal oxide containing molybdenum (Mo) and vanadium (V) in such a way, that the acrolein conversion on single pass is from 95 mol % to 99.99 mol % and the accompanying selectivity $S^{AA}$ of the formation of the target product acrylic acid assessed over both reaction stages and based on converted propene is from 80 mol % to 99.9 mol % to obtain a stream of a the target product acrylic acid containing product gas mixture 2 leaving the second reaction stage, and
C) either continuously transporting the stream of the target product acrolein containing product gas mixture 1 or the stream of the target product acrylic acid containing product gas mixture 2 into a separating zone and separating in the separating zone the respective target product from the respective product gas mixture through transferring at least 95 mol % of the respective target product contained in the respective product gas mixture from the gaseous phase into the liquid phase and continuously conducting out of the separating zone a total mass flow M of a residual gas mixture R which contains, of the total molar amount of those compounds contained in the product gas mixture continuously transported into the separating zone, which have as pure compounds at a working pressure of 1 bar a boiling point below 250 K, at least 95 mol % and
D) recycling as gaseous stream P having the same composition as the residual gas mixture R a partial stream of the total mass flow M of residual gas mixture R continuously conducted out of the separating zone into the first reaction stage 1 as feed stream for preparing the stream of the starting reaction gas mixture 1 which shall contain the gaseous stream P, and discharging of the production process as off-gas stream O, having the same composition as the residual gas mixture R, the difference between the total mass flow M of residual gas mixture R continuously conducted out of the separating zone and the mass flow of recycle gaseous stream P,
wherein
a) the mass flow of the recycle gaseous stream P is at least 90% but not more than 99% of the total mass flow M of residual gas mixture R continuously conducted out of the separating zone,
b) the mass flow of the off-gas stream O is not more than 10% but at least 1% of the total mass flow M of residual gas mixture R continuously conducted out of the separating zone, and
c) the composition C of the residual gas mixture R is from 0.05 to 0.5% by volume of propene,
from 1 to 4% by volume of molecular oxygen,
from 0.5 to 10% by volume of water,
from 0 to 10% (preferably 0 to 5%) by volume of molecular nitrogen,
from 15 to 30% by volume of carbon monoxide,
from 30 to 60% by volume of carbon dioxide,
from 10 to 50% by volume of at least one hydrocarbon selected from the group consisting of methane, ethane, propane, n-butane, isobutane and ethene (preferably essentially only propane), and
from 0.01 to 5% by volume of other compounds including but not limited to acrolein and/or acrylic acid.
66. The process according to embodiment 65, wherein starting reaction gas mixture 1 is formed from feed streams consisting of a propene feedstock stream containing ≥90% by vol. propene and ≤10% by vol. but ≥2% by vol. propane, a stream of molecular oxygen of the purity ≥99.0% by vol. and ≤99.9% by vol. $O_2$ and ≤1% by vol. and ≥0.1% by vol. $N_2$, and recycle gaseous stream P.
67. The process according to any of embodiments 1 to 61, wherein the process comprises under stationary operating conditions

A) as an obligatory measure continuously passing in a
first reaction stage a stream of a starting reaction gas
mixture 1 consisting of
from 2 to 15% by volume of propene,
from 2.4 to 37.5% by volume of molecular oxygen,
from 0.5 to 10% by volume of water,
from 0 to 10% (preferably 0 to 5%) by volume of
molecular nitrogen,
from 1.2 to 15% by volume of carbon monoxide,
from 3 to 30% by volume of carbon dioxide,
from 40 to 80% by volume of at least one hydrocar-
bon selected from the group consisting of meth-
ane, ethane, propane, n-butane, isobutane and
ethene (preferably at least 80 mol % of the total
molar amount of these hydrocarbons is methane),
and
from >0 to 5% by volume of other compounds
including but not limited to acrolein and/or acrylic
acid,
and containing
the molecular oxygen and the propene in a molar
$O_2$:propene ratio ranging from 1.2 to 2.5,
the carbon dioxide and the carbon monoxide in a
molar $CO_2$:CO ratio ranging from 1 to 4,
the molecular oxygen and the molecular nitrogen
in a molar $O_2$:$N_2$ ratio of at least 0.5, and
the carbon monoxide and the total molar amount
(quantity) of hydrocarbons in a molar CO:total
hydrocarbons ratio ranging from >0 to 0.3,
at a reaction temperature of from 250° C. to 500° C.
and a working pressure of from 1 bar to 6 bar
through a first fixed catalyst bed comprising
shaped catalyst bodies whose active mass is at
least one multimetal oxide containing molybde-
num (Mo), bismuth (Bi) and iron (Fe) in such a
way, that the propene conversion on single pass is
from 80 mol % to 99 mol % and the accompanying
selectivity $S^A$ of the formation of the target prod-
uct acrolein is from 70 mol % to 99 mol % to
obtain a stream of a the target product acrolein
containing product gas mixture 1 leaving the first
reaction stage,
and,
B) in case of acrylic acid being the target product,
optionally reducing the temperature of the product
gas mixture leaving the first reaction stage by
direct, indirect or direct and indirect cooling,
optionally adding secondary gas to said product gas
mixture in the form of molecular oxygen, or inert
gas, or molecular oxygen and inert gas, and
subsequently continuously passing in a second reac-
tion stage a stream of the thus resulting starting
reaction gas mixture 2 consisting of
from 2 to 15% by volume of acrolein,
from 1 to 45% by volume of molecular oxygen,
from 2 to 20% by volume of water,
from 0 to 10% (preferably 0 to 5%) by volume of
molecular nitrogen,
from 1.2 to 15% by volume of carbon monoxide,
from 3 to 30% by volume of carbon dioxide,
from 40 to 80% by volume of at least one hydrocar-
bon selected from the group consisting of meth-
ane, ethane, propane, n-butane, isobutane and
ethene (preferably at least 80 mol % of the total
molar amount of these hydrocarbons is methane),
and

54 from >0 to 5% by volume of other compounds
including but not limited to propene and/or acrylic
acid,
and containing
the molecular oxygen and the acrolein in a molar
$O_2$:acrolein ratio ranging from 0.5 to 3,
the carbon dioxide and the carbon monoxide in a
molar $CO_2$:CO ratio ranging from 1 to 4,
the molecular oxygen and the molecular nitrogen
in a molar $O_2$:$N_2$ ratio of at least 0.25, and
the carbon monoxide and the total molar amount
(quantity) of hydrocarbons (including acrolein)
in a molar CO:total hydrocarbons ratio ranging
from >0 to 0.3,
at a reaction temperature of from 200° C. to 450° C.
and a working pressure of from 1 bar to 6 bar
through a second fixed catalyst bed comprising
shaped catalyst bodies whose active mass is at
least one multimetal oxide containing molybde-
num (Mo) and vanadium (V) in such a way, that
the acrolein conversion on single pass is from 95
mol % to 99.99 mol % and the accompanying
selectivity $S^{AA}$ of the formation of the target prod-
uct acrylic acid assessed over both reaction stages
and based on converted propene is from 80 mol %
to 99.9 mol % to obtain a stream of a the target
product acrylic acid containing product gas mix-
ture 2 leaving the second reaction stage, and
C) either continuously transporting the stream of the
target product acrolein containing product gas mix-
ture 1 or the stream of the target product acrylic acid
containing product gas mixture 2 into a separating
zone and separating in the separating zone the
respective target product from the respective product
gas mixture through transferring at least 95 mol % of
the respective target product contained in the respec-
tive product gas mixture from the gaseous phase into
the liquid phase and continuously conducting out of
the separating zone a total mass flow M of a residual
gas mixture R which contains, of the total molar
amount of those compounds contained in the product
gas mixture continuously transported into the sepa-
rating zone, which have as pure compounds at a
working pressure of 1 bar a boiling point below 250
K, at least 95 mol %
and
D) recycling as gaseous stream P having the same
composition as the residual gas mixture R a partial
stream of the total mass flow M of residual gas
mixture R continuously conducted out of the sepa-
rating zone into the first reaction stage 1 as feed
stream for preparing the stream of the starting reac-
tion gas mixture 1 which shall contain the gaseous
stream P, and discharging of the production process
as off-gas stream O, having the same composition as
the residual gas mixture R, the difference between
the total mass flow M of residual gas mixture R
continuously conducted out of the separating zone
and the mass flow of recycle gaseous stream P,
wherein
a) the mass flow of the recycle gaseous stream P is
at least 75% but not more than 98% of the total
mass flow M of residual gas mixture R continu-
ously conducted out of the separating zone,
b) the mass flow of the off-gas stream O is not more
than 25% but at least 2% of the total mass flow M of residual gas mixture R continuously conducted out of the separating zone, and c) the composition C of the residual gas mixture R is from 0.05 to 0.8% by volume of propene, from 1 to 4% by volume of molecular oxygen, from 0.5 to 10% by volume of water, from 0 to 10% (preferably 0 to 5%) by volume of molecular nitrogen, from 1.2 to 15% by volume of carbon monoxide, from 3 to 30% by volume of carbon dioxide, from 45 to 90% by volume of at least one hydrocarbon selected from the group consisting of methane, ethane, propane, n-butane, isobutane and ethene (preferably at least 80 mol % of the total molar amount of these hydrocarbons is methane), and from 0.01 to 5% by volume of other compounds including but not limited to acrolein and/or acrylic acid.

68. The process according to embodiment 67, wherein starting reaction gas mixture 1 is formed from feed streams consisting of a propene feedstock stream of polymer grade (propene feedstock containing ≥99% by vol. propene and ≤1% by vol. propane) or chemical grade propene (propene feedstock containing ≥90% by vol. propene and ≤10% by vol. but ≥2% by vol. propane), a stream of molecular oxygen of the purity ≥99.0% by vol. and ≤99.9% by vol. $O_2$ and ≤1% by vol. and ≥0.1% by vol. $N_2$, recycle gaseous stream P and an additional stream of at least one hydrocarbon selected from the group consisting of methane, natural gas, ethene, propane, n-butane, isobutane and ethene.

69. The process according to embodiment 68, wherein at least 80 mol % of the total molar amount (quantity) of hydrocarbons in the additional stream of at least one hydrocarbon is methane or natural gas.

70. The process according to embodiment 68, wherein at least 90 mol % of the total molar amount (quantity) of hydrocarbons in the additional stream of at least one hydrocarbon is methane or natural gas.

71. The process according to embodiment 68, wherein at least 95 mol % of the total molar amount (quantity) of hydrocarbons in the additional stream of at least one hydrocarbon is methane or natural gas.

72. The process according to embodiment 68, wherein 100 mol % of the total molar amount (quantity) of hydrocarbons in the additional stream of at least one hydrocarbon is methane or natural gas.

73. The process according to any of embodiments 1 to 72, wherein starting reaction gas mixture 1 and starting reaction gas mixture 2 are non-explosive.

74. The process according to any of embodiments 1 to 73, wherein the ratio $Q=(n_{CO})/(n_{CO}+n_{hydrocarbon})$ in the starting reaction gas mixture 1 ranges from >0 to 0.8.

75. The process according to any of embodiments 1 to 73, wherein the ratio $Q=(n_{CO})/(n_{CO}+n_{hydrocarbon})$ in the starting reaction gas mixture 1 ranges from 0.005 to 0.7.

76. The process according to any of embodiments 1 to 73, wherein the ratio $Q=(n_{CO})/(n_{CO}+n_{hydrocarbon})$ in the starting reaction gas mixture 1 ranges from 0.005 to 0.6.

77. The process according to any of embodiments 1 to 76, wherein the ratio $Q=(n_{CO})/(n_{CO}+n_{hydrocarbon})$ in the starting reaction gas mixture 2 ranges from >0 to 0.8.

78. The process according to any of embodiments 1 to 76, wherein the ratio $Q=(n_{CO})/(n_{CO}+n_{hydrocarbon})$ in the starting reaction gas mixture 2 ranges from 0.005 to 0.7.

79. The process according to any of embodiments 1 to 76, wherein the ratio $Q=(n_{CO})/(n_{CO}+n_{hydrocarbon})$ in the starting reaction gas mixture 2 ranges 0.005 to 0.6.

80. The process according to any of embodiments 1 to 79, wherein in the separating zone at least 96 mol % of the respective target product contained in the respective product gas mixture transported into the separating zone are transferred into the liquid phase.

81. The process according to any of embodiments 1 to 79, wherein in the separating zone at least 97 mol % of the respective target product contained in the respective product gas mixture transported into the separating zone are transferred into the liquid phase.

82. The process according to any of embodiments 1 to 79, wherein in the separating zone at least 98 mol % of the respective target product contained in the respective product gas mixture transported into the separating zone are transferred into the liquid phase.

83. The process according to any of embodiments 1 to 79, wherein in the separating zone at least 99 mol % of the respective target product contained in the respective product gas mixture transported into the separating zone are transferred into the liquid phase.

84. The process according to any of embodiments 1 to 83, wherein in the separating zone at least 99.5 mol % but not more than 99.8 mol % of the respective target product contained in the respective product gas mixture transported into the separating zone are transferred into the liquid phase.

85. The process according to any of embodiments 1 to 84, wherein the total mass flow M of the residual gas mixture R continuously conducted out of the separating zone contains, of the total molar amount of those compounds contained in the product gas mixture continuously transported into the separating zone, which have as pure compounds at a working pressure of 1 bar a boiling point below 250 K, at least 96 mol %.

86. The process according to any of embodiments 1 to 84, wherein the total mass flow M of residual gas mixture R continuously conducted out of the separating zone contains, of the total molar amount of those compounds contained in the product gas mixture continuously transported into the separating zone, which have as pure compounds at a working pressure of 1 bar a boiling point below 250 K, at least 97 mol %.

87. The process according to any of embodiments 1 to 84, wherein the total mass flow M of residual gas mixture R continuously conducted out of the separating zone contains, of the total molar amount of those compounds contained in the product gas mixture continuously transported into the separating zone, which have as pure compounds at a working pressure of 1 bar a boiling point below 250 K, at least 98 mol %.

88. The process according to any of embodiments 1 to 87, wherein the total mass flow M of residual gas mixture R continuously conducted out of the separating zone, contains, of the total molar amount of those compounds contained in the product gas mixture continuously transported into the separating zone, which have as pure compounds at a working pressure of 1 bar a boiling point below 250 K, at least 99 mol %, or at least 99.5 mol % but less than 100 mol %.

89. The process according to any of embodiments 1 to 88, wherein the transferring of the respective target product from the gaseous phase into the liquid phase comprises the absorption of the respective target product into a liquid absorbent and/or the condensation (preferably the fractional condensation) of the respective target product from the gaseous phase in at least one separating column containing separating internals in which the respective product gas mixture is conducted ascending from the bottom upward.

90. The process according to any of embodiments 1 to 89, wherein the liquid phase containing the respective target product within the separating zone is worked up including a separation of high boilers from the target product and to yield the target product in its desired purity and said high boilers and the purified target product are continuously conducted out of the separating zone.

91. The production process according to any of embodiments 1 to 90, characterized in, that it is operated combined with another process which comprises the conversion of the off-gas stream O discharged of the production process and fed to said other process to a synthesis gas and/or the mixing of said off-gas stream O into another synthesis gas produced in said other process from any feedstock other than the off-gas O to yield a thus amended other synthesis gas.

92. The production process according to embodiment 91, wherein the conversion of the off-gas stream O comprises at least one of the following reactions:

heterogeneously catalyzed steam reforming in the gas phase of hydrocarbon contained in the off-gas stream O;

heterogeneously catalyzed hydrogenation in the gas phase of $CO_2$ contained in the off-gas stream O;

heterogeneously catalyzed dry reformation in the gas phase of hydrocarbon with $CO_2$ being both contained in the off-gas stream O; and partial gas phase combustion of hydrocarbon and/or compounds being composed of C, H and O and being contained in the off-gas stream O.

93. The production process according to embodiment 91 or 92, wherein the resulting synthesis gas and/or amended other synthesis gas subsequently is converted in a synthesis process to produce any chemical compound containing C and H and optionally O.

EXAMPLES AND COMPARATIVE EXAMPLE

The production plant to be used for following Examples 1 to 4 and for the Comparison Example is always the same. It comprises a partial oxidation section and a separating zone. The design of the separating zone including its equipment corresponds qualitatively to that of Example 1 of WO 2008/090190 and deviates only in its dimensioning. The partial oxidation section essentially is an oxidation reactor system comprising two fixed-bed two-zone multitube (tube bundle) reactors in series including an after cooler which is connected downstream of the first stage reactor for indirect cooling of product gas mixture 1 leaving the first stage multitube reactor. The design of the reactor system including the salt melt serving as heat exchange medium corresponds qualitatively to that described in sections [0187] to [0226] of U.S. Pat. No. 0,249,196. Between the outlet "after cooler" and the inlet "second stage reactor" is a means for feeding compressed secondary molecular oxygen containing gas. Elements which in Examples 2 to 4 and the Comparison Example do not deviate from the corresponding elements described in Example 1 are no longer repeated in Examples 2 to 4 and the Comparison Example. The data presented in the illustrative Examples/Comparison Example for the separating zones are derived from arithmetic simulation and not actual experiments. The data presented for the partial oxidation section are derived from results obtained in comparable single tube experiments applying corresponding catalyst charges and similar/equivalent starting reaction gas mixtures and reaction conditions.

Example 1

A Steady State is Described (small amounts of $O_2$ dissolved in the liquid material flows are not included (addressed) in the following)

The charged contact tubes within the two-zone tube bundle reactor for the first reaction stage (propene→acrolein) are represented by the following reaction tube:

A reaction tube (V2A steel; external diameter: 30 mm, wall thickness: 2 mm, internal diameter: 26 mm, length: 350 cm) is charged from top to bottom as follows.

Section 1: length 50 cm steatite (C220 steatite from CeramTec GmbH, D-73207 Plochingen) rings of geometry 7 mm×3 mm×4 mm (external diameter× length×internal diameter) as a preliminary bed.

Section 2: length 115 cm catalyst charge of a homogeneous mixture of 35% by weight of steatite (C220 steatite from CeramTec GmbH, D-73207 Plochingen) rings of geometry 5 mm×5 mm×2 mm (external diameter×length×internal diameter) and 65% by weight unsupported catalyst from section 3.

Section 3: length 185 cm catalyst charge of annular unsupported catalyst (5 mm×5 mm×2 mm=external diameter×length×internal diameter) which, except its geometry, has been produced as the catalyst described in example 3 of U.S. Pat. No. 6,881,702 (stoichiometry: $Mo_{12}Co_7Fe_{2.94}Bi_{0.6}Si_{1.59}K_{0.08}O_x$). The weight and lateral compressive strength (determined as defined in WO 2005/030393 and in WO 2007/017431) of its not yet calcined precursor ring was 189±4 mg and 23±3 N respectively.

The first 175 cm from top to bottom are thermostatted by means of a salt bath A having the temperature $T^A$ pumped in countercurrent. The second 175 cm are thermostatted by means of a salt bath B having the temperature $T^B$ pumped in countercurrent.

The charged contact tubes within the two-zone tube bundle reactor for the second reaction stage (acrolein→acrylic acid) are represented by the following reaction tube:

A reaction tube (V2A steel; external diameter: 30 mm, wall thickness: 2 mm, internal diameter: 26 mm, length: 350 cm) is charged from top to bottom as follows.

Section 1: length 20 cm steatite (C220 steatite from CeramTec GmbH, D-73207 Plochingen) rings of geometry 7 mm×3 mm×4 mm (external diameter× length×internal diameter) as a preliminary bed.

Section 2: length 140 cm catalyst charge of annular coated catalyst (7 mm×3 mm×4 mm=external diameter× length×internal diameter) which has been produced as the catalyst in example C8 of US-A 2015/0080605 with an oxidic eggshell content of 15% by weight and the stoichiometry $Mo_{12}V_3W_{1.2}O_x$ of its active mass.

Section 3: length 190 cm catalyst charge of annular coated catalyst (7 mm×3 mm×4 mm=external diameter× length×internal diameter) which has been produced as the catalyst in example C3 of US-A 2015/0080605 with an oxidic eggshell content of 20% by weight and the stoichiometry $Mo_{12}V_3W_{1.2}O_x$ of its active mass.

The first 175 cm from top to bottom are thermostatted by means of a salt bath C having the temperature $T^C$ pumped in countercurrent. The second 175 cm are thermostatted by means of a salt bath D having the temperature $T^D$ pumped in countercurrent.

Starting reaction gas mixture 1 is a mixture of the following feed gas streams:

15760 kg/h molecular oxygen (purity: 99.9999% by wt. of $O_2$);

16000 kg/h chemical grade propene (94.77% by wt. propene and 5.23% by wt. propane); and 211617 kg/h recycled gaseous stream P.

The temperature of starting reaction gas mixture 1 is 200° C. and its pressure (input pressure) is 2.434 bar. The composition of starting reaction gas mixture 1 fed through the reaction tubes first stage tube bundle reactor is:

| | |
|---|---|
| 0.06% by vol. of | formaldehyde |
| 0.02% by vol. of | acrolein |
| 2.05% by vol. of | water |
| 0.03% by vol. of | acetic acid |
| 0.03% by vol. of | acrylic acid |
| 6.00% by vol. of | propene |
| 17.28% by vol. of | propane |
| 10.80% by vol. of | molecular oxygen |
| 43.63% by vol. of | carbon dioxide |
| 20.10% by vol. of | carbon monoxide |

Temperature $T^A$ is 327° C. Temperature $T^B$ is 335° C.

The temperature in the catalytically active part of the fixed catalyst bed in the reaction tube is in the range of 325° C. to 398° C. (the lower limit of the range shows the lowest temperature in the catalytically active part of the fixed catalyst bed and the upper limit of the range shows the highest temperature in the catalytically active part of the fixed catalyst bed).

The propene hourly space velocity on the fixed catalyst bed (Section 2+Section 3 in the reaction tube) is 164 (l (STP)/l·h).

The single pass propene conversion is 95.85 mol % and the accompanying selectivity $S^A$ of the formation of acrolein is 91.64 mol %.

The stream of 243377 kg/h of product gas mixture 1 leaving the first reaction stage with a temperature of 360° C. and a pressure of 1.834 bar has the following composition:

| | |
|---|---|
| 0.05% by vol. of | formaldehyde |
| 5.30% by vol. of | acrolein |
| 8.08% by vol. of | water |
| 0.13% by vol. of | acetic acid |
| 0.27% by vol. of | acrylic acid |
| 0.25% by vol. of | propene |
| 17.29% by vol. of | propane |
| 4.38% by vol. of | molecular oxygen |
| 43.98% by vol. of | carbon dioxide |
| 20.27% by vol. of | carbon monoxide |

The temperature of the product gas mixture leaving the first reaction stage (product gas mixture 1) is reduced by indirect cooling in the after cooler. The stream of thus cooled product gas mixture 1 (temperature=250° C.) is mixed with a stream of 3612.9 kg/h secondary molecular oxygen (purity: 99.9999% by wt. of $O_2$; temperature: 165.00° C.; pressure: 2.50 bar).

The composition of the 246990 kg/h of thus resulting starting reaction gas mixture 2 (temperature: 249.2° C.;

pressure: 1.809 bar) fed through the reaction tubes of the second stage tube bundle reactor is:

| | |
|---|---|
| 0.05% by vol. of | formaldehyde |
| 5.20% by vol. of | acrolein |
| 7.94% by vol. of | water |
| 0.13% by vol. of | acetic acid |
| 0.27% by vol. of | acrylic acid |
| 0.24% by vol. of | propene |
| 16.98% by vol. of | propane |
| 6.07% by vol. of | molecular oxygen |
| 43.21% by vol. of | carbon dioxide |
| 19.91% by vol. of | carbon monoxide |

Temperature $T^C$ is 267° C. Temperature $T^D$ is 272° C.

The temperature in the catalytically active part of the fixed catalyst bed in the reaction tube is in the range of 265° C. to 302° C. (the lower limit of the range shows the lowest temperature in the catalytically active part of the fixed catalyst bed and the upper limit of the range shows the highest temperature in the catalytically active part of the fixed catalyst bed).

The acrolein hourly space velocity on the fixed catalyst bed (Section 2 and Section 3 in the reaction tube) is 132 (l (STP)/l·h).

The single pass acrolein conversion is 99.53 mol % and the accompanying selectivity $S^{AA}$ of the formation of acrylic acid and assessed over both reaction stages and based on converted propene is 89.77 mol %.

The product gas mixture (246990 kg/h, T=250° C., P=1.509 bar) leaving the second stage reactor (product gas mixture 2) at its entrance into the separating zone is cooled in a spray cooler (quench 1) operated in cocurrent by direct cooling to a temperature of 120° C.

The composition of product gas mixture 2 is:

| | |
|---|---|
| 0.25% by vol. of | formaldehyde |
| 0.03% by vol. of | acrolein |
| 8.51% by vol. of | water |
| 0.02% by vol. of | formic acid |
| 0.15% by vol. of | acetic acid |
| 5.22% by vol. of | acrylic acid |
| 0.03% by vol. of | maleic anhydride |
| 0.25% by vol. of | propene |
| 17.36% by vol. of | propane |
| 3.00% by vol. of | molecular oxygen |
| 44.63% by vol. of | carbon dioxide |
| 20.55% by vol. of | carbon monoxide |

The liquid to be used for the direct cooling of the product gas mixture 2 (quench liquid 1) is a portion (529660 kg/h, T=116.5° C.) of bottoms liquid which is withdrawn in a total amount of 533070 kg/h (T=116.5° C.) from the bottom of the condensation column described below. Contents of this bottom liquid are:

| | |
|---|---|
| 0.71% by wt. of | water |
| 0.01% by wt. of | formic acid |
| 0.27% by wt. of | acetic acid |
| 47.55% by wt. of | acrylic acid |
| 0.04% by wt. of | propionic acid |
| 0.19% by wt. of | furfurals |
| 0.15% by wt. of | benzaldehyde |
| 5.67% by wt. of | maleic anhydride |
| 35.13% by wt. of | diacrylic acid |
| 0.77% by wt. of | MEHQ |
| 0.81% by wt. of | benzoic acid |
| 0.31% by wt. of | phthalic anhydride |
| 0.32% by wt. of | phenothiazine |

-continued

| | |
|---|---|
| 8.00% by wt. of | polyacrylic acid |
| 0.01% by wt. of | methylene glycol |
| 0.06% by wt. of | propane |

The mixture of product gas mixture cooled to 120° C. and unevaporated quench liquid 1 having same temperature which results in the direct cooling is conducted as such into the bottom of the condensation column. The pressure in the bottom space and in the quench 1 is 1.479 bar. The other portion (3410 kg/h) of bottoms liquid withdrawn from the bottom of the condensation column is supplied to the second stripping column and fed into its middle section. The second stripping column comprises dual-flow trays as separating internals. Just like the condensation column, the second stripping column is insulated thermally from the environment.

The energy required for cracking diacrylic acid and polyacrylic acid (both Michael adducts) contained in the bottoms liquid into acrylic acid is supplied into the second stripping column by means of an external forced-circulation three-flow tube bundle flash evaporator, which is fed with bottoms liquid of the second stripping column. The heat carrier conducted through the space surrounding the heat exchanger tubes is pressurized steam. As it flows through the heat exchanger tubes, the bottoms liquid is heated, and its major amount thereafter recycled into the bottom of the second stripping column. A small amount of the total amount of bottoms liquid conducted through the heat exchanger is branched off, degassed and, diluted with methanol, sent to residue incineration.

In addition, the first laden gas conducted out of the first stripping column at the top thereof is fed into the bottom of the second stripping column. Second laden (especially with acrylic acid and water) gas is conducted out of the top of the second stripping column in an amount of 18851 kg/h (temperature=65° C., pressure=1.40 bar) and fed into quench 1 and/or the bottom of the condensation column. Contents of the second laden gas are:

| | |
|---|---|
| 0.05% by vol. of | formaldehyde |
| 0.02% by vol. of | acrolein |
| 6.87% by vol. of | water |
| 0.51% by vol. of | acetic acid |
| 6.98% by vol. of | acrylic acid |
| 0.25% by vol. of | propene |
| 17.32% by vol. of | propane |
| 2.99% by vol. of | molecular oxygen |
| 44.51% by vol. of | carbon dioxide |
| 20.50% by vol. of | carbon monoxide |

A centrifugal droplet separator which prevents droplets of the bottoms liquid from being entrained upward out of the bottom space is integrated into the bottom space of the condensation column.

The bottom space of the condensation column is concluded by a first collecting tray (chimney tray with uniformly distributed roofed chimneys).

The collecting tray has a double-wall configuration with 2° inward gradient and a central draw cup and draw nozzle. The free gas cross section is approximately 30%.

104368 kg/h of high boiler fraction are conducted from this first collecting tray into the bottom space disposed below the first collecting tray. The high boiler fraction has, at a temperature of 105.8° C. and pressure of approximately 1.479 bar, the following contents:

| | |
|---|---|
| 0.01% by wt. of | formaldehyde |
| 1.17% by wt. of | water |
| 0.01% by wt. of | formic acid |
| 0.45% by wt. of | acetic acid |
| 93.08% by wt. of | acrylic acid |
| 0.07% by wt. of | propionic acid |
| 0.29% by wt. of | furfurals |
| 0.17% by wt. of | benzaldehyde |
| 3.63% by wt. of | maleic anhydride |
| 0.95% by wt. of | diacrylic acid |
| 0.06% by wt. of | MEHQ |
| 0.02% by wt. of | benzoic acid |
| 0.01% by wt. of | phenothiazine |
| 0.08% by wt. of | propane |

The bottom temperature is 116.5° C. and the bottom pressure (at the liquid level) is 1.479 bar.

Above the first collecting tray is disposed a first sequence of equidistant dual-flow trays. The passage orifices consist of circular orifices of a uniform diameter, the punching burr pointing downward in the separating column. The arrangement of the centers of the passage circles follows strict triangular pitch. The top tray functions as a distributor tray. For this purpose, the column wall comprises, between second collecting tray and foresaid top tray, two inserted tubes with bores. Crude acrylic acid and mother liquor are recycled via the inserted tubes into the condensation column. The first series of dual-flow trays is concluded with a second collecting tray (chimney tray with uniformly distributed roofed chimneys; central draw cup with draw nozzle, free gas cross section about 30%) which is mounted above the last dual-flow tray.

From this second collecting tray, 266895 kg/h crude acrylic acid with a temperature of 103.6° C. are withdrawn continuously at 1.443 bar as the first side draw, which has the following contents:

| | |
|---|---|
| 0.01% by wt. of | formaldehyde |
| 1.24% by wt. of | water |
| 0.02% by wt. of | formic acid |
| 0.88% by wt. of | acetic acid |
| 96.98% by wt. of | acrylic acid |
| 0.09% by wt. of | propionic acid |
| 0.12% by wt. of | furfurals |
| 0.02% by wt. of | benzaldehyde |
| 0.18% by wt. of | maleic anhydride |
| 0.35% by wt. of | diacrylic acid |
| 0.02% by wt. of | MEHQ |
| 0.01% by wt. of | phenothiazine |
| 0.08% by wt. of | propane |

60745 kg/h of the crude acrylic acid withdrawn from the second collecting tray, together with mother liquor (68362 kg/h) which has been obtained in the crystallizative further purification of withdrawn acrylic acid and has been heated to 90° C. in the indirect heat exchange with drawn crude acrylic acid and steam as heat carrier are recycled into the condensation column via aforementioned inserted tubes immediately below the second collecting tray to the dual-flow tray which follows below the second collecting tray.

115000 kg/h of the crude acrylic acid withdrawn from the second collecting tray are with a temperature of 103.6° C. recycled directly above the second collecting tray through spray nozzles to keep this section wetted and prevent fouling.

91149 kg/h of the crude acrylic acid withdrawn from the second collecting tray are cooled to a temperature of 29° C. by multistage indirect heat exchange (inter alia, in a thermally integrated manner against aforementioned mother liquor to be recycled into the condensation column), and optionally intermediately buffered in a tank farm. About 1000 kg/h of demineralized water are than added to the cooled acrylic acid.

The resulting mixture is cooled and subsequently crystallized in cooling disk crystallizers and the resulting crystal suspension purified in hydraulic melt wash columns as described in WO 2008/090190 on pages 49 and 50. From the melt circuits which are stabilized by the addition of a solution of MEHQ in glacial acrylic acid, 22787 kg/h of the desired separated acrylic acid are withdrawn as glacial acrylic acid showing the following contents:

| | |
|---|---|
| 0.01% by wt. of | water |
| 0.19% by wt. of | acetic acid |
| 99.76% by wt. of | acrylic acid |
| 0.03% by wt. of | propionic acid |
| 0.01% by wt. of | MEHQ |

It is outstandingly suitable for preparing superabsorbents based on poly-sodium acrylate. In 904 kg/h of the aforementioned glacial acrylic acid 11 kg/h of PTZ (phenothiazine) are dissolved to prepare an inhibitor solution 1 at 25° C. The remaining flow of glacial acrylic acid continuously withdrawn from the melt circuits is fed continuously in the storage tank.

The mother liquor removed in the wash columns is initially conducted into a heatable collecting vessel and from there into a tank. From this tank it is (as already mentioned) heated to 90° C. with thermal integration and recycled in a mass flow of 68362 kg/h, together (as a mixed flow (96.4° C., 1.10 bar)) with 60745 kg/h of the crude acrylic acid withdrawn at the second collecting tray of the condensation column, to the condensation column at the upper part of the series of dual-flow trays below the second collecting tray.

The composition of the recycled mother liquor is as follows:

| | |
|---|---|
| 1.65% by wt. of | water |
| 0.02% by wt. of | formic acid |
| 1.13% by wt. of | acetic acid |
| 96.05% by wt. of | acrylic acid |
| 0.11% by wt. of | propionic acid |
| 0.15% by wt. of | furfurals |
| 0.03% by wt. of | benzaldehyde |
| 0.24% by wt. of | maleic anhydride |
| 0.47% by wt. of | diacrylic acid |
| 0.02% by wt. of | MEHQ |
| 0.02% by wt. of | benzoic acid |
| 0.01% by wt. of | phenothiazine |
| 0.10% by wt. of | propane |

Above the second collecting tray in the condensation column is disposed the first dual-flow tray of a second sequence of equidistant dual-flow trays. The passage orifices consist of circular orifices of a uniform diameter, the punching burr pointing downward in the separating column. The arrangement of the centers of the passage circles follows strict triangular pitch. Above the last of the dual-flow trays begins an equidistant arrangement of conventional, single-flow Thormann trays. The first of the Thormann trays from the bottom is one in which the liquid draining from the tray drains via downcomers configured as tubes. These tubes are sealed hydraulically from the gas space of the next dual-flow tray down. The weir height of the drain tubes decreases in flow direction of the crossflow tray. The hydraulic sealing has emptying orifices with impingement plates. The drain tubes are distributed uniformly in the last third of the tray cross section (opposite to the feed on the tray). The hydraulic sealing is effected into a cup with oblique overflow weir (45°). Otherwise, the Thormann trays are configured such that a mutually opposite flow direction of the liquid is obtained in successive channels in flow direction through the arrangement of the motive slots in the hood of the Thormann trays.

A third collecting tray (chimney tray with approximately uniformly distributed roofed chimneys) is disposed above the uppermost Thormann tray. 843612 kg/h of acid water with a temperature of 60.7° C. and a pressure of 1.229 bar are withdrawn as the second side withdraw from the third collecting tray.

The acid water has the following contents:

| | |
|---|---|
| 0.11% by wt. of | formaldehyde |
| 0.01% by wt. of | acrolein |
| 0.02% by wt. of | allyl formate |
| 79.90% by wt. of | water |
| 0.51% by wt. of | formic acid |
| 5.65% by wt. of | acetic acid |
| 7.52% by wt. of | acrylic acid |
| 6.28% by wt. of | methylene glycol |

34405 kg/h of the acid water withdrawn (60.7° C.) are recycled to the uppermost Thormann tray together with 35 kg/h of inhibitor solution 1 (25° C.) and 28 kg/h molten MEHQ (T=80° C.). 880 kg/h of inhibitor solution 1 are recycled (with a temperature of 25° C.) to the arrangement of the single-flow Thormann trays (approximately after two-thirds of the length of this Thormann separation section (counted from its bottom)).

458.80 m³/h of the acid water withdrawn are recycled at a temperature of 28.1° C. to the middle of an equidistant arrangement of valve trays which is described in more detail below (the cooling is effected by means of multistage indirect heat exchange).

325000 kg/h of the acid water withdrawn are recycled at a temperature of 23.2° C. to the uppermost of the aforementioned equidistant arrangement of valve trays (the cooling is effected together with the aforementioned amount of acid water by means of multistage indirect heat exchange; the last cooling stage from 28.1° C. to 23.2° C. is effected thermally and with heat integration (liquid chemical grade propene is used as the coolant and evaporates at the same time; the resulting gaseous propene is subsequently used for the configuration of the starting reaction gas mixture 1 for the first stage of the heterogeneously catalyzed gas-phase partial oxidation of propene). 9207 kg/h of the acid water withdrawn are fed to the extraction column for the purpose of the extraction still to be performed thereafter.

Above the third collecting tray in the condensation column is mounted a sequence of two-flow valve trays in equidistant arrangement. The heights of the overflow weirs of the upper valve trays are higher than those of the lower valve trays. The valves used are VV12 valves from Stahl, Viernheim, Germany. The pressure at the top of the condensation column is 1.17 bar. At the top of the condensation column 231380 kg/h of the residual gas mixture R leave the separating column with a temperature of 24° C. and the following contents:

| | |
|---|---|
| 0.06% by vol. of | formaldehyde |
| 0.03% by vol. of | acrolein |

| | |
|---|---|
| 2.39% by vol. of | water |
| 0.03% by vol. of | acetic acid |
| 0.04% by vol. of | acrylic acid |
| 0.28% by vol. of | propene |
| 19.72% by vol. of | propane |
| 3.41% by vol. of | molecular oxygen |
| 50.69% by vol. of | carbon dioxide |
| 23.35% by vol. of | carbon monoxide |

In an indirect heat exchanger, the gas mixture R is heated to 32° C. 3763 kg/h thereof are discharged of the production process as off-gas stream O.

227617 kg/h of foresaid gas mixture R are compressed to a pressure of 2.5 bar by means of a compressor, which raises its temperature to approximately 150° C. 16000 kg/h thereof are fed to the first stripping column within the separating zone for stripping the extract from the acid water extraction. The remaining 211617 kg/h of the compressed gas mixture are (as cycle gas) recycled as gaseous stream P into the first reaction stage 1 as feed stream for preparing the stream of starting reaction gas mixture 1. The total of the mass flows of off-gas stream O and of cycle gaseous stream P constitutes the total mass flow M of residual gas mixture R which is continuously conducted out of the separating zone. It contains, of the total molar amount of those compounds contained in the product gas mixture 2 continuously transported into the separating zone, which have as pure compounds at a working pressure of 1 bar a boiling point below 250 K, 99.99 mol %.

The mass flow of the recycle gaseous stream P is 98.37% of the total mass flow M of residual gas mixture R which is continuously conducted out of the separating zone.

The extraction column for the acid water extraction comprises, as separating internals, punched structured packings fitted so as to be flush at the edge and made of stainless steel sheets (material 1.4571) of the Montz-Pak B1-350 type, which are arranged one on top of another. The internal diameter of the extraction column over all packings is uniform. The extractant used is Palatinol® A (diethyl phthalate). The internal diameter of bottom and top vessel of the extraction column are widened (compared with the uniform internal diameter of the column along the packings) in order to improve the phase separation in the bottom and reduce the entrainment of extractant in the top of the column. In addition, a bed of random plastics (for example polyethylene or Teflon®) is introduced as a coalescence aid in the top of the column. The 9207 kg/h of acid water to be extracted (temperature=60.7° C.) are fed into the extraction column below the lowermost packing via tubular distributors having appropriate passage orifices. Above the uppermost packing of the extraction column, a mixture (temperature=50° C.) of fresh Palatinol® A and extractant (in a ratio of the respective mass flows of 1:240) which has been recycled from the first stripping column and has been stripped free therein beforehand is introduced in a mass flow essentially equal to the 9207 kg/h of acid water. The recycled extractant has the following contents:

| | |
|---|---|
| ≤0.5% by wt. of | acrylic acid |
| ≤0.03% by wt. of | acetic acid |
| ≤0.02% by wt. of | water |
| ≤0.001% by wt. of | formic acid |
| ≤0.0035% by wt. of | acrolein |
| ≤0.00005% by wt. of | propionic acid |
| ≤0.0001% by wt. of | furfurals |

| | |
|---|---|
| ≤0.001% by wt. of | allyl formate |
| ≤0.03% by wt. of | MEHQ |
| ≥99.5% by wt. of | Palatinol ® A |

The specific mass of the acid water (temperature=60.7° C.) is 1011.5 kg/m³. The extractant is likewise introduced via tubular distributors having appropriate passage orifices. The acid water forms the continuous phase and the extractant forms the phase dispersed in droplet form (droplet diameter in the range from 2 to 5 mm), which descends in the aqueous phase. At the top of the extraction column the raffinate is withdrawn. It is sent to incineration. The extract is withdrawn from the bottom of the extraction column. It contains the acrylic acid extracted from the acid water. The entirety of the extract is conducted to the top of the first stripping column. Beforehand the extract is heated to 95° C. by indirect heat exchange in a plate heat exchanger. The heat carrier is bottom liquids withdrawn at the first stripping column. The first stripping column comprises, as separating internals, from bottom to top, first an arrangement of equidistant dual-flow trays and then an arrangement of three times as much single-flow Thormann trays. Just like the extraction column, the first stripping column is insulated thermally from the environment. The hole diameter of the dual-flow trays is uniform (hole arrangement corresponding to strict triangular pitch). The Thormann trays are configured such, that a mutually opposite flow direction of the liquid is obtained in each case in channels successive in crossflow direction via the arrangement of the motive slots in the hoods of the Thormann trays. Above the last Thormann tray is also disposed a bed of Pall rings made of metal as a droplet trap.

Below the lowermost dual-flow tray the 16000 kg/h of the compressed residual gas mixture R (2.5 bar, 150° C.) are conducted into the first stripping column, where it ascends in countercurrent to the extract descending in the stripping column. At the top of the first stripping column first laden (especially with water and acrylic acid) gas is conducted out (16851 kg/h) and fed into the second stripping column. The composition of the first laden gas is:

| | |
|---|---|
| 0.05% by vol. of | formaldehyde |
| 0.03% by vol. of | allyl formate |
| 7.31% by vol. of | water |
| 0.46% by vol. of | acetic acid |
| 1.11% by vol. of | acrylic acid |
| 0.27% by vol. of | propene |
| 18.43% by vol. of | propane |
| 3.18% by vol. of | molecular oxygen |
| 47.35% by vol. of | carbon dioxide |
| 21.81% by vol. of | carbon monoxide |

Bottoms liquid is withdrawn continuously from the bottom of the first stripping column. One portion of the bottoms liquid withdrawn from the first stripping column are cooled by two-stage indirect heat exchange (the first stage in a plate heat exchanger with thermal integration against extract), and recycled as extractant to the top of the extraction column. The other portion of bottoms liquid withdrawn from the first stripping column are heated to about 160° C. in an external force-circulation tube bundle flash evaporator and recycled into the bottom of the first stripping column.

The overall propene conversion (based on multiple pass) in this Example 1 is 99.86 mol % (calculated from the difference between propene fed as content of the chemical grade propene via starting reaction gas mixture 1 into the production process and propene discharged of the production process as content of off-gas stream O).

The overall yield of acrylic acid produced in Example 1 is 87.2 mol % (calculated from acrylic acid continuously fed into the storage tank as content of glacial acrylic acid and propene fed into the production process as content of chemical grade propene via starting reaction gas mixture 1).

From the acrylic acid contained in product gas mixture 2 99.40 mol % are in the separating zone transferred into the liquid phase.

Production of Synthesis Gas from the Off-Gas of this Example 1

The off-gas discharged in this Example 1 from the process carried out for production of the target product acrylic acid directly can be used as raw material for production of synthesis gas. This production advantageously will be executed by a combined application of the following reactions a) to c), normally carried out at high temperature and high pressure:

a) heterogeneously catalyzed steam reforming of hydrocarbon contained in the off-gas;
  b) heterogeneously catalyzed hydrogenation of $CO_2$ contained in the off-gas (e.g. through hydrogen formed in reaction a)); and
  c) oxidation of organic by- and target product components still contained in the off-gas through residual molecular oxygen and/or water contained in the off-gas.

Preferably catalysts are used that are capable of catalyzing more than one (best all three) of aforementioned reactions a), b) and c). Such catalysts e.g. are disclosed in WO 2015/135968 (e.g. example 1 of said WO).

On a technical scale such production typically is carried out in externally heated tubular reformers (see e.g. Ullmann's Encyclopedia of Industrial Chemistry, Fifth Completely Revised Edition, Volume A12 (Formamides to Hexamethylendiamine), VCH Verlagsgesellschaft mbH, D-6940 Weinheim, page 192-194, section 2.2.3.).

On a laboratory scale the tubular reformer can be represented by a single externally heated reaction tube which can be designed, charged with catalyst and operated as follows.

Technologically advantageous the tubular laboratory steam reformer is an externally heated reaction tube made of INCOLOY® Alloy 800 H (VDM material no. 1.4876). Its total length is 100 mm, its inner diameter is 21 mm and its wall thickness is 2.87 mm. At the bottom of the tubular reactor a sieve ((square) mesh size no. 70 (nominal size opening=212 µm according to US ASTM standard sieve specification E-11)) is placed on a holder (sieve and holder are also prepared of INCOLOY® Alloy 800 H). On top of the sieve (located at the height of 10 mm from the bottom) a first fixed bed (length=10 mm) of inert steatite (C220 steatite from CeramTec GmbH, D-73207 Plochingen) particles with particle sizes in the range from 300 µm to 500 µm (measured through sieving; (square) mesh size no. 40 sieve (nominal size opening=425 µm according to US ASTM standard sieve specification E-11)) is placed. Prior to filling the still empty tubular volume with catalytically active particles, coming from the bottom of the tubular reactor, a single sheathed (sheath material: Inconel® Alloy 600 (VDM material no. 2.4816)) Pt—Pt/Rh thermocouple (diameter=3 mm) is (centered in the tube) introduced into the tube such that its single metering point is placed 30 mm above the top of the first fixed bed of inert steatite particles (to determine the actual temperature value in comparison to the target value for controlling the temperature in the catalyst bed). Subsequently a fixed bed (length=60 mm) of reformer catalyst particles (particle composition and preparation as in case of catalyst no. 1 in Table 1 of WO 2015/135968; particle sizes in the range from 300 µm to 500 µm (measured through sieving; (square) mesh size no. 40 sieve (nominal size opening=425 µm according to US ASTM standard sieve specification E-11)) is placed on top of the first fixed bed of inert steatite particles. A second fixed bed (length=20 mm) of the same inert steatite particles is placed on top of the fixed bed of the catalytically active reformer catalyst particles. The tubular reactor is heated from its outside over its full length of 100 mm by an electric jacket heater. Each gas stream flows from top to bottom through the reaction tube. The second fixed bed of inert steatite particles serves the purpose to bring the temperature of the flowing gas stream by the entrance into the fixed bed section which is catalytically active to the desired target temperature (examined by the thermocouple).

Before starting production of synthesis gas, the reformer catalyst particles will be activated for a period of 10 h at a temperature of 450° C. (always the temperature at the metering point of the thermocouple) by a stream of diluted hydrogen (5% by vol. $H_2$ and 95% by vol. $N_2$; each of both showing a purity of 4.0 (purity ≥99.99% by vol.; ≤50 vol. ppm $O_2$ and ≤30 vol. ppm $H_2O$). The molecular hydrogen hourly space velocity on the fixed catalyst bed (only the catalytically active section in the reaction tube and not including the two inert sections) is 190 (l (STP)/l·h). This corresponds to total gas flow of 1.33 l (STP)/min. The pressure at the tubular reactor inlet is 20 bar. The heating up of the fixed catalyst bed (through which the specified diluted molecular hydrogen as described above continuously flows during the heating up) to the 450° C. takes place through applying the following temperature-programmed procedure:

Starting at ambient temperature (about 25° C.) the fixed bed is initially heated up to 250° C. (always the temperature at the metering point of the thermocouple) at a rate of 10° C. per minute. Then, the temperature of the fixed bed is kept at this intermediate value for 25 minutes before it is first raised to 350° C. at a rate of 1° C. per minute and, after maintaining this temperature for 25 minutes, to 450° C. at the same heating rate. This temperature is then maintained for 10 hours for activation purposes as already mentioned. When activation is complete, the fixed bed temperature is increased to the target value of 950° C. (as always, the temperature at the metering point of the thermocouple) suitable for the intended synthesis gas production at a heating rate of 10° C. per minute and maintained at this temperature for 1 hour.

Prior to introducing the reaction gas mixture into the fixed bed charged steam reformer tubular reactor, the stream of diluted hydrogen is switched to a stream of diluted steam (20% by vol. $H_2O$ and 80% by vol. $N_2$ (of the purity 4.0)). The total gas flow of 1.33 l (STP)/min and the pressure of 20 bar at the tubular reactor inlet is maintained as well as the 950° C. This measure helps to avoid coke formation upon reaction gas entry into the reaction tube.

To start synthesis gas formation the 80% by vol. $N_2$ content of the diluted steam stream (subject to retention of the other operating conditions) are replaced by the same content (80% by vol.) of the off-gas.

In case of off-gas discharged in this Example 1 from the process carried out for production of the target product acrylic acid the synthesis gas flowing out of the bottom of the reaction tube will have the following composition (the data presented are derived from results obtained in comparable single tube experiments applying corresponding catalyst charges and similar/equivalent starting reaction gas mixtures and reaction conditions):

| | |
|---|---|
| 0.00% by vol. of | formaldehyde |
| 0.00% by vol. of | acrolein |
| 0.00% by vol. of | molecular nitrogen |
| 2.69% by vol. of | water |
| 0.00% by vol. of | acetic acid |
| 0.00% by vol. of | acrylic acid |
| 0.00% by vol. of | propene |
| 2.69% by vol. of | propane |
| 0.00% by vol. of | methane |
| 0.00% by vol. of | molecular oxygen |
| 17.23% by vol. of | carbon dioxide |
| 39.26% by vol. of | carbon monoxide |
| 38.13% by vol. of | molecular hydrogen |

The resulting synthesis gas is rich in molecular hydrogen and carbon monoxide and may be used as such for the synthesis of chemical compounds containing C and H and optionally O. Before such using $H_2O$ still contained in it can easily be separated by condensation measures if so desired. Alternatively, the resulting synthesis gas can be mixed with any other synthesis gas produced in any plant (e.g. coal gasification plants) dedicated to production of synthesis gas and only the resulting mixture of the synthesis gases is applied for the synthesis of above-mentioned chemical compounds. Instead of using off-gas discharged from any inventive process as such for production of synthesis gas, such off-gas may be mixed with other raw materials (e.g. a mixture of steam and methane) normally fed in any plant (e.g. a tubular methane reformer) dedicated to production of synthesis gas and subsequently the resulting mixture will be fed into such dedicated synthesis gas production plant.

The syngas resulting in this Example 1 is insofar particularly valuable because it contains carbon dioxide as well as molecular hydrogen and carbon monoxide. This is because e.g. methanol may be generated from carbon monoxide as well as from carbon dioxide ($2H_2+CO\leftrightarrow CH_3OH$ and $3H_2+CO_2\leftrightarrow CH_3OH$ and $H_2O$). The preferred reaction path goes via carbon monoxide, some carbon dioxide is required for kinetic reasons. The concentration ratio $R^C=(c_{H2}-c_{CO2})/(c_{CO}+c_{CO2})$ should generally between 2.0 and 2.2 (see e.g. Ullmann's Encyclopedia of Industrial Chemistry, Fifth Completely Revised Edition, Volume A12 (Formamides to Hexamethylendiamine), VCH Verlagsgesellschaft mbH, D-6940 Weinheim, page 174). The syngas resulting in this Example 1 has a value $R^C$ of only +0.37. However, this value can easily be increased to a value between 2.0 to 2.2 by adding to the syngas a corresponding amount of molecular hydrogen before carrying out the relevant synthesis reaction.

Through addition of molecular hydrogen (this and the previously addressed molecular hydrogen advantageously may result in a propane dehydrogenation which is used for production of propene raw material used for preparing starting reaction gas mixture 1) to the off-gas discharged in this Example 1 from the process carried out for production of the target product acrylic acid before using said off-gas for the production of synthesis gas as outlined above even enables the production of syngas whose carbon dioxide content is negligible and which contains carbon monoxide and molecular hydrogen in the molar ratio 1:1.

Such syngas preferably is applicable for hydroformylation of olefins (especially propene) as described in WO 2002/000587, WO 2017/108878, WO 2018/210720 and WO 2005/095315. The aldehydes (especially butyraldehyde) resulting in such hydroformylation reaction subsequently may be hydrogenated to yield the corresponding alcohols (especially n-butanol), which finally may be esterified through reaction with acrylic acid (preferably produced by a process as claimed in this application) to yield the corresponding acrylate (especially butyl acrylate). In case the hydrocarbon content of the off-gas would not be enough for an adequate application of reaction a) (heterogeneously catalyzed steam reforming of hydrocarbon contained in the off-gas), such hydrocarbon easily can be added to the off-gas before it is used for production of syngas (preferably such hydrocarbon is already part of starting reaction gas mixture 1).

Regardless of how the off-gas resulting in this Example 1 is used in detail for the production of synthesis gas and how such synthesis gas produced is used in detail for the production of chemical compounds, all the procedures described above have in common, that any "C" contained in any compound of the off-gas is no longer combusted to yield $CO_2$ but advantageously used for the synthesis of "C"-containing molecules.

An economic implementation of what has been said above presupposes, however, that the relevant off-gas has only a limited content of molecular nitrogen. This is because such molecular nitrogen will finally be contained in the resulting synthesis gas. Chemical synthesis processes based on synthesis gas (such as hydroformylation of e.g. propene) normally are however continuous processes which do not result in 100% conversion of the starting materials (e.g. propene) involved. Accordingly, the resulting product mixtures still contain unreacted raw material and the inert molecular nitrogen. It is of course economically desirable that said unreacted raw materials be recycled into the respective synthesis process.

However, for the continuous chemical synthesis gas process (e.g. hydroformylation) being operated successfully on an industrial scale, it is important to establish a steady state between the feed materials, including any recycle, and the degree of reaction. It is therefore important to prevent excessive $N_2$ build-up in the reaction system due to recycle of the unreacted components. However, molecular nitrogen is difficult to separate from other compounds involved such as CO, $CO_2$, propene, $H_2$ and others. Thus, to prevent significant $N_2$ build up due to recycle, it is necessary to vent off at least some of the molecular nitrogen. This removal is all the more pronounced, as higher the $N_2$ content of the off-gas used for syngas production is. As any such $N_2$ removal necessarily also will involve the removal of some remaining raw material, it automatically will cause some undesired inefficiencies and economic debits in the process.

Example 2

A Steady State is Described (small amounts of $O_2$ dissolved in the liquid material flows are not included (addressed) in the following)

Starting reaction gas mixture 1 is a mixture of the following feed gas streams:

16534 kg/h molecular oxygen (purity: 99.9999% by wt. of $O_2$);

16000 kg/h polymer grade propene (99.48% by wt. propene and 0.52% by wt. propane);

203356 kg/h recycled gaseous stream P; and 158.9 kg/h $CH_4$ (purity: 99.999% by wt.).

The temperature of starting reaction gas mixture 1 is 200° C. and its pressure is 2.434 bar. The composition of starting reaction gas mixture 1 fed through the reaction tubes first stage tube bundle reactor is:

| 0.05% by vol. of | formaldehyde |
|---|---|
| 0.02% by vol. of | acrolein |
| 2.07% by vol. of | water |
| 0.03% by vol. of | acetic acid |
| 0.03% by vol. of | acrylic acid |
| 6.00% by vol. of | propene |
| 1.80% by vol. of | propane |
| 9.43% by vol. of | methane |
| 10.80% by vol. of | molecular oxygen |
| 47.77% by vol. of | carbon dioxide |
| 22.00% by vol. of | carbon monoxide |

Temperature $T^A$ is 329° C. Temperature $T^B$ is 336° C.

The temperature in the catalytically active part of the fixed catalyst bed in the reaction tube is in the range of 326° C. to 403° C.

The propene hourly space velocity on the fixed catalyst bed (Section 2+Section 3 in the reaction tube) is 172 (l (STP)/l·h).

The single pass propene conversion is 95.8 mol % and the accompanying selectivity $S^A$ of the formation of acrolein is 91.7 mol %.

The stream of 236048 kg/h of product gas mixture 1 leaving the first reaction stage with a temperature of 360° C. and a pressure of 1.834 bar has the following composition:

| 0.05% by vol. of | formaldehyde |
|---|---|
| 5.30% by vol. of | acrolein |
| 8.08% by vol. of | water |
| 0.13% by vol. of | acetic acid |
| 0.27% by vol. of | acrylic acid |
| 0.25% by vol. of | propene |
| 1.80% by vol. of | propane |
| 9.43% by vol. of | methane |
| 4.38% by vol. of | molecular oxygen |
| 48.13% by vol. of | carbon dioxide |
| 22.18% by vol. of | carbon monoxide |

The temperature of the product gas mixture leaving the first reaction stage (product gas mixture 1) is reduced by indirect cooling in the after cooler. The stream of thus cooled product gas mixture 1 (temperature=250° C.) is mixed with a stream of 3792.4 kg/h secondary molecular oxygen (purity: 99.9999% by wt. of $O_2$; temperature: 165.00° C.; pressure: 2.50 bar).

The composition of the 239841 kg/h of thus resulting starting reaction gas mixture 2 (temperature: 249.0° C.; pressure: 1.809 bar) fed through the reaction tubes of the second stage tube bundle reactor is:

| 0.05% by vol. of | formaldehyde |
|---|---|
| 5.20% by vol. of | acrolein |
| 7.94% by vol. of | water |
| 0.13% by vol. of | acetic acid |
| 0.27% by vol. of | acrylic acid |
| 0.24% by vol. of | propene |
| 1.77% by vol. of | propane |
| 9.27% by wt. of | methane |
| 6.07% by vol. of | molecular oxygen |
| 47.27% by vol. of | carbon dioxide |
| 21.79% by vol. of | carbon monoxide |

Temperature $T^C$ is 268° C. Temperature $T^D$ is 273° C.

The temperature in the catalytically active part of the fixed catalyst bed in the reaction tube is in the range of 266° C. to 305° C.

The acrolein hourly space velocity on the fixed catalyst bed (Section 2 and Section 3 in the reaction tube) is 138 (l (STP)/l·h).

The single pass acrolein conversion is 99.5 mol % and the accompanying selectivity $S^{AA}$ of the formation of acrylic acid and assessed over both reaction stages and based on converted propene is 89.8 mol %.

The product gas mixture (239841 kg/h, T=250° C., P=1.509 bar) leaving the second stage reactor (product gas mixture 2) at its entrance into the separating zone is cooled in the spray cooler (quench 1) to a temperature of 120° C.

The composition of product gas mixture 2 is:

| 0.25% by vol. of | formaldehyde |
|---|---|
| 0.03% by vol. of | acrolein |
| 8.51% by vol. of | water |
| 0.02% by vol. of | formic acid |
| 0.15% by vol. of | acetic acid |
| 5.22% by vol. of | acrylic acid |
| 0.03% by vol. of | maleic anhydride |
| 0.25% by vol. of | propene |
| 1.81% by vol. of | propane |
| 9.47% by vol. of | methane |
| 3.00% by vol. of | molecular oxygen |
| 48.79% by vol. of | carbon dioxide |
| 22.47% by vol. of | carbon monoxide |

The liquid to be used for the direct cooling of the product gas mixture 2 (quench liquid 1) is a portion (516483 kg/h, T=116.2° C.) of bottoms liquid which is withdrawn in a total amount of 519893 kg/h (T=116.2° C.) from the bottom of the condensation column described below. Contents of this bottom liquid are:

| 0.72% by wt. of | water |
|---|---|
| 0.01% by wt. of | formic acid |
| 0.26% by wt. of | acetic acid |
| 41.11% by wt. of | acrylic acid |
| 0.03% by wt. of | propionic acid |
| 0.20% by wt. of | furfurals |
| 0.16% by wt. of | benzaldehyde |
| 5.95% by wt. of | maleic anhydride |
| 41.28% by wt. of | diacrylic acid |
| 0.77% by wt. of | MEHQ |
| 0.85% by wt. of | benzoic acid |
| 0.32% by wt. of | phthalic anhydride |
| 0.32% by wt. of | phenothiazine |
| 8.00% by wt. of | polyacrylic acid |
| 0.01% by wt. of | methylene glycol |
| 0.01% by wt. of | propane |

The mixture of product gas mixture cooled to 120° C. and unevaporated quench liquid 1 having same temperature which results in the direct cooling is conducted as such into the bottom of the condensation column. The pressure in the bottom space and in the quench 1 is 1.479 bar. The other portion (3410 kg/h) of bottoms liquid withdrawn from the bottom of the condensation column is supplied to the second stripping column and fed into its middle section.

The energy required for cracking diacrylic acid and polyacrylic acid (both Michael adducts) contained in the bottoms liquid into acrylic acid is supplied into the second stripping column by means of an external forced-circulation three-flow tube bundle flash evaporator, which is fed with bottoms liquid of the second stripping column. As it flows through the heat exchanger tubes, the bottoms liquid is heated, and its major amount thereafter recycled into the bottom of the second stripping column. A small amount of the total amount of bottoms liquid conducted through the heat exchanger is branched off, degassed and, diluted with methanol, sent to residue incineration.

In addition, the first laden gas conducted out of the first stripping column at the top thereof is fed into the bottom of the second stripping column. Second laden gas is conducted out of the top of the second stripping column in an amount of 18868 kg/h (temperature=65° C., pressure=1.40 bar) and fed into quench 1 and/or the bottom of the condensation column. Contents of the second laden gas are:

| 0.05% by vol. of | formaldehyde |
|---|---|
| 0.02% by vol. of | acrolein |
| 6.51% by vol. of | water |
| 0.46% by vol. of | acetic acid |
| 6.49% by vol. of | acrylic acid |
| 0.25% by vol. of | propene |
| 1.83% by vol. of | propane |
| 9.55% by vol. of | methane |
| 3.02% by vol. of | molecular oxygen |
| 49.16% by vol. of | carbon dioxide |
| 22.66% by vol. of | carbon monoxide |

88253 kg/h of high boiler fraction are conducted from the first collecting tray of the condensation column into the bottom space disposed below the first collecting tray. The high boiler fraction has, at a temperature of 103.2° C. and pressure of approximately 1.479 bar, the following contents:

| 0.01% by wt. of | formaldehyde |
|---|---|
| 1.32% by wt. of | water |
| 0.01% by wt. of | formic acid |
| 0.48% by wt. of | acetic acid |
| 91.94% by wt. of | acrylic acid |
| 0.07% by wt. of | propionic acid |
| 0.36% by wt. of | furfurals |
| 0.21% by wt. of | benzaldehyde |
| 4.41% by wt. of | maleic anhydride |
| 1.00% by wt. of | diacrylic acid |
| 0.070% by wt. of | MEHQ |
| 0.02% by wt. of | benzoic acid |
| 0.01% by wt. of | phthalic anhydride |
| 0.01% by wt. of | phenothiazine |
| 0.08% by wt. of | propane |

The bottom temperature is 116.2° C. and the bottom pressure (at the liquid level) is 1.479 bar. From the second collecting tray, 254449 kg/h crude acrylic acid with a temperature of 100.8° C. are withdrawn continuously at 1.443 bar as the first side draw, which has the following contents:

| 0.01% by wt. of | formaldehyde |
|---|---|
| 1.41% by wt. of | water |
| 0.02% by wt. of | formic acid |
| 0.90% by wt. of | acetic acid |
| 96.82% by wt. of | acrylic acid |
| 0.09% by wt. of | propionic acid |
| 0.16% by wt. of | furfurals |
| 0.03% by wt. of | benzaldehyde |
| 0.22% by wt. of | maleic anhydride |
| 0.30% by wt. of | diacrylic acid |
| 0.02% by wt. of | MEHQ |
| 0.01% by wt. of | phenothiazine |
| 0.01% by wt. of | propane |

43857 kg/h of the crude acrylic acid withdrawn from the second collecting tray, together with mother liquor (71694 kg/h) which has been obtained in the crystallizative further purification of withdrawn acrylic acid and has been heated to 90° C. in the indirect heat exchange with drawn crude acrylic acid and steam as heat carrier are recycled into the condensation column via respective inserted tubes immediately below the second collecting tray to the dual-flow tray which follows below the second collecting tray.

115000 kg/h of the crude acrylic acid withdrawn from the second collecting tray are with a temperature of 100.8° C. recycled directly above the second collecting tray through spray nozzles to keep this section wetted and prevent fouling.

95592 kg/h of the crude acrylic acid withdrawn from the second collecting tray are cooled to a temperature of 29° C. by the multistage indirect heat exchange. About 1000 kg/h of demineralized water are than added to the cooled acrylic acid.

The resulting mixture is cooled and subsequently crystallized in cooling disk crystallizers and the resulting crystal suspension purified in hydraulic melt wash columns as described in WO 2008/090190 on pages 49 and 50. From the melt circuits which are stabilized by the addition of a solution of MEHQ in glacial acrylic acid, 23898 kg/h of the desired separated acrylic acid are withdrawn as glacial acrylic acid showing the following contents:

| 0.01% by wt. of | water |
|---|---|
| 0.20% by wt. of | acetic acid |
| 99.75% by wt. of | acrylic acid |
| 0.03% by wt. of | propionic acid |
| 0.01% by wt. of | MEHQ |

In 904 kg/h of the aforementioned glacial acrylic acid 11 kg/h of PTZ (phenothiazine) are dissolved to prepare an inhibitor solution 1 at 25° C. The remaining flow of glacial acrylic acid continuously withdrawn from the melt circuits is fed continuously in the storage tank.

The mother liquor removed in the wash columns is initially conducted into a heatable collecting vessel and from there into a tank. From this tank it is (as already mentioned) heated to 90° C. with thermal integration and recycled in a mass flow of 71694 kg/h, together (as a mixed flow (94.1° C., 1.10 bar)) with 43857 kg/h of the crude acrylic acid withdrawn at the second collecting tray of the condensation column, to the condensation column at the upper part of the series of dual-flow trays below the second collecting tray.

The composition of the recycled mother liquor is as follows:

| 0.01% by wt. of | formaldehyde |
|---|---|
| 1.87% by wt. of | water |
| 0.02% by wt. of | formic acid |
| 1.13% by wt. of | acetic acid |
| 95.87% by wt. of | acrylic acid |
| 0.11% by wt. of | propionic acid |
| 0.21% by wt. of | furfurals |
| 0.04% by wt. of | benzaldehyde |
| 0.29% by wt. of | maleic anhydride |
| 0.40% by wt. of | diacrylic acid |
| 0.02% by wt. of | MEHQ |
| 0.01% by wt. of | phenothiazine |
| 0.01% by wt. of | methylene glycol |
| 0.01% by wt. of | propane |

841201 kg/h of acid water with a temperature of 58.5° C. and a pressure of 1.229 bar are withdrawn as the second side withdraw from the third collecting tray.

The acid water has the following contents:

| 0.09% by wt. of | formaldehyde |
|---|---|
| 0.01% by wt. of | acrolein |
| 0.02% by wt. of | allyl formate |
| 79.53% by wt. of | water |
| 0.51% by wt. of | formic acid |

-continued

| | |
|---|---|
| 5.56% by wt. of | acetic acid |
| 7.99% by wt. of | acrylic acid |
| 0.01% by wt. of | propionic acid |
| 6.28% by wt. of | methylene glycol |

31515 kg/h of the acid water withdrawn (58.5° C.) are recycled to the uppermost Thormann tray together with 35 kg/h of inhibitor solution 1 (25° C.) and 28 kg/h molten MEHQ (T=80° C.). 880 kg/h of inhibitor solution 1 are recycled (with a temperature of 25° C.) to the arrangement of the single-flow Thormann trays (approximately after two-thirds of the length of this Thormann separation section (counted from its bottom)).

458.73 m³/h of the acid water withdrawn are recycled at a temperature of 28.2° C. to the middle of an equidistant arrangement of valve trays which is described in more detail below (the cooling is effected by means of multistage indirect heat exchange).

325000 kg/h of the acid water withdrawn are recycled at a temperature of 23.3° C. to the uppermost of the aforementioned equidistant arrangement of valve trays (the cooling is effected together with the aforementioned amount of acid water by means of multistage indirect heat exchange; the last cooling stage from 28.2° C. to 23.3° C. is effected thermally and with heat integration (liquid chemical grade propene is used as the coolant and evaporates at the same time; the resulting gaseous propene is subsequently used for the configuration of the starting reaction gas mixture 1 for the first stage of the heterogeneously catalyzed gas-phase partial oxidation of propene). 9686 kg/h of the acid water withdrawn are fed to the extraction column for the purpose of the extraction still to be performed thereafter.

Above the third collecting tray in the condensation column is mounted a sequence of two-flow valve trays in equidistant arrangement. The pressure at the top of the condensation column is 1.17 bar. At the top of the condensation column 222658 kg/h of the residual gas mixture R leave the separating column with a temperature of 24° C. and the following contents:

| | |
|---|---|
| 0.06% by vol. of | formaldehyde |
| 0.03% by vol. of | acrolein |
| 2.39% by vol. of | water |
| 0.03% by vol. of | acetic acid |
| 0.04% by vol. of | acrylic acid |
| 0.28% by vol. of | propene |
| 2.06% by vol. of | propane |
| 10.76% by wt. of | methane |
| 3.41% by vol. of | molecular oxygen |
| 55.42% by vol. of | carbon dioxide |
| 25.52% by vol. of | carbon monoxide |

In an indirect heat exchanger the gas mixture R is heated to 32° C. 3303 kg/h thereof are discharged of the production process as off-gas stream O.

219356 kg/h of foresaid gas mixture R are compressed to a pressure of 2.5 bar by means of a compressor, which raises its temperature to approximately 150° C. 16000 kg/h thereof are fed to the first stripping column within the separating zone for stripping the extract from the acid water extraction. The remaining 203356 kg/h of the compressed gas mixture are (as cycle gas) recycled as gaseous stream P into the first reaction stage 1 as feed stream for preparing the stream of starting reaction gas mixture 1. The total of the mass flows of off-gas stream O and of cycle gaseous stream P constitutes the total mass flow M of residual gas mixture R which is continuously conducted out of the separating zone. It contains, of the total molar amount of those compounds contained in the product gas mixture 2 continuously transported into the separating zone, which have as pure compounds at a working pressure of 1 bar a boiling point below 250 K, 99.99 mol %.

The mass flow of the recycle gaseous stream P is 98.40% of the total mass flow M of residual gas mixture R which is continuously conducted out of the separating zone.

The 9686 kg/h of acid water to be extracted (temperature=58.5° C.) are fed into the extraction column below the lowermost packing via tubular distributors having appropriate passage orifices. Above the uppermost packing of the extraction column, a mixture (temperature=50° C.) of fresh Palatinol® A and extractant (in a ratio of the respective mass flows of 1:240) which has been recycled from the first stripping column and has been stripped free therein beforehand is introduced in a mass flow essentially equal to the 9686 kg/h of acid water. The recycled extractant has the following contents:

| | |
|---|---|
| ≤0.5% by wt. of | acrylic acid |
| ≤0.03% by wt. of | acetic acid |
| ≤0.02% by wt. of | water |
| ≤0.001% by wt. of | formic acid |
| ≤0.0035% by wt. of | acrolein |
| ≤0.00005% by wt. of | propionic acid |
| ≤0.0001% by wt. of | furfurals |
| ≤0.001% by wt. of | allyl formate |
| ≤0.03% by wt. of | MEHQ |
| ≥99.5% by wt. of | Palatinol ® A |

The specific mass of the acid water (temperature=58.5° C.) is 1013.4 kg/m³. The extractant is likewise introduced via tubular distributors having appropriate passage orifices. The acid water forms the continuous phase and the extractant forms the phase dispersed in droplet form (droplet diameter in the range from 2 to 5 mm), which descends in the aqueous phase. At the top of the extraction column the raffinate is withdrawn. It is sent to incineration. The extract is withdrawn from the bottom of the extraction column. It contains the acrylic acid extracted from the acid water. The entirety of the extract is conducted to the top of the first stripping column. Beforehand the extract is heated to 95° C. by indirect heat exchange in a plate heat exchanger. The heat carrier is bottom liquids withdrawn at the first stripping column.

Below the lowermost dual-flow tray the 16000 kg/h of the compressed residual gas mixture R (2.5 bar, 150° C.) are conducted into the first stripping column, where it ascends in countercurrent to the extract descending in the stripping column. At the top of the first stripping column first laden (especially with water and acrylic acid) gas is conducted out (16868 kg/h) and fed into the second stripping column. The composition of the first laden gas is:

| | |
|---|---|
| 0.05% by vol. of | formaldehyde |
| 0.03% by vol. of | acrolein |
| 6.89% by vol. of | water |
| 0.42% by vol. of | acetic acid |
| 1.09% by vol. of | acrylic acid |
| 0.27% by vol. of | propene |
| 1.93% by vol. of | propane |
| 10.11% by vol. of | methane |
| 3.20% by vol. of | molecular oxygen |
| 52.04% by vol. of | carbon dioxide |
| 23.97% by vol. of | carbon monoxide |

Bottoms liquid is withdrawn continuously from the bottom of the first stripping column. One portion of the bottoms liquid withdrawn from the first stripping column are cooled by two-stage indirect heat exchange (the first stage in a plate heat exchanger with thermal integration against extract), and recycled as extractant to the top of the extraction column. The other portion of bottoms liquid withdrawn from the first stripping column are heated to about 160° C. in an external force-circulation tube bundle flash evaporator and recycled into the bottom of the first stripping column.

The overall propene conversion (based on multiple pass) in this Example 1 is 99.93 mol % (calculated from the difference between propene fed as content of the chemical grade propene via starting reaction gas mixture 1 into the production process and propene discharged of the production process as content of off-gas stream O).

The overall yield of acrylic acid produced in Example 1 is 87.4 mol % (calculated from acrylic acid continuously fed into the storage tank as content of glacial acrylic acid and propene fed into the production process as content of chemical grade propene via starting reaction gas mixture 1).

From the acrylic acid contained in product gas mixture 2 99.36 mol % are in the separating zone transferred into the liquid phase.

Production of Synthesis Gas from the Off-Gas of this Example 2

The off-gas discharged in this Example 2 from the process carried out for production of the target product acrylic acid directly can be used as raw material for production of synthesis gas. On a laboratory scale this production advantageously will be carried out in the same manner as described in detail in Example 1 hereof. The only difference is to replace as raw material for the production process the off-gas produced in Example 1 hereof by the off-gas produced in this Example 2 (all other operating conditions are retained as in Example 1). The synthesis gas flowing out of the bottom of the reaction tube will have the following composition:

| | |
|---|---|
| 0.00% by vol. of | formaldehyde |
| 0.00% by vol. of | acrolein |
| 0.00% by vol. of | molecular nitrogen |
| 5.64% by vol. of | water |
| 0.00% by vol. of | acetic acid |
| 0.00% by vol. of | acrylic acid |
| 0.00% by vol. of | propene |
| 0.19% by vol. of | propane |
| 2.32% by vol. of | methane |
| 0.00% by vol. of | molecular oxygen |
| 45.33% by vol. of | carbon dioxide |
| 18.39% by vol. of | carbon monoxide |
| 28.13% by vol. of | molecular hydrogen |

The $R^C$ value of this syngas is −0.27.

All other statements made in Example 1 hereof apply correspondingly.

Example 3

A Steady State is Described (small amounts of $O_2$ dissolved in the liquid material flows are not included (addressed) in the following)

Starting reaction gas mixture 1 is a mixture of the following feed gas streams:

17494 kg/h molecular oxygen (purity: 99.9999% by wt. of $O_2$);

16000 kg/h chemical grade propene (94.77% by wt. propene and 5.23% by wt. propane);

63462 kg/h recycled gaseous stream P; and 27228 kg/h $CH_4$ (purity: 99.999% by wt.).

The temperature of starting reaction gas mixture 1 is 200° C. and its pressure is 2.434 bar. The composition of starting reaction gas mixture 1 fed through the reaction tubes first stage tube bundle reactor is:

| | |
|---|---|
| 0.03% by vol. of | formaldehyde |
| 0.02% by vol. of | acrolein |
| 1.37% by vol. of | water |
| 0.02% by vol. of | acetic acid |
| 0.02% by vol. of | acrylic acid |
| 6.00% by vol. of | propene |
| 0.88% by vol. of | propane |
| 78.74% by wt, of | methane |
| 10.80% by vol. of | molecular oxygen |
| 1.45% by vol. of | carbon dioxide |
| 0.67% by vol. of | carbon monoxide |

Temperature $T^A$ is 326° C. Temperature $T^B$ is 335° C.

The temperature in the catalytically active part of the fixed catalyst bed in the reaction tube is in the range of 325° C. to 400° C.

The propene hourly space velocity on the fixed catalyst bed (Section 2+Section 3 in the reaction tube) is 162 (l (STP)/l·h).

The single pass propene conversion is 95.8 mol % and the accompanying selectivity $S^A$ of the formation of acrolein is 91.7 mol %.

The stream of 124184 kg/h of product gas mixture 1 leaving the first reaction stage with a temperature of 360° C. and a pressure of 1.834 bar has the following composition:

| | |
|---|---|
| 0.03% by vol. of | formaldehyde |
| 5.29% by vol. of | acrolein |
| 7.40% by vol. of | water |
| 0.12% by vol. of | acetic acid |
| 0.26% by vol. of | acrylic acid |
| 0.25% by vol. of | propene |
| 0.88% by vol. of | propane |
| 78.76% by vol. of | methane |
| 4.38% by vol. of | molecular oxygen |
| 1.79% by vol. of | carbon dioxide |
| 0.84% by vol. of | carbon monoxide |

The temperature of the product gas mixture leaving the first reaction stage (product gas mixture 1) is reduced by indirect cooling in the after cooler. The stream of thus cooled product gas mixture 1 (temperature=250° C.) is mixed with a stream of 3554 kg/h secondary molecular oxygen (purity: 99.9999% by wt. of $O_2$; temperature: 165.00° C.; pressure: 2.50 bar).

The composition of the 127737 kg/h of thus resulting starting reaction gas mixture 2 (temperature: 249.1° C.; pressure: 1.809 bar) fed through the reaction tubes of the second stage tube bundle reactor is:

| | |
|---|---|
| 0.03% by vol. of | formaldehyde |
| 5.19% by vol. of | acrolein |
| 7.28% by vol. of | water |
| 0.12% by vol. of | acetic acid |
| 0.26% by vol. of | acrylic acid |
| 0.24% by vol. of | propene |
| 0.86% by vol. of | propane |
| 77.37% by vol. of | methane |
| 6.07% by vol. of | molecular oxygen |
| 1.76% by vol. of | carbon dioxide |
| 0.82% by vol. of | carbon monoxide |

Temperature $T^C$ is 266° C. Temperature $T^D$ is 271° C.

The temperature in the catalytically active part of the fixed catalyst bed in the reaction tube is in the range of 265° C. to 301° C.

The acrolein hourly space velocity on the fixed catalyst bed (Section 2 and Section 3 in the reaction tube) is 130 (1 (STP)/l·h).

The single pass acrolein conversion is 99.5 mol % and the accompanying selectivity $S^{AA}$ of the formation of acrylic acid and assessed over both reaction stages and based on converted propene is 89.7 mol %.

The product gas mixture (127737 kg/h, T=250° C., P=1.509 bar) leaving the second stage reactor (product gas mixture 2) at its entrance into the separating zone is cooled in the spray cooler (quench 1) to a temperature of 120° C.

The composition of product gas mixture 2 is:

| | |
|---|---|
| 0.23% by vol. of | formaldehyde |
| 0.03% by vol. of | acrolein |
| 7.83% by vol. of | water |
| 0.02% by vol. of | formic acid |
| 0.14% by vol. of | acetic acid |
| 5.20% by vol. of | acrylic acid |
| 0.03% by vol. of | maleic anhydride |
| 0.25% by vol. of | propene |
| 0.88% by vol. of | propane |
| 79.13% by vol. of | methane |
| 3.00% by vol. of | molecular oxygen |
| 2.23% by vol. of | carbon dioxide |
| 1.03% by vol. of | carbon monoxide |

The liquid to be used for the direct cooling of the product gas mixture 2 (quench liquid 1) is a portion (513405 kg/h, T=116.1° C.) of bottoms liquid which is withdrawn in a total amount of 516815 kg/h (T=116.1° C.) from the bottom of the condensation column described below. Contents of this bottom liquid are:

| | |
|---|---|
| 0.63% by wt. of | water |
| 0.01% by wt. of | formic acid |
| 0.24% by wt. of | acetic acid |
| 39.57% by wt. of | acrylic acid |
| 0.03% by wt. of | propionic acid |
| 0.19% by wt. of | furfurals |
| 0.15% by wt. of | benzaldehyde |
| 5.59% by wt. of | maleic anhydride |
| 43.39% by wt. of | diacrylic acid |
| 0.77% by wt. of | MEHQ |
| 0.80% by wt. of | benzoic acid |
| 0.30% by wt. of | phthalic anhydride |
| 0.32% by wt. of | phenothiazine |
| 8.00% by wt. of | polyacrylic acid |
| 0.01% by wt. of | methylene glycol |

The mixture of product gas mixture cooled to 120° C. and unevaporated quench liquid 1 having same temperature which results in the direct cooling is conducted as such into the bottom of the condensation column. The pressure in the bottom space and in the quench 1 is 1.479 bar. The other portion (3410 kg/h) of bottoms liquid withdrawn from the bottom of the condensation column is supplied to the second stripping column and fed into its middle section.

The energy required for cracking diacrylic acid and polyacrylic acid (both Michael adducts) contained in the bottoms liquid into acrylic acid is supplied into the second stripping column by means of an external forced-circulation three-flow tube bundle flash evaporator, which is fed with bottoms liquid of the second stripping column. As it flows through the heat exchanger tubes, the bottoms liquid is heated, and its major amount thereafter recycled into the bottom of the second stripping column. A small amount of the total amount of bottoms liquid conducted through the heat exchanger is branched off, degassed and, diluted with methanol, sent to residue incineration.

In addition, the first laden gas conducted out of the first stripping column at the top thereof is fed into the bottom of the second stripping column. Second laden gas is conducted out of the top of the second stripping column in an amount of 18860 kg/h (temperature=65° C., pressure=1.40 bar) and fed into quench 1 and/or the bottom of the condensation column. Contents of the second laden gas are:

| | |
|---|---|
| 0.05% by vol. of | formaldehyde |
| 0.03% by vol. of | acrolein |
| 4.56% by vol. of | water |
| 0.27% by vol. of | acetic acid |
| 3.43% by vol. of | acrylic acid |
| 0.26% by vol. of | propene |
| 0.94% by vol. of | propane |
| 83.82% by vol. of | methane |
| 3.18% by vol. of | molecular oxygen |
| 2.37% by vol. of | carbon dioxide |
| 1.09% by vol. of | carbon monoxide |

85403 kg/h of high boiler fraction are conducted from the first collecting tray of the condensation column into the bottom space disposed below the first collecting tray. The high boiler fraction has, at a temperature of 102.3° C. and pressure of approximately 1.479 bar, the following contents:

| | |
|---|---|
| 0.01% by wt. of | formaldehyde |
| 1.20% by wt. of | water |
| 0.01% by wt. of | formic acid |
| 0.46% by wt. of | acetic acid |
| 92.28% by wt. of | acrylic acid |
| 0.07% by wt. of | propionic acid |
| 0.35% by wt. of | furfurals |
| 0.21% by wt. of | benzaldehyde |
| 4.29% by wt. of | maleic anhydride |
| 1.01% by wt. of | diacrylic acid |
| 0.07% by wt. of | MEHQ |
| 0.02% by wt. of | benzoic acid |
| 0.01% by wt. of | phthalic anhydride |
| 0.01% by wt. of | phenothiazine |

The bottom temperature is 116.1° C. and the bottom pressure (at the liquid level) is 1.479 bar. From the second collecting tray, 252432 kg/h crude acrylic acid with a temperature of 100.0° C. are withdrawn continuously at 1.443 bar as the first side draw, which has the following contents:

| | |
|---|---|
| 0.01% by wt. of | formaldehyde |
| 1.27% by wt. of | water |
| 0.02% by wt. of | formic acid |
| 0.90% by wt. of | acetic acid |
| 97.01% by wt. of | acrylic acid |
| 0.09% by wt. of | propionic acid |
| 0.15% by wt. of | furfurals |
| 0.03% by wt. of | benzaldehyde |
| 0.21% by wt. of | maleic anhydride |
| 0.28% by wt. of | diacrylic acid |
| 0.02% by wt. of | MEHQ |
| 0.01% by wt. of | phenothiazine |

47690 kg/h of the crude acrylic acid withdrawn from the second collecting tray, together with mother liquor (67306 kg/h) which has been obtained in the crystallizative further purification of withdrawn acrylic acid and has been heated to 90° C. in the indirect heat exchange with drawn crude acrylic acid and steam as heat carrier are recycled into the condensation column via respective inserted tubes immediately below the second collecting tray to the dual-flow tray which follows below the second collecting tray.

115000 kg/h of the crude acrylic acid withdrawn from the second collecting tray are with a temperature of 100.0° C. recycled directly above the second collecting tray through spray nozzles to keep this section wetted and prevent fouling.

89741 kg/h of the crude acrylic acid withdrawn from the second collecting tray are cooled to a temperature of 29° C. by the multistage indirect heat exchange. About 1000 kg/h of demineralized water are than added to the cooled acrylic acid.

The resulting mixture is cooled and subsequently crystallized in cooling disk crystallizers and the resulting crystal suspension purified in hydraulic melt wash columns as described in WO 2008/090190 on pages 49 and 50. From the melt circuits which are stabilized by the addition of a solution of MEHQ in glacial acrylic acid, 22435 kg/h of the desired separated acrylic acid are withdrawn as glacial acrylic acid showing the following contents:

| | |
|---|---|
| 0.01% by wt. of | water |
| 0.20% by wt. of | acetic acid |
| 99.75% by wt. of | acrylic acid |
| 0.03% by wt. of | propionic acid |
| 0.01% by wt. of | MEHQ |

In 904 kg/h of the aforementioned glacial acrylic acid 11 kg/h of PTZ (phenothiazine) are dissolved to prepare an inhibitor solution 1 at 25° C. The remaining flow of glacial acrylic acid continuously withdrawn from the melt circuits is fed continuously in the storage tank.

The mother liquor removed in the wash columns is initially conducted into a heatable collecting vessel and from there into a tank. From this tank it is (as already mentioned) heated to 90° C. with thermal integration and recycled in a mass flow of 67306 kg/h, together (as a mixed flow (94.2° C., 1.10 bar)) with 47690 kg/h of the crude acrylic acid withdrawn at the second collecting tray of the condensation column, to the condensation column at the upper part of the series of dual-flow trays below the second collecting tray.

The composition of the recycled mother liquor is as follows:

| | |
|---|---|
| 1.69% by wt. of | water |
| 0.02% by wt. of | formic acid |
| 1.15% by wt. of | acetic acid |
| 96.09% by wt. of | acrylic acid |
| 0.11% by wt. of | propionic acid |
| 0.20% by wt. of | furfurals |
| 0.03% by wt. of | benzaldehyde |
| 0.28% by wt. of | maleic anhydride |
| 0.38% by wt. of | diacrylic acid |
| 0.03% by wt. of | MEHQ |
| 0.01% by wt. of | phenothiazine |
| 0.01% by wt. of | propane |

839235 kg/h of acid water with a temperature of 57.2° C. and a pressure of 1.229 bar are withdrawn as the second side withdraw from the third collecting tray.

The acid water has the following contents:

| | |
|---|---|
| 0.09% by wt. of | formaldehyde |
| 0.01% by wt. of | acrolein |
| 0.02% by wt. of | allyl formate |
| 79.42% by wt. of | water |
| 0.54% by wt. of | formic acid |
| 5.90% by wt. of | acetic acid |
| 7.68% by wt. of | acrylic acid |
| 6.34% by wt. of | methylene glycol |

31052 kg/h of the acid water withdrawn (57.2° C.) are recycled to the uppermost Thormann tray together with 35 kg/h of inhibitor solution 1 (25° C.) and 28 kg/h molten MEHQ (T=80° C.). 880 kg/h of inhibitor solution 1 are recycled (with a temperature of 25° C.) to the arrangement of the single-flow Thormann trays (approximately after two-thirds of the length of this Thormann separation section (counted from its bottom)).

458.54 m³/h of the acid water withdrawn are recycled at a temperature of 28.2° C. to the middle of an equidistant arrangement of valve trays which is described in more detail below (the cooling is effected by means of multistage indirect heat exchange).

325000 kg/h of the acid water withdrawn are recycled at a temperature of 23.3° C. to the uppermost of the aforementioned equidistant arrangement of valve trays (the cooling is effected together with the aforementioned amount of acid water by means of multistage indirect heat exchange; the last cooling stage from 28.2° C. to 23.3° C. is effected thermally and with heat integration (liquid chemical grade propene is used as the coolant and evaporates at the same time; the resulting gaseous propene is subsequently used for the configuration of the starting reaction gas mixture 1 for the first stage of the heterogeneously catalyzed gas-phase partial oxidation of propene). 8183 kg/h of the acid water withdrawn are fed to the extraction column for the purpose of the extraction still to be performed thereafter.

Above the third collecting tray in the condensation column is mounted a sequence of two-flow valve trays in equidistant arrangement. The pressure at the top of the condensation column is 1.17 bar. At the top of the condensation column 113512 kg/h of the residual gas mixture R leave the separating column with a temperature of 24° C. and the following contents:

| | |
|---|---|
| 0.06% by vol. of | formaldehyde |
| 0.03% by vol. of | acrolein |
| 2.39% by vol. of | water |
| 0.03% by vol. of | acetic acid |
| 0.04% by vol. of | acrylic acid |
| 0.28% by vol. of | propene |
| 1.00% by vol. of | propane |
| 89.12% by wt. of | methane |
| 3.38% by vol. of | molecular oxygen |
| 2.51% by vol. of | carbon dioxide |
| 1.16% by vol. of | carbon monoxide |

In an indirect heat exchanger the gas mixture R is heated to 32° C. 34051 kg/h thereof are discharged of the production process as off-gas stream O.

79462 kg/h of foresaid gas mixture R are compressed to a pressure of 2.5 bar by means of a compressor, which raises its temperature to approximately 150° C. 16000 kg/h thereof are fed to the first stripping column within the separating zone for stripping the extract from the acid water extraction. The remaining 63462 kg/h of the compressed gas mixture are (as cycle gas) recycled as gaseous stream P into the first reaction stage 1 as feed stream for preparing the stream of starting reaction gas mixture 1. The total of the mass flows off-gas stream O and of cycle gaseous stream P constitutes the total mass flow M of residual gas mixture R which is continuously conducted out of the separating zone. It contains, of the total molar amount of those compounds contained in the product gas mixture 2 continuously transported into the separating zone, which have as pure compounds at a working pressure of 1 bar a boiling point below 250 K, 99.99 mol %.

The mass flow of the recycle gaseous stream P is 65.08% of the total mass flow M of residual gas mixture R which is continuously conducted out of the separating zone.

The 8183 kg/h of acid water to be extracted (temperature=57.2° C.) are fed into the extraction column below the lowermost packing via tubular distributors having appropriate passage orifices. Above the uppermost packing of the extraction column, a mixture (temperature=50° C.) of fresh Palatinol® A and extractant (in a ratio of the respective mass flows of 1:240) which has been recycled from the first stripping column and has been stripped free therein beforehand is introduced in a mass flow essentially equal to the 8183 kg/h of acid water. The recycled extractant has the following contents:

| | |
|---|---|
| ≤0.5% by wt. of | acrylic acid |
| ≤0.03% by wt. of | acetic acid |
| ≤0.02% by wt. of | water |
| ≤0.001% by wt. of | formic acid |
| ≤0.0035% by wt. of | acrolein |
| ≤0.00005% by wt. of | propionic acid |
| ≤0.0001% by wt. of | furfurals |
| ≤0.001% by wt. of | allyl formate |
| ≤0.03% by wt. of | MEHQ |
| ≤99.5% by wt. of | Palatinol ® A |

The specific mass of the acid water (temperature=57.2° C.) is 1014.8 kg/m³. The extractant is likewise introduced via tubular distributors having appropriate passage orifices. The acid water forms the continuous phase and the extractant forms the phase dispersed in droplet form (droplet diameter in the range from 2 to 5 mm), which descends in the aqueous phase. At the top of the extraction column the raffinate is withdrawn. It is sent to incineration. The extract is withdrawn from the bottom of the extraction column. It contains the acrylic acid extracted from the acid water. The entirety of the extract is conducted to the top of the first stripping column. Beforehand the extract is heated to 95° C. by indirect heat exchange in a plate heat exchanger. The heat carrier is bottom liquids withdrawn at the first stripping column.

Below the lowermost dual-flow tray the 16000 kg/h of the compressed residual gas mixture R (2.5 bar, 150° C.) are conducted into the first stripping column, where it ascends in countercurrent to the extract descending in the stripping column. At the top of the first stripping column first laden (especially with water and acrylic acid) gas is conducted out (16860 kg/h) and fed into the second stripping column. The composition of the first laden gas is:

| | |
|---|---|
| 0.06% by vol. of | formaldehyde |
| 0.03% by vol. of | acrolein |
| 4.69% by vol. of | water |
| 0.25% by vol. of | acetic acid |
| 0.55% by vol. of | acrylic acid |
| 0.27% by vol. of | propene |
| 0.96% by vol. of | propane |

-continued

| | |
|---|---|
| 86.35% by vol. of | methane |
| 3.27% by vol. of | molecular oxygen |
| 2.45% by vol. of | carbon dioxide |
| 1.12% by vol. of | carbon monoxide |

Bottoms liquid is withdrawn continuously from the bottom of the first stripping column. One portion of the bottoms liquid withdrawn from the first stripping column are cooled by two-stage indirect heat exchange (the first stage in a plate heat exchanger with thermal integration against extract), and recycled as extractant to the top of the extraction column. The other portion of bottoms liquid withdrawn from the first stripping column are heated to about 160° C. in an external force-circulation tube bundle flash evaporator and recycled into the bottom of the first stripping column.

The overall propene conversion (based on multiple pass) in this Example 1 is 98.50 mol % (calculated from the difference between propene fed as content of the chemical grade propene via starting reaction gas mixture 1 into the production process and propene discharged of the production process as content of off-gas stream O).

The overall yield of acrylic acid produced in Example 1 is 86.1 mol % (calculated from acrylic acid continuously fed into the storage tank as content of glacial acrylic acid and propene fed into the production process as content of chemical grade propene via starting reaction gas mixture 1).

From the acrylic acid contained in product gas mixture 2 99.37 mol % are in the separating zone transferred into the liquid phase.

Production of Synthesis Gas from the Off-Gas of this Example 3

The off-gas discharged in this Example 3 from the process carried out for production of the target product acrylic acid directly can be used as raw material for production of synthesis gas. On a laboratory scale this production advantageously will be carried out in the same manner as described in detail in Example 1 hereof. The only difference is to replace as raw material for the production process the off-gas produced in Example 1 hereof by the off-gas produced in this Example 3 (all other operating conditions are retained as in Example 1). The synthesis gas flowing out of the bottom of the reaction tube will have the following composition:

| | |
|---|---|
| 0.00% by vol. of | formaldehyde |
| 0.00% by vol. of | acrolein |
| 0.00% by vol. of | molecular nitrogen |
| 1.03% by vol. of | water |
| 0.00% by vol. of | acetic acid |
| 0.00% by vol. of | acrylic acid |
| 0.00% by vol. of | propene |
| 0.74% by vol. of | propane |
| 28.91% by vol. of | methane |
| 0.00% by vol. of | molecular oxygen |
| 0.32% by vol. of | carbon dioxide |
| 19.74% by vol. of | carbon monoxide |
| 49.26% by vol. of | molecular hydrogen |

The $R^C$ value of this syngas is +2.44. By an increase of the steam content in the mixture of steam and off-gas used for syngas production, the remaining content of methane in the resulting syngas can be reduced and the amounts of carbon monoxide and hydrogen in the resulting synthesis gas correspondingly increased.

All other statements made in Example 1 hereof apply correspondingly.

Example 4

A Steady State is Described (small amounts of $O_2$ dissolved in the liquid material flows are not included (addressed) in the following)

Starting reaction gas mixture 1 is a mixture of the following feed gas streams:

16336 kg/h of a mixture of molecular oxygen (96.60% by weight) and molecular nitrogen (3.40% by weight);

16000 kg/h chemical grade propene (94.77% by wt. propene and 5.23% by wt. propane); and 197861 kg/h recycled gaseous stream P.

The temperature of starting reaction gas mixture 1 is 200° C. and its pressure is 2.434 bar. The composition of starting reaction gas mixture 1 fed through the reaction tubes first stage tube bundle reactor is:

| | |
|---|---|
| 0.05% by vol. of | formaldehyde |
| 0.02% by vol. of | acrolein |
| 2.04% by vol. of | water |
| 0.03% by vol. of | acetic acid |
| 0.03% by vol. of | acrylic acid |
| 6.00% by vol. of | propene |
| 13.62% by vol. of | propane |
| 10.80% by vol. of | molecular oxygen |
| 34.19% by vol. of | carbon dioxide |
| 15.75% by vol. of | carbon monoxide |
| 17.47% by wt. of | molecular nitrogen |

Temperature $T^A$ is 327° C. Temperature $T^B$ is 335° C.

The temperature in the catalytically active part of the fixed catalyst bed in the reaction tube is in the range of 326° C. to 395° C.

The propene hourly space velocity on the fixed catalyst bed (Section 2+Section 3 in the reaction tube) is 164 (l (STP)/l·h).

The single pass propene conversion is 95.8 mol % and the accompanying selectivity $S^A$ of the formation of acrolein is 91.6 mol %.

The stream of 230197 kg/h of product gas mixture 1 leaving the first reaction stage with a temperature of 360° C. and a pressure of 1.834 bar has the following composition:

| | |
|---|---|
| 0.05% by vol. of | formaldehyde |
| 5.30% by vol. of | acrolein |
| 8.07% by vol. of | water |
| 0.13% by vol. of | acetic acid |
| 0.27% by vol. of | acrylic acid |
| 0.25% by vol. of | propene |
| 13.62% by vol. of | propane |
| 4.38% by vol. of | molecular oxygen |
| 34.54% by vol. of | carbon dioxide |
| 15.92% by vol. of | carbon monoxide |
| 17.47% by vol. of | molecular nitrogen |

The temperature of the product gas mixture leaving the first reaction stage (product gas mixture 1) is reduced by indirect cooling in the after cooler. The stream of thus cooled product gas mixture 1 (temperature=250° C.) is mixed with a stream of 3743 kg/h secondary mixture of molecular oxygen (96.60% by weight) and molecular nitrogen (3.40% by weight) having a temperature of 165.00° C. and a pressure of 2.50 bar.

The composition of the 233940 kg/h of thus resulting starting reaction gas mixture 2 (temperature: 249.1° C.; pressure: 1.809 bar) fed through the reaction tubes of the second stage tube bundle reactor is:

| | |
|---|---|
| 0.05% by vol. of | formaldehyde |
| 5.20% by vol. of | acrolein |
| 7.92% by vol. of | water |
| 0.13% by vol. of | acetic acid |
| 0.27% by vol. of | acrylic acid |
| 0.24% by vol. of | propene |
| 13.37% by vol. of | propane |
| 6.07% by vol. of | molecular oxygen |
| 33.90% by vol. of | carbon dioxide |
| 15.63% by vol. of | carbon monoxide |
| 17.22% by vol. of | molecular nitrogen |

Temperature $T^C$ is 267° C. Temperature $T^D$ is 272° C.

The temperature in the catalytically active part of the fixed catalyst bed in the reaction tube is in the range of 265° C. to 303° C.

The acrolein hourly space velocity on the fixed catalyst bed (Section 2 and Section 3 in the reaction tube) is 132 (l (STP)/l·h).

The single pass acrolein conversion is 99.5 mol % and the accompanying selectivity $S^{AA}$ of the formation of acrylic acid and assessed over both reaction stages and based on converted propene is 89.8 mol %.

The product gas mixture (233940 kg/h, T=250° C., P=1.509 bar) leaving the second stage reactor (product gas mixture 2) at its entrance into the separating zone is cooled in the spray cooler (quench 1) to a temperature of 120° C.

The composition of product gas mixture 2 is:

| | |
|---|---|
| 0.25% by vol. of | formaldehyde |
| 0.03% by vol. of | acrolein |
| 8.50% by vol. of | water |
| 0.02% by vol. of | formic acid |
| 0.15% by vol. of | acetic acid |
| 5.21% by vol. of | acrylic acid |
| 0.03% by vol. of | maleic anhydride |
| 0.25% by vol. of | propene |
| 13.67% by vol. of | propane |
| 3.00% by vol. of | molecular oxygen |
| 35.11% by vol. of | carbon dioxide |
| 16.17% by vol. of | carbon monoxide |
| 17.61% by vol. of | molecular nitrogen |

The liquid to be used for the direct cooling of the product gas mixture 2 (quench liquid 1) is a portion (522005 kg/h, T=116.4° C.) of bottoms liquid which is withdrawn in a total amount of 525415 kg/h (T=116.4° C.) from the bottom of the condensation column described below. Contents of this bottom liquid are:

| | |
|---|---|
| 0.71% by wt. of | water |
| 0.01% by wt. of | formic acid |
| 0.26% by wt. of | acetic acid |
| 44.65% by wt. of | acrylic acid |
| 0.04% by wt. of | propionic acid |
| 0.19% by wt. of | furfurals |
| 0.15% by wt. of | benzaldehyde |
| 5.67% by wt. of | maleic anhydride |
| 38.04% by wt. of | diacrylic acid |
| 0.77% by wt. of | MEHQ |
| 0.81% by wt. of | benzoic acid |
| 0.31% by wt. of | phthalic anhydride |
| 0.32% by wt. of | phenothiazine |
| 8.00% by wt. of | polyacrylic acid |
| 0.01% by wt. of | methylene glycol |
| 0.06% by wt. of | propane |

The mixture of product gas mixture cooled to 120° C. and unevaporated quench liquid 1 having same temperature which results in the direct cooling is conducted as such into the bottom of the condensation column. The pressure in the bottom space and in the quench 1 is 1.479 bar. The other portion (3410 kg/h) of bottoms liquid withdrawn from the bottom of the condensation column is supplied to the second stripping column and fed into its middle section.

The energy required for cracking diacrylic acid and poly-acrylic acid (both Michael adducts) contained in the bottoms liquid into acrylic acid is supplied into the second stripping column by means of an external forced-circulation three-flow tube bundle flash evaporator, which is fed with bottoms liquid of the second stripping column. As it flows through the heat exchanger tubes, the bottoms liquid is heated, and its major amount thereafter recycled into the bottom of the second stripping column. A small amount of the total amount of bottoms liquid conducted through the heat exchanger is branched off, degassed and, diluted with methanol, sent to residue incineration.

In addition, the first laden gas conducted out of the first stripping column at the top thereof is fed into the bottom of the second stripping column. Second laden gas is conducted out of the top of the second stripping column in an amount of 18858 kg/h (temperature=65° C., pressure=1.40 bar) and fed into quench 1 and/or the bottom of the condensation column. Contents of the second laden gas are:

| | |
|---|---|
| 0.05% by vol. of | formaldehyde |
| 0.02% by vol. of | acrolein |
| 6.62% by vol. of | water |
| 0.48% by vol. of | acetic acid |
| 6.61% by vol. of | acrylic acid |
| 0.25% by vol. of | propene |
| 13.74% by vol. of | propane |
| 3.01% by vol. of | molecular oxygen |
| 35.27% by vol. of | carbon dioxide |
| 16.25% by vol. of | carbon monoxide |
| 17.70% by vol. of | molecular nitrogen |

95593 kg/h of high boiler fraction are conducted from the first collecting tray of the condensation column into the bottom space disposed below the first collecting tray. The high boiler fraction has, at a temperature of 104.7° C. and pressure of approximately 1.479 bar, the following contents:

| | |
|---|---|
| 0.01% by wt. of | formaldehyde |
| 1.23% by wt. of | water |
| 0.01% by wt. of | formic acid |
| 0.46% by wt. of | acetic acid |
| 92.72% by wt. of | acrylic acid |
| 0.07% by wt. of | propionic acid |
| 0.31% by wt. of | furfurals |
| 0.18% by wt. of | benzaldehyde |
| 3.87% by wt. of | maleic anhydride |
| 0.98% by wt. of | diacrylic acid |
| 0.06% by wt. of | MEHQ |
| 0.02% by wt. of | benzoic acid |
| 0.01% by wt. of | phthalic anhydride |
| 0.01% by wt. of | phenothiazine |
| 0.06% by wt. of | propane |

The bottom temperature is 116.4° C. and the bottom pressure (at the liquid level) is 1.479 bar. From the second collecting tray, 259026 kg/h crude acrylic acid with a temperature of 102.4° C. are withdrawn continuously at 1.443 bar as the first side draw, which has the following contents:

| | |
|---|---|
| 0.01% by wt. of | formaldehyde |
| 1.30% by wt. of | water |
| 0.02% by wt. of | formic acid |
| 0.90% by wt. of | acetic acid |
| 96.92% by wt. of | acrylic acid |
| 0.09% by wt. of | propionic acid |
| 0.13% by wt. of | furfurals |
| 0.02% by wt. of | benzaldehyde |
| 0.19% by wt. of | maleic anhydride |
| 0.33% by wt. of | diacrylic acid |
| 0.02% by wt. of | MEHQ |
| 0.01% by wt. of | phenothiazine |
| 0.06% by wt. of | propane |

52939 kg/h of the crude acrylic acid withdrawn from the second collecting tray, together with mother liquor (68315 kg/h) which has been obtained in the crystallizative further purification of withdrawn acrylic acid and has been heated to 90° C. in the indirect heat exchange with drawn crude acrylic acid and steam as heat carrier are recycled into the condensation column via respective inserted tubes immediately below the second collecting tray to the dual-flow tray which follows below the second collecting tray.

115000 kg/h of the crude acrylic acid withdrawn from the second collecting tray are with a temperature of 102.4° C. recycled directly above the second collecting tray through spray nozzles to keep this section wetted and prevent fouling.

91087 kg/h of the crude acrylic acid withdrawn from the second collecting tray are cooled to a temperature of 29° C. by the multistage indirect heat exchange. About 1000 kg/h of demineralized water are than added to the cooled acrylic acid.

The resulting mixture is cooled and subsequently crystallized in cooling disk crystallizers and the resulting crystal suspension purified in hydraulic melt wash columns as described in WO 2008/090190 on pages 49 and 50. From the melt circuits which are stabilized by the addition of a solution of MEHQ in glacial acrylic acid, 22772 kg/h of the desired separated acrylic acid are withdrawn as glacial acrylic acid showing the following contents:

| | |
|---|---|
| 0.01% by wt. of | water |
| 0.20% by wt. of | acetic acid |
| 99.75% by wt. of | acrylic acid |
| 0.03% by wt. of | propionic acid |
| 0.01% by wt. of | MEHQ |

In 904 kg/h of the aforementioned glacial acrylic acid 11 kg/h of PTZ (phenothiazine) are dissolved to prepare an inhibitor solution 1 at 25° C. The remaining flow of glacial acrylic acid continuously withdrawn from the melt circuits is fed continuously in the storage tank.

The mother liquor removed in the wash columns is initially conducted into a heatable collecting vessel and from there into a tank. From this tank it is (as already mentioned) heated to 90° C. with thermal integration and recycled in a mass flow of 68315 kg/h, together (as a mixed flow (95.4° C., 1.10 bar)) with 52939 kg/h of the crude acrylic acid withdrawn at the second collecting tray of the condensation column, to the condensation column at the upper part of the series of dual-flow trays below the second collecting tray.

The composition of the recycled mother liquor is as follows:

| | |
|---|---|
| 0.01% by wt. of | formaldehyde |
| 1.73% by wt. of | water |
| 0.02% by wt. of | formic acid |
| 1.15% by wt. of | acetic acid |
| 95.97% by wt. of | acrylic acid |
| 0.11% by wt. of | propionic acid |
| 0.17% by wt. of | furfurals |
| 0.03% by wt. of | benzaldehyde |
| 0.26% by wt. of | maleic anhydride |
| 0.44% by wt. of | diacrylic acid |
| 0.02% by wt. of | MEHQ |
| 0.01% by wt. of | phenothiazine |
| 0.08% by wt. of | propane |

841777 kg/h of acid water with a temperature of 59.2° C. and a pressure of 1.229 bar are withdrawn as the second side withdraw from the third collecting tray.

The acid water has the following contents:

| | |
|---|---|
| 0.09% by wt. of | formaldehyde |
| 0.01% by wt. of | acrolein |
| 0.02% by wt. of | allyl formate |
| 79.75% by wt. of | water |
| 0.51% by wt. of | formic acid |
| 5.64% by wt. of | acetic acid |
| 7.71% by wt. of | acrylic acid |
| 6.27% by wt. of | methylene glycol |

32568 kg/h of the acid water withdrawn (59.2° C.) are recycled to the uppermost Thormann tray together with 35 kg/h of inhibitor solution 1 (25° C.) and 28 kg/h of molten MEHQ (T=80° C.). 880 kg/h of inhibitor solution 1 are recycled (with a temperature of 25° C.) to the arrangement of the single-flow Thormann trays (approximately after two-thirds of the length of this Thormann separation section (counted from its bottom)).

458.79 m³/h of the acid water withdrawn are recycled at a temperature of 28.2° C. to the middle of an equidistant arrangement of valve trays which is described in more detail below (the cooling is effected by means of multistage indirect heat exchange).

325000 kg/h of the acid water withdrawn are recycled at a temperature of 23.3° C. to the uppermost of the aforementioned equidistant arrangement of valve trays (the cooling is effected together with the aforementioned amount of acid water by means of multistage indirect heat exchange; the last cooling stage from 28.2° C. to 23.3° C. is effected thermally and with heat integration (liquid chemical grade propene is used as the coolant and evaporates at the same time; the resulting gaseous propene is subsequently used for the configuration of the starting reaction gas mixture 1 for the first stage of the heterogeneously catalyzed gas-phase partial oxidation of propene). 9209 kg/h of the acid water withdrawn are fed to the extraction column for the purpose of the extraction still to be performed thereafter.

Above the third collecting tray in the condensation column is mounted a sequence of two-flow valve trays in equidistant arrangement. The pressure at the top of the condensation column is 1.17 bar. At the top of the condensation column 218351 kg/h of the residual gas mixture R leave the separating column with a temperature of 24° C. and the following contents:

| | |
|---|---|
| 0.06% by vol. of | formaldehyde |
| 0.03% by vol. of | acrolein |
| 2.39% by vol. of | water |
| 0.03% by vol. of | acetic acid |
| 0.04% by vol. of | acrylic acid |
| 0.28% by vol. of | propene |
| 15.53% by vol. of | propane |
| 20.00% by wt. of | molecular nitrogen |
| 3.41% by vol. of | molecular oxygen |
| 39.87% by vol. of | carbon dioxide |
| 18.36% by vol. of | carbon monoxide |

In an indirect heat exchanger the gas mixture R is heated to 32° C. 4490 kg/h thereof are discharged of the production process as off-gas stream O.

213861 kg/h of foresaid gas mixture R are compressed to a pressure of 2.5 bar by means of a compressor, which raises its temperature to approximately 150° C. 16000 kg/h thereof are fed to the first stripping column within the separating zone for stripping the extract from the acid water extraction. The remaining 197861 kg/h of the compressed gas mixture are (as cycle gas) recycled as gaseous stream P into the first reaction stage 1 as feed stream for preparing the stream of starting reaction gas mixture 1. The total of the mass flows of off-gas stream O and of cycle gaseous stream P constitutes the total mass flow M of residual gas mixture R which is continuously conducted out of the separating zone. It contains, of the total molar amount of those compounds contained in the product gas mixture 2 continuously transported into the separating zone, which have as pure compounds at a working pressure of 1 bar a boiling point below 250 K, 99.99 mol %.

The mass flow of the recycle gaseous stream P is 97.78% of the total mass flow M of residual gas mixture R which is continuously conducted out of the separating zone.

The 9209 kg/h of acid water to be extracted (temperature=59.2° C.) are fed into the extraction column below the lowermost packing via tubular distributors having appropriate passage orifices. Above the uppermost packing of the extraction column, a mixture (temperature=50° C.) of fresh Palatinol® A and extractant (in a ratio of the respective mass flows of 1:240) which has been recycled from the first stripping column and has been stripped free therein beforehand is introduced in a mass flow essentially equal to the 9209 kg/h of acid water. The recycled extractant has the following contents:

| | |
|---|---|
| 0.5% by wt. of | acrylic acid |
| 0.03% by wt. of | acetic acid |
| 0.02% by wt. of | water |
| 0.001% by wt. of | formic acid |
| 0.0035% by wt. of | acrolein |
| 0.00005% by wt. of | propionic acid |
| 0.0001% by wt. of | furfurals |
| 0.001% by wt. of | allyl formate |
| 0.03% by wt. of | MEHQ |
| 99.5% by wt. of | Palatinol ® A |

The specific mass of the acid water (temperature=59.2° C.) is 1012.7 kg/m³. The extractant is likewise introduced via tubular distributors having appropriate passage orifices. The acid water forms the continuous phase and the extractant forms the phase dispersed in droplet form (droplet diameter in the range from 2 to 5 mm), which descends in the aqueous phase. At the top of the extraction column the raffinate is withdrawn. It is sent to incineration. The extract is withdrawn from the bottom of the extraction column. It contains the acrylic acid extracted from the acid water. The entirety of the extract is conducted to the top of the first stripping column. Beforehand the extract is heated to 95° C. by indirect heat exchange in a plate heat exchanger. The heat carrier is bottom liquids withdrawn at the first stripping column.

Below the lowermost dual-flow tray the 16000 kg/h of the compressed residual gas mixture R (2.5 bar, 150° C.) are conducted into the first stripping column, where it ascends in countercurrent to the extract descending in the stripping column. At the top of the first stripping column first laden (especially with water and acrylic acid) gas is conducted out (16858 kg/h) and fed into the second stripping column. The composition of the first laden gas is:

| | |
|---|---|
| 0.05% by vol. of | formaldehyde |
| 0.03% by vol. of | acrolein |
| 7.02% by vol. of | water |
| 0.44% by vol. of | acetic acid |
| 1.07% by vol. of | acrylic acid |
| 0.27% by vol. of | propene |
| 14.56% by vol. of | propane |
| 3.20% by vol. of | molecular oxygen |
| 37.39% by vol. of | carbon dioxide |
| 17.22% by vol. of | carbon monoxide |
| 18.75% by vol. of | molecular nitrogen |

Bottoms liquid is withdrawn continuously from the bottom of the first stripping column. One portion of the bottoms liquid withdrawn from the first stripping column are cooled by two-stage indirect heat exchange (the first stage in a plate heat exchanger with thermal integration against extract), and recycled as extractant to the top of the extraction column. The other portion of bottoms liquid withdrawn from the first stripping column are heated to about 160° C. in an external force-circulation tube bundle flash evaporator and recycled into the bottom of the first stripping column.

The overall propene conversion (based on multiple pass) in this Example 1 is 99.90 mol % (calculated from the difference between propene fed as content of the chemical grade propene via starting reaction gas mixture 1 into the production process and propene discharged of the production process as content of off-gas stream O).

The overall yield of acrylic acid produced in Example 1 is 87.4 mol % (calculated from acrylic acid continuously fed into the storage tank as content of glacial acrylic acid and propene fed into the production process as content of chemical grade propene via starting reaction gas mixture 1).

From the acrylic acid contained in product gas mixture 2 99.38 mol % are in the separating zone transferred into the liquid phase.

Production of Synthesis Gas from the Off-Gas of this Example 4

The off-gas discharged in this Example 4 from the process carried out for production of the target product acrylic acid directly can be used as raw material for production of synthesis gas. On a laboratory scale this production advantageously will be carried out in the same manner as described in detail in Example 1 hereof. The only difference is to replace as raw material for the production process the off-gas produced in Example 1 hereof by the off-gas produced in this Example 4 (all other operating conditions are retained as in Example 1). The synthesis gas flowing out of the bottom of the reaction tube will have the following composition:

| | |
|---|---|
| 0.00% by vol. of | formaldehyde |
| 0.00% by vol. of | acrolein |
| 9.16% by vol. of | molecular nitrogen |
| 1.23% by vol. of | water |
| 0.00% by vol. of | acetic acid |
| 0.00% by vol. of | acrylic acid |
| 0.00% by vol. of | propene |
| 0.96% by vol. of | propane |
| 0.00% by vol. of | methane |
| 0.00% by vol. of | molecular oxygen |
| 16.40% by vol. of | carbon dioxide |
| 31.25% by vol. of | carbon monoxide |
| 41.00% by vol. of | molecular hydrogen |

The $R^C$ value of this syngas is +0.52. By an increase of the steam content in the mixture of steam and off-gas used for syngas production, the remaining content of propane in the resulting syngas can be reduced and the amounts of carbon monoxide and hydrogen in the resulting synthesis gas correspondingly increased. Due to the increase in volume during the production of syngas (corresponding to the increase in the number of molecules), the concentration of molecular nitrogen at the transition from off-gas to syngas drops to an economically still acceptable level with a view to subsequent uses of the syngas produced. All other statements made in Example 1 hereof apply correspondingly.

Comparative Example

A Steady State is Described (small amounts of $O_2$ dissolved in the liquid material flows are not included (addressed) in the following)

Starting reaction gas mixture 1 is a mixture of the following feed gas streams:

87114 kg/h of a mixture of molecular oxygen (21.00% by weight) and molecular nitrogen (79.00% by weight) simulating ambient air;

16000 kg/h chemical grade propene (94.77% by wt. propene and 5.23% by wt. propane); and 77110 kg/h recycled gaseous stream P.

The temperature of starting reaction gas mixture 1 is 200° C. and its pressure is 2.434 bar. The composition of starting reaction gas mixture 1 fed through the reaction tubes first stage tube bundle reactor is:

| | |
|---|---|
| 0.03% by vol. of | formaldehyde |
| 0.01% by vol. of | acrolein |
| 1.06% by vol. of | water |
| 0.02% by vol. of | acetic acid |
| 0.02% by vol. of | acrylic acid |
| 6.00% by vol. of | propene |
| 0.57% by vol. of | propane |
| 10.80% by vol. of | molecular oxygen |
| 0.64% by vol. of | carbon dioxide |
| 0.30% by vol. of | carbon monoxide |
| 80.55% by vol. of | molecular nitrogen |

Temperature $T^A$ is 326° C. Temperature $T^B$ is 335° C.

The temperature in the catalytically active part of the fixed catalyst bed in the reaction tube is in the range of 325° C. to 400° C.

The propene hourly space velocity on the fixed catalyst bed (Section 2+Section 3 in the reaction tube) is 161 (l (STP)/l·h).

The single pass propene conversion is 95.5 mol % and the accompanying selectivity $S^A$ of the formation of acrolein is 92.0 mol %.

The stream of 180224 kg/h of product gas mixture 1 leaving the first reaction stage with a temperature of 360° C. and a pressure of 1.834 bar has the following composition:

| | |
|---|---|
| 0.03% by vol. of | formaldehyde |
| 5.28% by vol. of | acrolein |
| 7.06% by vol. of | water |
| 0.12% by vol. of | acetic acid |
| 0.23% by vol. of | acrylic acid |
| 0.27% by vol. of | propene |
| 0.57% by vol. of | propane |
| 4.41% by vol. of | molecular oxygen |
| 0.99% by vol. of | carbon dioxide |
| 0.47% by vol. of | carbon monoxide |
| 80.57% by vol. of | molecular nitrogen |

The temperature of the product gas mixture leaving the first reaction stage (product gas mixture 1) is reduced by indirect cooling in the after cooler. The stream of thus cooled product gas mixture 1 (temperature=250° C.) is mixed with a stream of 18984 kg/h secondary mixture of molecular oxygen (21.00% by weight) and molecular nitrogen (79.00% by weight) having a temperature of 165.00° C. and a pressure of 2.50 bar.

The composition of the 199208 kg/h of thus resulting starting reaction gas mixture 2 (temperature: 242.9° C.; pressure: 1.809 bar) fed through the reaction tubes of the second stage tube bundle reactor is:

| | |
|---|---|
| 0.02% by vol. of | formaldehyde |
| 4.77% by vol. of | acrolein |
| 6.37% by vol. of | water |
| 0.11% by vol. of | acetic acid |
| 0.21% by vol. of | acrylic acid |
| 0.24% by vol. of | propene |
| 0.51% by vol. of | propane |
| 5.82% by vol. of | molecular oxygen |
| 0.89% by vol. of | carbon dioxide |
| 0.42% by vol. of | carbon monoxide |
| 80.64% by vol. of | molecular nitrogen |

Temperature $T^C$ is 265° C. Temperature $T^D$ is 271° C.

The temperature in the catalytically active part of the fixed catalyst bed in the reaction tube is in the range of 264° C. to 302° C.

The acrolein hourly space velocity on the fixed catalyst bed (Section 2 and Section 3 in the reaction tube) is 129 (l (STP)/l·h).

The single pass acrolein conversion is 99.5 mol % and the accompanying selectivity $S^{AA}$ of the formation of acrylic acid and assessed over both reaction stages and based on converted propene is 89.8 mol %.

The product gas mixture (199208 kg/h, T=250° C., P=1.509 bar) leaving the second stage reactor (product gas mixture 2) at its entrance into the separating zone is cooled in the spray cooler (quench 1) to a temperature of 120° C. The composition of product gas mixture 2 is:

| | |
|---|---|
| 0.21% by vol. of | formaldehyde |
| 0.03% by vol. of | acrolein |
| 6.87% by vol. of | water |
| 0.02% by vol. of | formic acid |
| 0.12% by vol. of | acetic acid |
| 4.74% by vol. of | acrylic acid |
| 0.03% by vol. of | maleic anhydride |
| 0.25% by vol. of | propene |
| 0.52% by vol. of | propane |
| 3.00% by vol. of | molecular oxygen |
| 1.31% by vol. of | carbon dioxide |
| 0.60% by vol. of | carbon monoxide |
| 82.30% by vol. of | molecular nitrogen |

The liquid to be used for the direct cooling of the product gas mixture 2 (quench liquid 1) is a portion (498518 kg/h, T=116.1° C.) of bottoms liquid which is withdrawn in a total amount of 501928 kg/h (T=116.1° C.) from the bottom of the condensation column described below. Contents of this bottom liquid are:

| | |
|---|---|
| 0.58% by wt. of | water |
| 0.01% by wt. of | formic acid |
| 0.23% by wt. of | acetic acid |
| 33.06% by wt. of | acrylic acid |
| 0.03% by wt. of | propionic acid |
| 0.18% by wt. of | furfurals |
| 0.15% by wt. of | benzaldehyde |
| 5.55% by wt. of | maleic anhydride |
| 50.02% by wt. of | diacrylic acid |
| 0.78% by wt. of | MEHQ |
| 0.79% by wt. of | benzoic acid |
| 0.30% by wt. of | phthalic anhydride |
| 0.32% by wt. of | phenothiazine |
| 8.00% by wt. of | polyacrylic acid |

The mixture of product gas mixture cooled to 120° C. and unevaporated quench liquid 1 having same temperature which results in the direct cooling is conducted as such into the bottom of the condensation column. The pressure in the bottom space and in the quench 1 is 1.479 bar. The other portion (3410 kg/h) of bottoms liquid withdrawn from the bottom of the condensation column is supplied to the second stripping column and fed into its middle section.

The energy required for cracking diacrylic acid and polyacrylic acid (both Michael adducts) contained in the bottoms liquid into acrylic acid is supplied into the second stripping column by means of an external forced-circulation three-flow tube bundle flash evaporator, which is fed with bottoms liquid of the second stripping column. As it flows through the heat exchanger tubes, the bottoms liquid is heated, and its major amount thereafter recycled into the bottom of the second stripping column. A small amount of the total amount of bottoms liquid conducted through the heat exchanger is branched off, degassed and, diluted with methanol, sent to residue incineration.

In addition, the first laden gas conducted out of the first stripping column at the top thereof is fed into the bottom of the second stripping column. Second laden gas is conducted out of the top of the second stripping column in an amount of 18875 kg/h (temperature=65° C., pressure=1.40 bar) and fed into quench 1 and/or the bottom of the condensation column. Contents of the second laden gas are:

| | |
|---|---|
| 0.05% by vol. of | formaldehyde |
| 0.02% by vol. of | acrolein |
| 5.68% by vol. of | water |
| 0.41% by vol. of | acetic acid |
| 5.25% by vol. of | acrylic acid |
| 0.25% by vol. of | propene |
| 0.53% by vol. of | propane |
| 3.02% by vol. of | molecular oxygen |
| 1.32% by vol. of | carbon dioxide |
| 0.61% by vol. of | carbon monoxide |
| 82.86% by vol. of | molecular nitrogen |

67962 kg/h of high boiler fraction are conducted from the first collecting tray of the condensation column into the bottom space disposed below the first collecting tray. The high boiler fraction has, at a temperature of 99.0° C. and pressure of approximately 1.479 bar, the following contents:

| | |
|---|---|
| 0.01% by wt. of | formaldehyde |
| 1.27% by wt. of | water |
| 0.01% by wt. of | formic acid |
| 0.48% by wt. of | acetic acid |
| 90.98% by wt. of | acrylic acid |
| 0.07% by wt. of | propionic acid |
| 0.44% by wt. of | furfurals |
| 0.27% by wt. of | benzaldehyde |
| 5.17% by wt. of | maleic anhydride |
| 1.15% by wt. of | diacrylic acid |
| 0.09% by wt. of | MEHQ |
| 0.03% by wt. of | benzoic acid |
| 0.01% by wt. of | phthalic anhydride |
| 0.02% by wt. of | phenothiazine |

The bottom temperature is 116.1° C. and the bottom pressure (at the liquid level) is 1.479 bar.

From the second collecting tray, 236076 kg/h crude acrylic acid with a temperature of 96.8° C. are withdrawn continuously at 1.443 bar as the first side draw, which has the following contents:

| | |
|---|---|
| 0.01% by wt. of | formaldehyde |
| 1.34% by wt. of | water |
| 0.02% by wt. of | formic acid |
| 0.90% by wt. of | acetic acid |
| 96.90% by wt. of | acrylic acid |
| 0.09% by wt. of | propionic acid |
| 0.19% by wt. of | furfurals |
| 0.03% by wt. of | benzaldehyde |
| 0.25% by wt. of | maleic anhydride |
| 0.24% by wt. of | diacrylic acid |
| 0.02% by wt. of | MEHQ |
| 0.01% by wt. of | phenothiazine |

32426 kg/h of the crude acrylic acid withdrawn from the second collecting tray, together with mother liquor (66487 kg/h) which has been obtained in the crystallizative further purification of withdrawn acrylic acid and has been heated to 90° C. in the indirect heat exchange with drawn crude acrylic acid and steam as heat carrier are recycled into the condensation column via respective inserted tubes immediately below the second collecting tray to the dual-flow tray which follows below the second collecting tray.

115000 kg/h of the crude acrylic acid withdrawn from the second collecting tray are with a temperature of 96.8° C. recycled directly above the second collecting tray through spray nozzles to keep this section wetted and prevent fouling.

88650 kg/h of the crude acrylic acid withdrawn from the second collecting tray are cooled to a temperature of 29° C. by the multistage indirect heat exchange. About 1000 kg/h of demineralized water are than added to the cooled acrylic acid.

The resulting mixture is cooled and subsequently crystallized in cooling disk crystallizers and the resulting crystal suspension purified in hydraulic melt wash columns as described in WO 2008/090190 on pages 49 and 50. From the melt circuits which are stabilized by the addition of a solution of MEHQ in glacial acrylic acid, 22162 kg/h of the desired separated acrylic acid are withdrawn as glacial acrylic acid showing the following contents:

| | |
|---|---|
| 0.01% by wt. of | water |
| 0.20% by wt. of | acetic acid |
| 99.75% by wt. of | acrylic acid |
| 0.03% by wt. of | propionic acid |
| 0.01% by wt. of | MEHQ |

In 904 kg/h of the aforementioned glacial acrylic acid 11 kg/h of PTZ (phenothiazine) are dissolved to prepare an inhibitor solution 1 at 25° C. The remaining flow of glacial acrylic acid continuously withdrawn from the melt circuits is fed continuously in the storage tank.

The mother liquor removed in the wash columns is initially conducted into a heatable collecting vessel and from there into a tank. From this tank it is (as already mentioned) heated to 90° C. with thermal integration and recycled in a mass flow of 66487 kg/h, together (as a mixed flow (92.2° C., 1.10 bar)) with 32426 kg/h of the crude acrylic acid withdrawn at the second collecting tray of the condensation column, to the condensation column at the upper part of the series of dual-flow trays below the second collecting tray.

The composition of the recycled mother liquor is as follows:

| | |
|---|---|
| 1.78% by wt. of | water |
| 0.02% by wt. of | formic acid |
| 1.13% by wt. of | acetic acid |
| 95.95% by wt. of | acrylic acid |
| 0.11% by wt. of | propionic acid |
| 0.26% by wt. of | furfurals |
| 0.04% by wt. of | benzaldehyde |
| 0.34% by wt. of | maleic anhydride |
| 0.32% by wt. of | diacrylic acid |
| 0.03% by wt. of | MEHQ |
| 0.01% by wt. of | phenothiazine |
| 0.01% by wt. of | methylene glycol |

834535 kg/h of acid water with a temperature of 53.4° C. and a pressure of 1.229 bar are withdrawn as the second side withdraw from the third collecting tray.

The acid water has the following contents:

| | |
|---|---|
| 0.08% by wt. of | formaldehyde |
| 0.01% by wt. of | acrolein |
| 0.02% by wt. of | allyl formate |
| 78.83% by wt. of | water |
| 0.57% by wt. of | formic acid |
| 6.11% by wt. of | acetic acid |
| 7.98% by wt. of | acrylic acid |
| 6.40% by wt. of | methylene glycol |

27112 kg/h of the acid water withdrawn (53.4° C.) are recycled to the uppermost Thormann tray together with 35 kg/h of inhibitor solution 1 (25° C.) and 28 kg/h molten MEHQ (T=80° C.). 880 kg/h of inhibitor solution 1 are recycled (with a temperature of 25° C.) to the arrangement of the single-flow Thormann trays (approximately after two-thirds of the length of this Thormann separation section (counted from its bottom)).

458.31 m³/h of the acid water withdrawn are recycled at a temperature of 28.4° C. to the middle of an equidistant arrangement of valve trays which is described in more detail below (the cooling is effected by means of multistage indirect heat exchange).

325000 kg/h of the acid water withdrawn are recycled at a temperature of 23.4° C. to the uppermost of the aforementioned equidistant arrangement of valve trays (the cooling is effected together with the aforementioned amount of acid water by means of multistage indirect heat exchange; the last cooling stage from 28.4° C. to 23.4° C. is effected thermally and with heat integration (liquid chemical grade propene is used as the coolant and evaporates at the same time; the resulting gaseous propene is subsequently used for the configuration of the starting reaction gas mixture 1 for the first stage of the heterogeneously catalyzed gas-phase partial oxidation of propene). 7423 kg/h of the acid water with-
drawn are fed to the extraction column for the purpose of the
extraction still to be performed thereafter.

Above the third collecting tray in the condensation col-
umn is mounted a sequence of two-flow valve trays in
equidistant arrangement. The pressure at the top of the
condensation column is 1.17 bar. At the top of the conden-
sation column 186030 kg/h of the residual gas mixture R
leave the separating column with a temperature of 24° C.
and the following contents:

| | |
|---|---|
| 0.06% by vol. of | formaldehyde |
| 0.03% by vol. of | acrolein |
| 2.38% by vol. of | water |
| 0.04% by vol. of | acetic acid |
| 0.04% by vol. of | acrylic acid |
| 0.28% by vol. of | propene |
| 0.58% by vol. of | propane |
| 91.15% by vol. of | molecular nitrogen |
| 3.32% by vol. of | molecular oxygen |
| 1.45% by vol. of | carbon dioxide |
| 0.67% by vol. of | carbon monoxide |

In an indirect heat exchanger the gas mixture R is heated
to 32° C. 92920 kg/h thereof are discharged of the produc-
tion process as off-gas stream O.

93110 kg/h of foresaid gas mixture R are compressed to
a pressure of 2.5 bar by means of a compressor, which raises
its temperature to approximately 150° C. 16000 kg/h thereof
are fed to the first stripping column within the separating
zone for stripping the extract from the acid water extraction.
The remaining 77110 kg/h of the compressed gas mixture
are (as cycle gas) recycled as gaseous stream P into the first
reaction stage 1 as feed stream for preparing the stream of
starting reaction gas mixture 1. The total of the mass flows
off-gas stream O and of cycle gaseous stream P constitutes
the total mass flow M of residual gas mixture R which is
continuously conducted out of the separating zone. It con-
tains, of the total molar amount of those compounds con-
tained in the product gas mixture 2 continuously transported
into the separating zone, which have as pure compounds at
a working pressure of 1 bar a boiling point below 250 K,
99.99 mol %.

The mass flow of the recycle gaseous stream P is 45.35%
of the total mass flow M of residual gas mixture R which is
continuously conducted out of the separating zone.

The 7423 kg/h of acid water to be extracted (tempera-
ture=53.4° C.) are fed into the extraction column below the
lowermost packing via tubular distributors having appropri-
ate passage orifices. Above the uppermost packing of the
extraction column, a mixture (temperature=50° C.) of fresh
Palatinol® A and extractant (in a ratio of the respective mass
flows of 1:240) which has been recycled from the first
stripping column and has been stripped free therein before-
hand is introduced in a mass flow essentially equal to the
7423 kg/h of acid water. The recycled extractant has the
following contents:

| | |
|---|---|
| ≤0.5% by wt. of | acrylic acid |
| ≤0.03% by wt. of | acetic acid |
| ≤0.02% by wt. of | water |
| ≤0.001% by wt. of | formic acid |
| ≤0.0035% by wt. of | acrolein |
| ≤0.00005% by wt. of | propionic acid |

-continued

| | |
|---|---|
| ≤0.0001% by wt. of | furfurals |
| ≤0.001% by wt. of | allyl formate |
| ≤0.03% by wt. of | MEHQ |
| ≥99.5% by wt. of | Palatinol ® A |

The specific mass of the acid water (temperature=53.4°
C.) is 1018.2 kg/m³. The extractant is likewise introduced
via tubular distributors having appropriate passage orifices.
The acid water forms the continuous phase and the extract-
ant forms the phase dispersed in droplet form (droplet
diameter in the range from 2 to 5 mm), which descends in
the aqueous phase. At the top of the extraction column the
raffinate is withdrawn. It is sent to incineration. The extract
is withdrawn from the bottom of the extraction column. It
contains the acrylic acid extracted from the acid water. The
entirety of the extract is conducted to the top of the first
stripping column. Beforehand the extract is heated to 95° C.
by indirect heat exchange in a plate heat exchanger. The heat
carrier is bottom liquids withdrawn at the first stripping
column.

Below the lowermost dual-flow tray the 16000 kg/h of the
compressed residual gas mixture R (2.5 bar, 150° C.) are
conducted into the first stripping column, where it ascends
in countercurrent to the extract descending in the stripping
column. At the top of the first stripping column first laden
(especially with water and acrylic acid) gas is conducted out
(16875 kg/h) and fed into the second stripping column. The
composition of the first laden gas is:

| | |
|---|---|
| 0.06% by vol. of | formaldehyde |
| 0.03% by vol. of | acrolein |
| 5.94% by vol. of | water |
| 0.38% by vol. of | acetic acid |
| 0.87% by vol. of | acrylic acid |
| 0.26% by vol. of | propene |
| 0.55% by vol. of | propane |
| 3.16% by vol. of | molecular oxygen |
| 1.38% by vol. of | carbon dioxide |
| 0.64% by vol. of | carbon monoxide |
| 86.73% by vol. of | molecular nitrogen |

Bottoms liquid is withdrawn continuously from the bot-
tom of the first stripping column. One portion of the bottoms
liquid withdrawn from the first stripping column are cooled
by two-stage indirect heat exchange (the first stage in a plate
heat exchanger with thermal integration against extract), and
recycled as extractant to the top of the extraction column.
The other portion of bottoms liquid withdrawn from the first
stripping column are heated to about 160° C. in an external
force-circulation tube bundle flash evaporator and recycled
into the bottom of the first stripping column.

The overall propene conversion (based on multiple pass)
in this Example 1 is 97.50 mol % (calculated from the
difference between propene fed as content of the chemical
grade propene via starting reaction gas mixture 1 into the
production process and propene discharged of the produc-
tion process as content of off-gas stream O).

The overall yield of acrylic acid produced in Example 1
is 85.1 mol % (calculated from acrylic acid continuously fed
into the storage tank as content of glacial acrylic acid and
propene fed into the production process as content of
chemical grade propene via starting reaction gas mixture 1).

From the acrylic acid contained in product gas mixture 2
99.27 mol % are in the separating zone transferred into the
liquid phase.

Production of Synthesis Gas from the Off-Gas of this Comparison Example

The content of molecular nitrogen in the off-gas resulting in this Comparison Example is too high to produce economically viable syngas from it.

The invention claimed is:

1. A process for the continuous production of either acrolein or acrylic acid as the target product from propene comprising under stationary operating conditions A) as an obligatory measure continuously passing in a first reaction stage a stream of a starting reaction gas mixture 1 consisting of from 2 to 15% by volume of propene, from 2.4 to 37.5% by volume of molecular oxygen, from 0.5 to 20% by volume of water, from 0 to 5% by volume of molecular nitrogen, from 1 to 30% by volume of carbon monoxide, from 1.5 to 65% by volume of carbon dioxide, from 0 to 80% by volume of one or more than one hydrocarbon selected from the group consisting of methane, ethane, propane, n-butane, isobutane and ethene, and from >0 to 5% by volume of other compounds including but not limited to acrolein and/or acrylic acid, and containing the molecular oxygen and the propene in a molar $O_2$:propene ratio ranging from 1.2 to 2.5, the carbon dioxide and the carbon monoxide in a molar $CO_2$:CO ratio ranging from 1 to 4, and the molecular oxygen and the molecular nitrogen in a molar $O_2$:$N_2$ ratio of at least 0.5, at a reaction temperature of from 250° C. to 500° C. and a working pressure of from 1 bar to 6 bar through a first fixed catalyst bed comprising shaped catalyst bodies whose active mass is at least one multimetal oxide containing molybdenum (Mo), bismuth (Bi) and iron (Fe) in such a way, that the propene conversion on single pass is from 80 mol % to 99 mol % and the accompanying selectivity $S^A$ of the formation of the target product acrolein is from 70 mol % to 99 mol % to obtain a stream of the target product acrolein containing product gas mixture 1 leaving the first reaction stage, and, B) in case of acrylic acid being the target product, optionally reducing the temperature of the product gas mixture leaving the first reaction stage by direct, indirect or direct and indirect cooling, optionally adding secondary gas to said product gas mixture in the form of molecular oxygen, or inert gas, or molecular oxygen and inert gas, and subsequently continuously passing in a second reaction stage a stream of the thus resulting starting reaction gas mixture 2 consisting of from 2 to 15% by volume of acrolein, from 1 to 45% by volume of molecular oxygen, from 2 to 30% by volume of water, from 0 to 5% by volume of molecular nitrogen, from 1 to 30% by volume of carbon monoxide, from 1.5 to 65% by volume of carbon dioxide, from 0 to 80% by volume of one or more than one hydrocarbon selected from the group consisting of methane, ethane, propane, n-butane, isobutane and ethene, and from >0 to 5% by volume of other compounds including but not limited to propene and/or acrylic acid, and containing the molecular oxygen and the acrolein in a molar $O_2$:acrolein ratio ranging from 0.5 to 3, the carbon dioxide and the carbon monoxide in a molar $CO_2$:CO ratio ranging from 1 to 4, and the molecular oxygen and the molecular nitrogen in a molar $O_2$:$N_2$ ratio of at least 0.25, at a reaction temperature of from 200° C. to 450° C. and a working pressure of from 1 bar to 6 bar through a second fixed catalyst bed comprising shaped catalyst bodies whose active mass is at least one multimetal oxide containing molybdenum (Mo) and vanadium (V) in such a way, that the acrolein conversion on single pass is from 95 mol % to 99.99 mol % and the accompanying selectivity $S^{AA}$ of the formation of the target product acrylic acid assessed over both reaction stages and based on converted propene is from 80 mol % to 99.9 mol % to obtain a stream of the target product acrylic acid containing product gas mixture 2 leaving the second reaction stage, and C) either continuously transporting the stream of the target product acrolein containing product gas mixture 1 or the stream of the target product acrylic acid containing product gas mixture 2 into a separating zone and separating in the separating zone the respective target product from the respective product gas mixture through transferring at least 95 mol % of the respective target product contained in the respective product gas mixture from the gaseous phase into the liquid phase and continuously conducting out of the separating zone a total mass flow M of a residual gas mixture R which contains, of the total molar amount of those compounds contained in the product gas mixture continuously transported into the separating zone, which have as pure compounds at a working pressure of 1 bar a boiling point below 250 K, at least 95 mol % and

D) recycling as gaseous stream P having the same composition as the residual gas mixture R a partial stream of the total mass flow M of residual gas mixture R continuously conducted out of the separating zone into the first reaction stage 1 as feed stream for preparing the stream of the starting reaction gas mixture 1 which shall contain the gaseous stream P, and discharging of the production process as off-gas stream O, having the same composition as the residual gas mixture R, the difference between the total mass flow M of residual gas mixture R continuously conducted out of the separating zone and the mass flow of recycle gaseous stream P, wherein a) the mass flow of the recycle gaseous stream P is at least 85% but not more than 99.5% of the total mass flow M of residual gas mixture R continuously conducted out of the separating zone, b) the mass flow of the off-gas stream O is not more than 15% but at least 0.5% of the total mass flow M of residual gas mixture R continuously conducted out of the separating zone, and c) the composition C of the residual gas mixture R is from 0.01 to 1% by volume of propene, from 1 to 10% by volume of molecular oxygen, from 0.5 to 25% by volume of water, from 0 to 20% by volume of molecular nitrogen, from 0.5 to 40% by volume of carbon monoxide, from 1 to 75% by volume of carbon dioxide, from 0 to 92% by volume of one or more than one hydrocarbon selected from the group consisting of methane, ethane, propane, n-butane, isobutane and ethene, and from 0.01 to 5% by volume of other compounds including but not limited to acrolein and/or acrylic acid, wherein the starting reaction gas mixture 1 is formed from feed streams comprising oxygen of a purity of at least 90% by volume of $O_2$ and no more than 10% by volume of $N_2$; and wherein the off-gas stream oxygen is directly suitable for use as synthesis gas or as an additive to synthesis gas in a downstream chemical process, without prior removal of molecular nitrogen.

2. The process according to claim 1, wherein the first fixed catalyst bed of the first reaction stage comprises catalyst bodies whose active mass is at least one multimetal oxide of the general formula I $$Mo_{12}Bi_aFe_bX^1_cX^2_dX^3_eX^4_fO_n \qquad (I)$$

in which the variables are each defined as follows:
$X^1$=nickel or cobalt,
$X^2$=thallium, an alkali metal or an alkaline earth metal,
$X^3$=zinc, phosphorus, arsenic, boron, antimony, tin, cerium, lead or tungsten,
$X^4$=silicon, aluminum, titanium or zirconium,
a=from 0.5 to 5,
b=from 2 to 4,
c=from 3 to 10,
d=from 0.02 to 2,
e=from 0 to 5,
f=from 0 to 10 and
n=a number which is determined by the valency and frequency of the elements in I other than oxygen.

3. The process according to claim 1, wherein the second fixed catalyst bed of the second reaction stage comprises catalyst bodies whose active mass is at least one multimetal oxide of the general formula III $$Mo_{12}V_aX^1_bX^2_cX^3_dX^4_eX^5_fX^6_gO_n \qquad (III)$$

in which the variables are each defined as follows:
$X^1$=W, Nb, Ta, Cr or Ce
$X^2$=Cu, Ni, Co, Fe, Mn or Zn,
$X^3$=Sb or Bi,
$X^4$=one or more alkali metals,
$X^5$=one or more alkaline earth metals,
$X^6$=Si, Al, Ti or Zr,
a=from 1 to 6,
b=from 0.2 to 4,
c=from 0.5 to 18,
d=from 0 to 40,
e=from 0 to 2,
f=from 0 to 4,
g=from 0 to 40 and
n=a number which is determined by the valency and frequency of the elements in III other than oxygen.

4. The process according to claim 1, wherein the propene hourly space velocity on the first fixed catalyst bed in the first reaction stage is from 50 to 300 1 (STP)/l·h.

5. The process according to claim 1, wherein the acrolein hourly space velocity on the second fixed catalyst bed in the second reaction stage is from 40 to 290 1 (STP)/l·h.

6. The process according to claim 1, wherein the starting reaction gas mixture 1 is formed from feed streams comprising
recycle gaseous stream P;
a propene source;
a source of molecular oxygen;
optionally a stream of steam; and
optionally one or more streams of one or more than one hydrocarbon selected from the group consisting of methane, natural gas, ethane, propane, n-butane, isobutane and ethene.

7. The process according to claim 1, wherein a ratio $Q=(n_{CO})/(n_{CO}+n_{hydrocarbon})$ in the starting reaction gas mixture 1 ranges from >0 to 0.8.

8. The process according to claim 1, wherein the starting reaction gas mixture 1 is formed from feed streams comprising oxygen of a purity of at least 95% by vol. $O_2$ and not more than 5% by vol. $N_2$ as a source of molecular oxygen.

9. The process according to claim 1, wherein the mass flow of the recycle gaseous stream P is at least 90% but not more than 99.5% of the mass flow M of residual gas mixture R continuously conducted out of the separating zone and the mass flow of the off-gas stream O is not more than 10% but at least 1% of the total mass flow M of residual gas mixture R continuously conducted out of the separating zone.

10. The process according to claim 1, wherein the process comprises under stationary operating conditions
A) as an obligatory measure continuously passing in a first reaction stage a stream of a starting reaction gas mixture 1 consisting of
from 2 to 15% by volume of propene,
from 2.4 to 37.5% by volume of molecular oxygen,
from 0.5 to 10% by volume of water,
from 0 to 5% by volume of molecular nitrogen,
from 15 to 25% by volume of carbon monoxide,
from 20 to 55% by volume of carbon dioxide,
from 10 to 30% by volume of at least one hydrocarbon selected from the group consisting of methane, ethane, propane, n-butane, isobutane and ethane, and
from >0 to 5% by volume of other compounds including but not limited to acrolein and/or acrylic acid,
and containing
the molecular oxygen and the propene in a molar $O_2$:propene ratio ranging from 1.2 to 2.5,
the carbon dioxide and the carbon monoxide in a molar $CO_2$:CO ratio ranging from 1 to 4,
and the molecular oxygen and the molecular nitrogen in a molar $O_2$:$N_2$ ratio of at least 0.5,
at a reaction temperature of from 250° C. to 500° C. and a working pressure of from 1 bar to 6 bar through a first fixed catalyst bed comprising shaped catalyst bodies whose active mass is at least one multimetal oxide containing molybdenum (Mo), bismuth (Bi) and iron (Fe) in such a way, that the propene conversion on single pass is from 80 mol % to 99 mol % and the accompanying selectivity $S^A$ of the formation of the target product acrolein is from 70 mol % to 99 mol % to obtain a stream of the target product acrolein containing product gas mixture 1 leaving the first reaction stage,
and,
B) in case of acrylic acid being the target product,
optionally reducing the temperature of the product gas mixture leaving the first reaction stage by direct, indirect or direct and indirect cooling, optionally adding secondary gas to said product gas mixture in the form of molecular oxygen, or inert gas, or molecular oxygen and inert gas, and subsequently continuously passing in a second reaction stage a stream of the thus resulting starting reaction gas mixture 2 consisting of from 2 to 15% by volume of acrolein, from 1 to 45% by volume of molecular oxygen, from 2 to 20% by volume of water, from 0 to 5% by volume of molecular nitrogen, from 15 to 25% by volume of carbon monoxide, from 20 to 55% by volume of carbon dioxide, from 10 to 30% by volume of at least one hydrocarbon selected from the group consisting of methane, ethane, propane, n-butane, isobutane and ethene, and from >0 to 5% by volume of other compounds including but not limited to propene and/or acrylic acid, and containing the molecular oxygen and the acrolein in a molar $O_2$:acrolein ratio ranging from 0.5 to 3, the carbon dioxide and the carbon monoxide in a molar $CO_2$:CO ratio ranging from 1 to 4, and the molecular oxygen and the molecular nitrogen in a molar $O_2$:$N_2$ ratio of at least 0.25, at a reaction temperature of from 200° C. to 450° C. and a working pressure of from 1 bar to 6 bar through a second fixed catalyst bed comprising shaped catalyst bodies whose active mass is at least one multimetal oxide containing molybdenum (Mo) and vanadium (V) in such a way, that the acrolein conversion on single pass is from 95 mol % to 99.99 mol % and the accompanying selectivity $S^{AA}$ of the formation of the target product acrylic acid assessed over both reaction stages and based on converted propene is from 80 mol % to 99.9 mol % to obtain a stream of the target product acrylic acid containing product gas mixture 2 leaving the second reaction stage, and C) either continuously transporting the stream of the target product acrolein containing product gas mixture 1 or the stream of the target product acrylic acid containing product gas mixture 2 into a separating zone and separating in the separating zone the respective target product from the respective product gas mixture through transferring at least 95 mol % of the respective target product contained in the respective product gas mixture from the gaseous phase into the liquid phase and continuously conducting out of the separating zone a total mass flow M of a residual gas mixture R which contains, of the total molar amount of those compounds contained in the product gas mixture continuously transported into the separating zone, which have as pure compounds at a working pressure of 1 bar a boiling point below 250 K, at least 95 mol % and

D) recycling as gaseous stream P having the same composition as the residual gas mixture R a partial stream of the total mass flow M of residual gas mixture R continuously conducted out of the separating zone into the first reaction stage 1 as feed stream for preparing the stream of the starting reaction gas mixture 1 which shall contain the gaseous stream P, and discharging of the production process as off-gas stream O, having the same composition as the residual gas mixture R, the difference between the total mass flow M of residual gas mixture R continuously conducted out of the separating zone and the mass flow of recycle gaseous stream P, wherein a) the mass flow of the recycle gaseous stream P is at least 95% but not more than 98% of the total mass flow M of residual gas mixture R continuously conducted out of the separating zone, b) the mass flow of the off-gas stream O is not more than 5% but at least 2% of the total mass flow M of residual gas mixture R continuously conducted out of the separating zone, and c) the composition C of the residual gas mixture R is from 0.05 to 0.5% by volume of propene, from 1 to 4% by volume of molecular oxygen, from 0.5 to 10% by volume of water, from 0 to 10% by volume of molecular nitrogen, from 15 to 30% by volume of carbon monoxide, from 30 to 60% by volume of carbon dioxide, from 10 to 50% by volume of at least one hydrocarbon selected from the group consisting of methane, ethane, propane, n-butane, isobutane and ethene, and from 0.01 to 5% by volume of other compounds including but not limited to acrolein and/or acrylic acid.

11. The process according to claim 10, wherein the starting reaction gas mixture 1 is formed from feed streams consisting of a propene feedstock stream containing ≥90% by vol. propene and ≤10% by vol. but ≥2% by vol. propane, a stream of molecular oxygen of a purity of at least ≥99.0% by vol. and ≤99.9% by vol. $O_2$ and ≤1% by vol. and ≥0.1% by vol. $N_2$, and recycle gaseous stream P.

12. The process according to claim 1, wherein the process comprises under stationary operating conditions A) as an obligatory measure continuously passing in a first reaction stage a stream of a starting reaction gas mixture 1 consisting of from 2 to 15% by volume of propene, from 2.4 to 37.5% by volume of molecular oxygen, from 0.5 to 10% by volume of water, from 0 to 5% by volume of molecular nitrogen, from 1.2 to 15% by volume of carbon monoxide, from 3 to 30% by volume of carbon dioxide, from 40 to 80% by volume of at least one hydrocarbon selected from the group consisting of methane, ethane, propane, n-butane, isobutane and ethene, and from >0 to 5% by volume of other compounds including but not limited to acrolein and/or acrylic acid, and containing the molecular oxygen and the propene in a molar $O_2$:propene ratio ranging from 1.2 to 2.5, the carbon dioxide and the carbon monoxide in a molar $CO_2$:CO ratio ranging from 1 to 4, the molecular oxygen and the molecular nitrogen in a molar $O_2$:$N_2$ ratio of at least 0.5, and the carbon monoxide and the total molar amount (quantity) of hydrocarbons in a molar CO: total hydrocarbons ratio ranging from >0 to 0.3, at a reaction temperature of from 250° C. to 500° C. and a working pressure of from 1 bar to 6 bar through a first fixed catalyst bed comprising shaped catalyst bodies whose active mass is at least one multimetal oxide containing molybdenum (Mo), bismuth (Bi) and iron (Fe) in such a way, that the propene conversion on single pass is from 80 mol % to 99 mol % and the accompanying selectivity $S^A$ of the formation of the target product acrolein is from 70 mol % to 99 mol % to obtain a stream of the target product acrolein containing product gas mixture 1 leaving the first reaction stage, and, B) in case of acrylic acid being the target product, optionally reducing the temperature of the product gas mixture leaving the first reaction stage by direct, indirect or direct and indirect cooling, optionally adding secondary gas to said product gas mixture in the form of molecular oxygen, or inert gas, or molecular oxygen and inert gas, and subsequently continuously passing in a second reaction stage a stream of the thus resulting starting reaction gas mixture 2 consisting of from 2 to 15% by volume of acrolein, from 1 to 45% by volume of molecular oxygen, from 2 to 20% by volume of water, from 0 to 5% by volume of molecular nitrogen, from 1.2 to 15% by volume of carbon monoxide, from 3 to 30% by volume of carbon dioxide, from 40 to 80% by volume of at least one hydrocarbon selected from the group consisting of methane, ethane, propane, n-butane, isobutane and ethene, and from >0 to 5% by volume of other compounds including but not limited to propene and/or acrylic acid, and containing the molecular oxygen and the acrolein in a molar $O_2$:acrolein ratio ranging from 0.5 to 3, the carbon dioxide and the carbon monoxide in a molar $CO_2$:CO ratio ranging from 1 to 4, the molecular oxygen and the molecular nitrogen in a molar $O_2$:$N_2$ ratio of at least 0.25, and the carbon monoxide and the total molar amount of hydrocarbons including acrolein in a molar CO: total hydrocarbons ratio ranging from >0 to 0.3, at a reaction temperature of from 200° C. to 450° C. and a working pressure of from 1 bar to 6 bar through a second fixed catalyst bed comprising shaped catalyst bodies whose active mass is at least one multimetal oxide containing molybdenum (Mo) and vanadium (V) in such a way, that the acrolein conversion on single pass is from 95 mol % to 99.99 mol % and the accompanying selectivity $S^{AA}$ of the formation of the target product acrylic acid assessed over both reaction stages and based on converted propene is from 80 mol % to 99.9 mol % to obtain a stream of the target product acrylic acid containing product gas mixture 2 leaving the second reaction stage, and C) either continuously transporting the stream of the target product acrolein containing product gas mixture 1 or the stream of the target product acrylic acid containing product gas mixture 2 into a separating zone and separating in the separating zone the respective target product from the respective product gas mixture through transferring at least 95 mol % of the respective target product contained in the respective product gas mixture from the gaseous phase into the liquid phase and continuously conducting out of the separating zone a total mass flow M of a residual gas mixture R which contains, of the total molar amount of those compounds contained in the product gas mixture continuously transported into the separating zone, which have as pure compounds at a working pressure of 1 bar a boiling point below 250 K, at least 95 mol % and

D) recycling as gaseous stream P having the same composition as the residual gas mixture R a partial stream of the total mass flow M of residual gas mixture R continuously conducted out of the separating zone into the first reaction stage 1 as feed stream for preparing the stream of the starting reaction gas mixture 1 which shall contain the gaseous stream P, and discharging of the production process as off-gas stream O, having the same composition as the residual gas mixture R, the difference between the total mass flow M of residual gas mixture R continuously conducted out of the separating zone and the mass flow of recycle gaseous stream P, wherein a) the mass flow of the recycle gaseous stream P is at least 90% 75% but not more than 98% of the total mass flow M of residual gas mixture R continuously conducted out of the separating zone, b) the mass flow of the off-gas stream O is not more than 10% 25% but at least 2% of the total mass flow M of residual gas mixture R continuously conducted out of the separating zone, and c) the composition C of the residual gas mixture R is from 0.05 to 0.8% by volume of propene, from 1 to 4% by volume of molecular oxygen, from 0.5 to 10% by volume of water, from 0 to 10% by volume of molecular nitrogen, from 1.2 to 15% by volume of carbon monoxide, from 3 to 30% by volume of carbon dioxide, from 45 to 90% by volume of at least one hydrocarbon selected from the group consisting of methane, ethane, propane, n-butane, isobutane and ethene, and from 0.01 to 5% by volume of other compounds including but not limited to acrolein and/or acrylic acid.

13. The process according to claim 12, wherein the starting reaction gas mixture 1 is formed from feed streams consisting of a propene feedstock stream of polymer grade (propene feedstock containing ≥99% by vol. propene and ≤1% by vol. propane) or chemical grade propene (propene feedstock containing ≥90% by vol. propene and ≤10% by vol. but ≥2% by vol. propane), a stream of molecular oxygen of a purity of at least >99.0% by vol. and ≤99.9% by vol. $O_2$ and ≤1% by vol. and ≥0.1% by vol. $N_2$, recycle gaseous stream P and an additional stream of at least one hydrocarbon selected from the group consisting of methane, natural gas, ethene, propane, n-butane, isobutane and ethene.

14. The process according to claim 1, wherein the transferring of the respective target product from the gaseous phase into the liquid phase comprises the absorption of the respective target product into a liquid absorbent and/or the condensation of the respective target product from the gaseous phase in at least one separating column containing separating internals in which the respective product gas mixture is conducted ascending from the bottom upward.

15. The process according to claim 1, wherein the process is combined with a further process which comprises the conversion of off-gas stream O discharged of the production process and fed to said further process to a synthesis gas or mixing of said off-gas stream into another synthesis gas produced in said further process from any feedstock other than the off-gas O to yield a thus amended other synthesis gas.

16. The process according to claim 15, wherein the conversion of the off-gas stream O comprises at least one of the following reactions:

heterogeneously catalyzed steam reforming in the gas phase of hydrocarbon contained in the off-gas stream O;

heterogeneously catalyzed hydrogenation in the gas phase of $CO_2$ contained in the off-gas stream O;

heterogeneously catalyzed dry reformation in the gas phase of hydrocarbon with $CO_2$ being both contained in the off-gas stream O; or partial gas phase combustion of hydrocarbon and/or compounds being composed of C, H and O and being contained in the off-gas stream O.

17. The process according to claim 15, wherein the resulting synthesis gas and/or amended other synthesis gas is converted in a synthesis process to produce any chemical compound containing the elements C and H and optionally O.

18. A process for the continuous production of either acrolein or acrylic acid as the target product from propene comprising under stationary operating conditions A) as an obligatory measure continuously passing in a first reaction stage a stream of a starting reaction gas mixture 1 consisting of from 5 to 8% by volume of propene, from 7.5 to 16.8% by volume of molecular oxygen, from 0.5 to 10% by volume of water, from 0 to 2% by volume of molecular nitrogen, from 15 to 25% by volume of carbon monoxide, from 20 to 55% by volume of carbon dioxide, from 10 to 30% by volume of one or more than one hydrocarbon selected from the group consisting of methane, ethane, propane, n-butane, isobutane and ethene, and from >0 to 1% by volume of other compounds including but not limited to acrolein and/or acrylic acid, and containing the molecular oxygen and the propene in a molar $O_2$:propene ratio ranging from 1.5 to 2.1, the carbon dioxide and the carbon monoxide in a molar $CO_2$:CO ratio ranging from 1.5 to 3, and the molecular oxygen and the molecular nitrogen in a molar $O_2$:$N_2$ ratio of at least 1, at a reaction temperature of from 300° C. to 450° C. and a working pressure of from 1 bar to 3.5 bar through a first fixed catalyst bed comprising shaped catalyst bodies whose active mass is at least one multimetal oxide containing molybdenum (Mo), bismuth (Bi) and iron (Fe) in such a way, that the propene conversion on single pass is at least 92 mol % and the accompanying selectivity $S^A$ of the formation of the target product acrolein is at least 90 mol % to obtain a stream of the target product acrolein containing product gas mixture 1 leaving the first reaction stage, and, B) in case of acrylic acid being the target product, optionally reducing the temperature of the product gas mixture leaving the first reaction stage by direct, indirect or direct and indirect cooling, optionally adding secondary gas to said product gas mixture in the form of molecular oxygen, or inert gas, or molecular oxygen and inert gas, and subsequently continuously passing in a second reaction stage a stream of the thus resulting starting reaction gas mixture 2 consisting of from 4.5 to 8% by volume of acrolein, from 3.6 to 12% by volume of molecular oxygen, from 2 to 10% by volume of water, from 0 to 2% by volume of molecular nitrogen, from 15 to 25% by volume of carbon monoxide, from 20 to 55% by volume of carbon dioxide, from 10 to 30% by volume of one or more than one hydrocarbon selected from the group consisting of methane, ethane, propane, n-butane, isobutane and ethene, and from >0 to 1% by volume of other compounds including but not limited to propene and/or acrylic acid, and containing the molecular oxygen and the acrolein in a molar $O_2$:acrolein ratio ranging from 0.8 to 1.5, the carbon dioxide and the carbon monoxide in a molar $CO_2$:CO ratio ranging from 1.5 to 3, and the molecular oxygen and the molecular nitrogen in a molar $O_2$:$N_2$ ratio of at least 0.5, at a reaction temperature of from 230° C. to 390° C. and a working pressure of from 1 bar to 3.5 bar through a second fixed catalyst bed comprising shaped catalyst bodies whose active mass is at least one multimetal oxide containing molybdenum (Mo) and vanadium (V) in such a way, that the acrolein conversion on single pass is from 95 mol % to 99.99 mol % and the accompanying selectivity $S^{AA}$ of the formation of the target product acrylic acid assessed over both reaction stages and based on converted propene is at least 87 mol % to obtain a stream of the target product acrylic acid containing product gas mixture 2 leaving the second reaction stage, and C) either continuously transporting the stream of the target product acrolein containing product gas mixture 1 or the stream of the target product acrylic acid containing product gas mixture 2 into a separating zone and separating in the separating zone the respective target product from the respective product gas mixture through transferring at least 95 mol % of the respective target product contained in the respective product gas mixture from the gaseous phase into the liquid phase and continuously conducting out of the separating zone a total mass flow M of a residual gas mixture R which contains, of the total molar amount of those compounds contained in the product gas mixture continuously transported into the separating zone, which have as pure compounds at a working pressure of 1 bar a boiling point below 250 K, at least 95 mol % and

D) recycling as gaseous stream P having the same composition as the residual gas mixture R a partial stream of the total mass flow M of residual gas mixture R continuously conducted out of the separating zone into the first reaction stage 1 as feed stream for preparing the stream of the starting reaction gas mixture 1 which shall contain the gaseous stream P, and discharging of the production process as off-gas stream O, having the same composition as the residual gas mixture R, the difference between the total mass flow M of residual gas mixture R continuously conducted out of the separating zone and the mass flow of recycle gaseous stream P, wherein a) the mass flow of the recycle gaseous stream P is at least 95% but not more than 98% of the total mass flow M of residual gas mixture R continuously conducted out of the separating zone, b) the mass flow of the off-gas stream O is not more than 5% but at least 2% of the total mass flow M of residual gas mixture R continuously conducted out of the separating zone, and c) the composition C of the residual gas mixture R is
from 0.05 to 0.5% by volume of propene,
from 1 to 4% by volume of molecular oxygen,
from 0.5 to 10% by volume of water,
from 0 to 5% by volume of molecular nitrogen,
from 15 to 30% by volume of carbon monoxide,
from 30 to 60% by volume of carbon dioxide,
from 10 to 50% by volume of one or more than one hydrocarbon selected
from the group consisting of methane, ethane, propane, n-butane, isobutane and ethene, and
from 0.01 to 1% by volume of other compounds including but not limited to acrolein and/or acrylic acid, wherein the off-gas stream oxygen is directly suitable for use as synthesis gas or as an additive to synthesis gas in a downstream chemical process, without prior removal of molecular nitrogen.

*    *    *    *    *